(12) United States Patent
Thomson et al.

(10) Patent No.: US 8,765,470 B2
(45) Date of Patent: Jul. 1, 2014

(54) REPROGRAMMING IMMORTALIZED B-CELLS TO INDUCED PLURIPOTENT STEM CELLS

(75) Inventors: James Thomson, Madison, WI (US); Deepika Rajesh, Madison, WI (US); Sarah Jane Dickerson, Madison, WI (US); Amanda Mack, Madison, WI (US); Michael Miller, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 257 days.

(21) Appl. No.: 13/197,529

(22) Filed: Aug. 3, 2011

(65) Prior Publication Data
US 2012/0058562 A1 Mar. 8, 2012

Related U.S. Application Data

(60) Provisional application No. 61/370,615, filed on Aug. 4, 2010, provisional application No. 61/441,885, filed on Feb. 11, 2011.

(51) Int. Cl.
*C12N 15/00* (2006.01)
*C12N 15/63* (2006.01)
*C12N 15/85* (2006.01)

(52) U.S. Cl.
CPC .............. *C12N 15/63* (2013.01); *C12N 15/85* (2013.01); *C12N 2510/04* (2013.01)
USPC ............................ 435/377; 435/384; 435/455

(58) Field of Classification Search
CPC .................. C12N 2501/602; C12N 2501/603; C12N 2501/604; C12N 2501/606; C12N 2510/00; C12N 5/0696; C12N 2506/11; C12N 2501/608; C12N 2501/605; C12N 15/63; C12N 15/85; C12N 2502/11; C12N 2510/04; C12N 2800/108
See application file for complete search history.

(56) References Cited

U.S. PATENT DOCUMENTS

| | | | |
|---|---|---|---|
| 7,682,828 B2 | 3/2010 | Jaenisch et al. | 435/455 |
| 7,781,214 B2 | 8/2010 | Smith et al. | 435/377 |
| 2003/0211603 A1 | 11/2003 | Earp et al. | 435/366 |
| 2007/0238170 A1 | 10/2007 | Thomson et al. | 435/366 |
| 2010/0003757 A1 | 1/2010 | Mack et al. | 435/455 |

FOREIGN PATENT DOCUMENTS

| | | |
|---|---|---|
| WO | WO 03/100070 | 12/2003 |
| WO | WO 2008/124133 | 10/2008 |
| WO | WO 2009/157201 | 12/2009 |

OTHER PUBLICATIONS

Kempes et al. Immortalization of human primary B lymphocytes in vitro with DNA. PNAS, 1995, vol. 92, pp. 5875-5878.*
Xie et al. Stepwise Reprogramming of B Cells into Macrophages. Cell, 2004, vol. 117, pp. 663-676.*
Pereira et al. Heterokaryon-Based Reprogramming of Human B Lymphocytes for Pluripotency Requires Oct4 but Not Sox2. PLOS, 2008, vol. 4, pp. 1-14.*
Yu et al, Human Induced Pluripotent Stem Cells Free of Vector and Transgene Sequences. Supporting Online Material., Science, 2009, 10.1126/science.1172482, pp. 1-18.*
Altmann et al., "Transcriptional activation by EBV nuclear antigen 1 is essential for the expression of EBV's transforming genes," *Proc. Natl. Acad. Sci. USA*, 103(38):14188-14193, 2006.
Amoli et al. "EBV Immortalization of human B lymphocytes separated from small volumes of cryo-preserved whole blood," *Int. J. Epidemiol.*, 37(Suppl 1):i41-i45, 2008.
Bishop et al., "Molecular mechanisms of B-lymphocyte transformation by Epstein-Barr virus," *Microbes and Infection*, 4:853-857, 2002.
Carey et al., "Reprogramming of murine and human somatic cells using a single polycistronic vector," *Proc. Natl. Acad. Sci. USA*, 106:157-162, 2009.
Choi et al., "Reprogramming of EBV-immortalized B-lymphocyte cell lines into induced pluripotent stem cells," *Blood First Edition Paper*, prepublished online May 31, 2011. doi:10.1182/blood-2011-03-340620.
Cobaleda and Busslinger, "Developmental plasticity of lymphocytes," *Curr. Opin. Immunol.*, 20:139-148. 2008.
Cobaleda, "Reprogramming of B cells," *Methods Mol. Biol.*, 636:233-250, 2010.
Delecluse et al., "A first-generation packaging cell line for Epstein-Barr virus-derived vectors," *Proc. Natl. Acad. Sci. USA*, 96(9):5188-93, 1999.
Delecluse et al., "Propagation and recovery of intact, infectious Epstein-Barr virus from prokaryotic to human cells," *Proc. Natl. Acad. Sci. USA*, 95(14):8245-50, 1998.
Gaspar-Maia et al., "Open chromatin in pluripotency and reprogramming," *Nat. Rev. Mol. Cell Biol.*, 12(1):36-47, 2011.
Graf and Busslinger, "B Young Again," *Immunity*, 28:606-608, 2008.
Hanna et al., "Direct cell reprogramming is a stochastic process amenable to acceleration," *Nature*, 462:595-601, 2009.
Hanna et al., "Direct reprogramming of terminally differentiated mature B lymphocytes to pluripotency," *Cell*, 133:250-264, 2008.
Hettich et al., "Genetic design of an optimized packaging cell line for gene vectors transducing human B cells," *Gene Ther.*, 13(10):844-56, 2006.
Hong et al., "Suppression of induced pluripotent stem cell generation by the p53-p21 pathway," *Nature*, 460:1132-1135, 2009.
Jia et al. "A nonviral minicircle vector for deriving human iPS cells," *Nat. Methods*, 7(3):197-199, 2010.
Kanteti et al., "PAX5 is expressed in small-cell lung cancer and positively regulates c-Met transcription," *Lab Invest.*, 89(3):301-14, 2009.

(Continued)

*Primary Examiner* — Deborah Crouch
(74) *Attorney, Agent, or Firm* — Parker Highlander PLLC

(57) ABSTRACT

Methods and composition for providing induced pluripotent stem (iPS) cells are provided. For example, in certain aspects methods including reprogramming B lymphocytes transformed by episomal vectors such as Epstein-Barr virus-based vectors are described. Furthermore, the invention provides induced pluripotent stem cells essentially free of exogenous elements and having B cell immunoglobin variable region rearrangement.

12 Claims, 17 Drawing Sheets

(56) References Cited

OTHER PUBLICATIONS

Kennedy et al., "Epstein-Barr virus provides a survival factor to Burkitt's lymphomas," *Proc. Natl. Acad. Sci. USA*, 100:14269-14274, 2003.

Kira et al., "Anti-Epstein-Barr virus (EBV) activity of beta-L-5-iododioxolane uracil is dependent on EBV thymidine kinase," *Antimicrob. Agents Chemother.*, 44(12):3278-84, 2000.

Kirchmaier and Sugden, "Dominant-negative inhibitors of EBNA-1 of Epstein-Barr virus," *J. Virol.*, 71(3):1766-75, 1997.

Kuppers, "Clonotypic B cells in classic Hodgkin lymphoma," *Blood*, 114:3970-3971, 2009.

Leight and Sugden, "EBNA-1: a protein pivotal to latent infection by Epstein-Barr virus," *Rev. Med. Virol.*, 10(2):83-100, 2000.

Li et al., "Generation of rat and human induced pluripotent stem cells by combining genetic reprogramming and chemical inhibitors," *Cell Stem Cell*, 4:16-19, 2009.

Lin et al., "A chemical platform for improved induction of human iPSCs," *Nat. Methods*, 6(11):805-808, 2009.

Ludwig et al., "Derivation of human embryonic stem cells in defined conditions," *Nat. Biotechnol.*, 24(2):185-187, 2006.

Ludwig et al., "Feeder-independent culture of human embryonic stem cells," *Nat. Methods*, 3(8):637-46, 2006.

Mack and Sugden, "EBV is necessary for proliferation of dually infected primary effusion lymphoma cells," *Cancer Res.*, 68(17):6963-8, 2008.

Marie-Cardine et al., "Transitional B cells in humans: characterization and insight from B lymphocyte reconstitution after hematopoietic stem cell transplantation," *Clin. Immunol.*, 127(1):14-25, 2008.

Munsie et al., "Isolation of pluripotent embryonic stem cells from reprogrammed adult mouse somatic cell nuclei," *Curr. Biol.*, 10(16):98992, 2000.

Nanbo et al., "The coupling of synthesis and partitioning of EBV's plasmid replicon is revealed in live cells," *Embo J.*, 26:4252-62, 2007.

Okita and Yamanaka, "Induction of pluripotency by defined factors," *Exp. Cell Res.*, 316:2565-2570, 2010.

Okita et al., "Generation of mouse induced pluripotent stem cells without viral vectors," *Science*, 322:949-953, 2008.

Okita et al., "Generation of mouse-induced pluripotent stem cells with plasmid vectors," *Nat. Protoc.*, 5(3):418-428, 2010.

Parcells et al., "Recombinant Marek's disease virus (MDV)-derived lymphoblastoid cell lines: regulation of a marker gene within the context of the MDV genome," *J. Virol.*, 73(2):1362-1373, 1999.

Paschos et al., "Epstein-barn virus latency in B cells leads to epigenetic repression and CpG methylation of the tumour suppressor gene Bim," *PLoS Pathogens*, 5(6):e1000492, 2009.

Rahman et al., "Prednisolone sodium succinate down-regulates BSAP/Pax5 and causes a growth arrest in the Nalm6 pre-B cell line," *J. Exp. Med.*, 193(3):237-44, 2001.

Rajesh et al., "Human lymphoblastoid B-cell lines reprogrammed to EBV-free induced pluripotent stem cells," *Blood*, 118(7):1797-1800, 2011.

Sompallae et al., "Transcription profiling of Epstein-Barr virus nuclear antigen (EBNA)-1 expressing cells suggests targeting of chromatin remodeling complexes," *PLoS One*, 5:e12052, 2010.

Takahashi et al., "Induction of pluripotent stem cells from adult human fibroblasts by defined factors," *Cell*, 131(5):861-72, 2007.

Thorley-Lawson and Gross, "Persistence of the Epstein-Barr virus and the origins of associated lymphomas," *N. Engl. J. Med.*, 350:1328-1337, 2004.

U.S. Appl. No. 61/172,097 entitled "Reprogramming with Proteins" by Michael Miller, filed Apr. 23, 2009.

Utikal et al., "Immortalization eliminates a roadblock during cellular reprogramming into iPS cells," and Supplementary Information, *Nature*, 460:1145-1148, 2009. DOI:10.1038/nature08285.

van Dongen et al., "Design and standardization of PCR primers and protocols for detection of clonal immunoglobulin and T-cell receptor gene recombinations in suspect lymphoproliferations: report of the BIOMED-2 Concerted Action BMH4-CT98-3936," *Leukemia*, 17:2257-2317, 2003.

Wada et al., Successful differentiation to T cells, but unsuccessful B-cell generation, from B-cell-derived induced pluripotent stem cells, *Int. Immunol.*, 23(1):65-74, 2011.

Warren et al., "Highly efficient reprogramming to pluripotency and directed differentiation of human cells with synthetic modified mRNA," *Cell Stem Cell*, 7:618-630, 2010.

Wendtner et al., "High level of transgene expression in primary chronic lymphocytic leukemia cells using helper-virus-free recombinant Epstein-Barr virus vectors," *Exp. Hematol.*, 31(2):99-108, 2003.

Woltjen et al., "PiggyBac transposition reprograms fibroblasts to induced pluripotent stem cells," *Nature*, 458, 766-770, 2009.

Yamanaka, "Strategies and new developments in the generation of patient-specific pluripotent stem cells," *Cell Stem Cell*, 1(1):39-49, 2007.

Yu et al., "Human induced pluripotent stem cells free of vector and transgene sequences," *Science*, 324:797-801, 2009.

Yu et al., *Science*, "Induced pluripotent stem cell lines derived from human somatic cells," 318:1917-1920, 2007.

Zhou et al., "Generation of induced pluripotent stem cells using recombinant proteins," *Cell Stem Cell*, 4(5):381-384, 2009.

Zhou et al., "Novel mutant-selective EGFR kinase inhibitors against EGFR T790M," *Nature*, 462(7276):1070-4, 2009.

Kaji et al., "Virus free induction of pluripotency and subsequent excision of reprogramming factors," *Nature*, 458(7239):771-775, 2009.

PCT International Search Report and Written Opinion issued in International application No. PCT/US2011/046452, dated Mar. 15, 2012.

Polo et al., "Cell type of origin influences the molecular and functional properties of mouse induced pluripotent stem cells," *Nature Biotechnology*, 28(8):848-855, 2010.

Staerk et al., "Reprogramming of human peripheral blood cells to induced pluripotent stem cells," *Cell Stem Cell*, 7(1):20-24, 2010.

\* cited by examiner

REPROGRAMMING IMMORTALIZED B-CELLS TO INDUCED PLURIPOTENT STEM CELLS

This application claims priority to U.S. Application No. 61/370,615, filed on Aug. 4, 2010 and U.S. Application Ser. No. 61/441,885 filed on Feb. 11, 2011, the entire contents of which are hereby incorporated by reference.

BACKGROUND OF THE INVENTION

1. Field of the Invention

The present invention relates generally to the field of molecular biology and stem cells. More particularly, it concerns reprogramming of somatic cells, especially transformed B cells.

2. Description of Related Art

Induced pluripotent stem cells, commonly abbreviated as iPS cells or iPSCs, are a type of pluripotent stem cell artificially derived from a non-pluripotent cell, typically an adult somatic cell. Induced pluripotent stem cells are believed to be identical to natural pluripotent stem cells, such as embryonic stem (ES) cells in many respects, for example in terms of the expression of certain stem cell genes and proteins, chromatin methylation patterns, doubling time, embryoid body formation, teratoma formation, viable chimera formation, and potency and differentiability, but the full extent of their relation to natural pluripotent stem cells is still being assessed.

In humans, iPS cells are commonly generated from dermal fibroblasts. However, the requirement for skin biopsies and the need to expand fibroblast cells for several passages in vitro make it a cumbersome source for generating patient-specific stem cells. Moreover, previous methods for reprogramming of human somatic cells are inconvenient because they need to obtain somatic cells directly from a human subject, or maintain the cells in a labor-intensive cell culture system. Therefore, there is a need to develop methods to induce pluripotent stem cells from alternative sources which are simple, convenient, and easily accessible.

SUMMARY OF THE INVENTION

Generation of patient-specific induced pluripotent cells (iPSCs) holds great promise for regenerative medicine. Epstein-Barr virus (EBV) immortalized lymphoblastoid B cell lines (LCLs) can be generated from a minimal amount of blood and are banked worldwide as cellular reference material for immunological or genetic analysis for pedigreed study populations. As demonstrated in Examples, iPSCs were generated from two LCLs (LCL-iPSCs) via a feeder-free episomal method using a cocktail of transcription factors and small molecules. LCL-derived iPSCs exhibited normal karyotype, expressed pluripotency markers, lost oriP/EBNA-1 episomal vectors, generated teratomas, retained donor identity and differentiated in vitro into hematopoietic, cardiac, neural and hepatocyte lineages. Significantly, although the parental LCLs express viral EBNA-1 and other EBV latency related elements for their survival, their presence was not detectable in LCL-iPSCs. Thus, reprogramming LCLs could offer an unlimited source for patient-specific iPSCs especially for EBV related diseases.

Therefore, certain aspects of the present invention overcome a major deficiency in the art by providing novel methods for producing induced pluripotent stem cells (iPS cells) from immortalized somatic cells, as well as iPS cells provided therefrom. Accordingly, in a first embodiment there is provided a method that comprises reprogramming one or more somatic cells that have been immortalized by virtue of one or more episomal vector elements, therefore producing iPS cells. In certain aspects, the immortalized somatic cells comprise lymphoblastoid cells or immortalized peripheral blood mononuclear cells. An immortalized peripheral blood mononuclear cell may be derived from a lymphocyte (different types of T cells and/or B cells), a monocyte or a macrophage. For example, the immortalized somatic cells, in particular lymphoblastoid cells, may be derived from a cell population comprising B cells, for example, by EBV (Epstein-Barr virus) transformation. Any of the episomal vector elements disclosed herein may comprise EBV elements. The EBV elements may include an oriP replication origin and/or a gene encoding EBNA-1 or derivatives thereof.

In a particular aspect, there may be provided a method for producing induced pluripotent stem cells (iPS cells) from immortalized B cells. The method may comprise obtaining immortalized B cells that have been immortalized by virtue of one or more immortalizing Epstein-Barr virus (EBV) elements. The method may further comprise reprogramming the immortalized B cells by effecting expression of exogenous reprogramming factors therein, thereby producing iPS cells. It has been discovered that immortalizing EBV elements may not be required in iPS cells for long term proliferation and storage, therefore the method may further comprise removing the EBV elements from the iPS cells or isolating or enriching iPS cells that are essentially free of the EBV elements. Thus, iPS cells essentially free of EBV elements but derived from immortalized B cells may be obtained.

There may be at least two approaches to obtain immortalized B cells. One approach may be to immortalize B cells with Epstein-Barr virus (EBV) elements. Such B cells prior to immortalization may have been obtained from a blood sample. The blood sample may have a volume of from at least about 0.01 to about 5 mL, more particularly about 0.1 to 0.5 mL, or any number or range derivable therein. For example, the immortalizing EBV elements may comprise inducible exogenous reprogramming expression cassettes. Thus, reprogramming the immortalized B cells may comprise inducing the expression of inducible exogenous reprogramming expression cassettes. In other aspects, the immortalized B cells may be obtained from an established lymphoblastoid cell line. For reprogramming, the method may comprise introducing one or more reprogramming episomal vector elements into the immortalized B cells, such as EBV elements.

To increase reprogramming efficiency, the immortalized B cells may be cultured in the absence of a feeder layer. In further aspects, the method may comprise contacting the immortalized B cells with one or more signaling inhibitors including a glycogen synthase kinase 3 (GSK-3) inhibitor, a mitogen-activated protein kinase kinase (MEK) inhibitor, a transforming growth factor beta (TGF-β) receptor inhibitor, leukemia inhibitory factor (LIF), a p53 inhibitor, an NF-kappa B inhibitor, or a combination thereof. The reprogramming method may also comprise contacting the immortalized B cells with fibroblast growth factor (FGF). The reprogramming method as described in certain aspects of the invention may obviate the need of Pax-5 inhibition or C/EBPα overexpression in repreogramming mature B cells. Thus, the reprogramming may not include the introduction of an inhibitory nucleotide specific for Pax-5 into the immortalized B cells or expression of exogenous C/EBPα in the immortalized B cells. The method may further comprise differentiating the iPS cells into cardiac cells, hematopoietic cells, neural cells, or hepatocytes in vitro.

For reprogramming B cells to produce iPS cells, there may be provided a method of immortalizing B cells, and effecting exogenous expression of one or more reprogramming factors in the immortalized B cells. In a further embodiment, there may also be provided a method for producing iPS cells, comprising the steps of: a) transforming B cells with an EBV-based episomal vector to produce an immortalized cell line; and b) effecting exogenous expression of one or more reprogramming factors in the immortalized cell line, thereby producing iPS cells.

Reprogramming of immortalized B cells may comprise introducing reprogramming episomal vectors into the immortalized B cells. In alternative embodiments, reprogramming may comprise inducing the expression of reprogramming expression cassettes comprised in the episomal vectors for immortalization. The reprogramming factors may be reprogramming expression cassettes comprised in a separate episomal vector different from the EBV-based episomal vector for immortalization. Alternatively, the reprogramming factors may be reprogramming expression cassettes comprised in the EBV-based episomal vector, therefore saving the step of introducing separate reprogramming vectors and simplifying the process. The reprogramming expression cassettes may be under the control of an inducible promoter. In this particular aspect, effecting exogenous expression of reprogramming factors may comprise activating the inducible promoter.

As described below, there may be provided methods comprising isolating or enriching iPS cells that are essentially free of episomal vector elements (episomal vector elements for immortalization or reprogramming or both) or removing episomal vector elements from iPS cells so produced. Episomal vector elements for immortalization or reprogramming may be the same or different entities.

Certain aspects of the invention are novel at least because the initial immortalized cells depend on genes expressed by episomal vector elements for long-term proliferation to provide a sustained cell source; however, after converting into iPS cells, the episomal vector elements are no longer needed as the iPS cells are naturally proliferative and immortal. Therefore, in certain embodiments, the iPS cells so produced may be essentially free of exogenous genetic elements, particularly episomal vector elements: for example, the iPS cells may be essentially free of DNA, RNA or protein of EBNA-1, EBV latency-related elements such as EBNA-2, LMP-2A, lytic gene such as BZLF-1, and/or EBV-encoded small RNAs (EBERs).

Such iPS cells may be produced with or without additional steps for enriching or selecting cells essentially free of episomal vector elements during or after reprogramming. For example, enriching or selecting the iPS cell essentially free of episomal vector elements may include having the episomal vector elements removed to minimize the effects of exogenous genetic elements. In other aspects, the episomal vector elements may be lost from iPS progeny cells after long term proliferation.

In one embodiment, there may be methods comprising isolating or enriching the iPS cells that are essentially free of episomal vector elements. For example, the method may comprise cloning individual iPS cells and selecting for a clonal colony that has the episomal vector elements removed. To facilitate the selection, the method may comprise effecting expression of a selectable marker and/or screenable marker comprised in the episomal vector elements. In some aspects, the selectable and/or screenable marker is under the control of an externally responsive regulatory element, such as an inducible promoter. An inducing agent, such as estrogen or tetracycline, may effect expression of such a selectable and/or screenable marker, which indicates the presence of the episomal vector elements.

A selectable marker and/or screenable marker may be used in certain aspects of the invention for various purposes. Any selectable or screenable marker known in the art are included. The selectable maker may be further defined as an antibiotic resistance gene or a suicide gene. The screenable marker may be further defined as a reporter gene that expresses a fluorescent, luminescent or bioluminescent protein or a reporter gene that expresses a cell surface marker, an epitope, or chloramphenicol acetyl transferase (CAT). For example, the antibiotic resistance gene may be a gene that confers resistance to puromycin, blasticidin, neomycin, tetracycline, or ampicillin. The suicide gene may be Herpes simplex virus thymidine kinase gene (HSV-tk). The reporter gene may express a protein such as a green fluorescent protein (GFP), red fluorescent protein (RFP), blue fluorescent protein (BFP), yellow fluorescent protein (YFP), luciferase or beta-galactosidase.

In another embodiment, the episomal vector elements in the iPS cells may be removed by methods comprising effecting expression of an episomal mutant gene that increases the loss of the episomal vector elements from the iPS cells. For example, the episomal mutant gene is an EBNA-1 (Epstein-Barr virus nuclear antigen 1) dominant negative mutant. For example, EBNA-1 dominant negative mutants may be derivatives of EBNA-1 such as ND450-641 and ND450-618 (Kirchmaier and Sugden, 1997).

In certain aspects, the method comprises introducing an expression cassette comprising the episomal mutant gene into the iPS cells. In other aspects, the method may comprise effecting the expression of the episomal mutant gene comprised in the episomal vector elements. For example, the episomal mutant gene may be under the control of an inducible promoter. The method may comprise activating such a promoter when the episomal removal is desired, thereby the episomal mutant gene would be expressed.

In a further embodiment, the episomal vector elements in the iPS cells may be removed by methods comprising contacting the iPS cells with one or more agents capable of removing the episomal vector elements. Particularly, the episomal vector elements comprise viral elements, for example, EBV elements. The removal agents may be anti-viral agents, or more particularly, anti-EBV agents. Without being bound by theory, the anti-viral agents or anti-EBV agents may inhibit replication or proliferation of episomal vector elements; or in other aspects, because the episomal vector elements may be spontaneously lost from iPS cells with cell growth/division, some examples of these agents may specifically inhibit or kill cells which still retain the vector elements, thereby enriching cells essentially free of the vector elements.

For example, the anti-viral agents comprise nucleic acid analogs or G-quadruplex-specific compounds. Nucleic acid analogs may be Acyclovir ([9-(2-hydroxyethoxymethyl)guanine]), E-5-(2-bromovinyl)-2'-deoxyuridine, 1-(2-deoxy-2-fluoro-beta-D-arabinofuranosyl)-5-iodocytosine, 1-(2-deoxy-2-fluoro-beta-D-arabinofuranosyl)-5-methyluracil, beta-L-5-Iododioxolane uracil, and/or 3'-azido-3'-deoxythymidine. G-quadruplex-specific compounds may be TMPyP3, TMPyP4, and/or BRACO-19.

For example, the anti-EBV agents may comprise Hsp90 inhibitors, c-Myc inhibitors, or EBNA-1 inhibitors. The EBNA-1 inhibitor may be further defined as a fusion protein comprising a protein transduction domain fused to an EBNA-1 mutant protein that increases the loss of the EBV vector elements. A particular example of the fusion protein may be a derivative of EBNA-1 that functions dominant-negatively fused to the Tat protein to facilitate protein transduction.

As describe above, the immortalized somatic cells may be lymphoblastoid cells derived from a cell population comprising B cells. The B cells may have been immortalized by EBV transformation. The cell population may comprise immature B cells. In a further aspect, the cell population may comprise mature B cells. The B cell-containing cell population may be obtained from a source such as a blood sample, blood components, bone marrow, lymph node, spleen, fetal liver, or umbilical cord. The source may be of a selected subject or a selected population. The somatic cells may be from a subject having a selected disease or disorder, for example, a patient having an EBV infection or a patient in need of transplantation.

The method may further comprise obtaining B cells from any B cell-containing source, such as a blood sample. Due to the high reprogramming efficiency of the present method and high proliferation capacity of immortalized cells, the iPS cell production methods may involve the use of a unprecedentedly small amount of blood sample from a selected subject, for example, at least, about, or at most 0.001, 0.002, 0.003, 0.004, 0.005, 0.006, 0.007, 0.008, 0.009, 0.01, 0.02, 0.03, 0.04, 0.06, 0.07, 0.08, 0.09, 0.1, 0.2, 0.2, 0.3, 0.4, 0.5, 0.6, 0.7, 0.8, 0.9, 1, 1.5, 2, 2.5, 3, 4, 5, 6, 7, 8, 9, 10 mL, or any range derivable therein. The method may also include selecting a subject, particularly a patient. The selected subject or patient may have a selected genetic marker.

In certain aspects, the iPS cells may be produced or the reprogramming may comprise culturing cells in the presence of a feeder layer, such as mouse embryonic fibroblast (MEF) cells. In other aspects, as the presence of MEFs may result in uncontrolled proliferation of undesired cells, it may be advantageous to reprogram in the absence of a feeder layer. For example, iPS cells may be produced in the presence of a matrix component. The matrix component may comprise Matrigel™, fibronectin, RetroNectin® (a fragment of fibronectin), CellStart™, collagen or any component that could replace a feeder layer.

In further aspects, the invention involves reprogramming the immortalized somatic cells. For example, reprogramming may comprise effecting the expression of one or more reprogramming factors in the cells, for example, the reprogramming factors may be reprogramming expression cassettes comprises in the immortalizing episomal vector elements; and/or introducing one or more reprogramming factors into the cells, for example, via additional episomal vector elements.

Reprogramming factors may effect the expression of Sox and Oct, for example, by using ectopic expression or protein transduction. Sox and Oct are thought to be central to the transcriptional regulatory hierarchy that specifies ES cell identity. For example, Sox may be Sox1, Sox2, Sox3, Sox15, or Sox18, preferably Sox2; Oct may be Oct4. Additional factors may increase the reprogramming efficiency, like Nanog, Lin28, Klf, c-Myc, L-Myc, SV40 Large T antigen, or Esrrb. Specific sets of reprogramming factors may be a set comprising Sox2, Oct4, Nanog and, optionally, Lin-28; or comprising Sox2, Oct4, Klf and, optionally, c-Myc; or Sox2, Oct4, Nanog and, SV40 Large T antigen.

In a particular aspect, the episomal vector elements for immortalization may comprise one or more reprogramming expression cassettes comprising an Oct gene and a Sox gene. The reprogramming expression cassettes may further comprise a Nanog gene, a Lin28 gene, a Klf gene, a Myc gene, or an SV40 large T antigen gene. The reprogramming expression cassettes may be under the control of an externally controllable regulatory element, such as an inducible promoter or a conditional operator. This aspect may save the step of introducing reprogramming factors after immortalization. A Myc gene may be a c-Myc, N-Myc, or L-Myc.

In other aspects, the reprogramming factors may comprise one or more reprogramming expression cassettes comprising an Oct gene and a Sox gene. The reprogramming expression cassettes may further comprise a Nanog gene, a Lin28 gene, or a Klf gene.

For direct reprogramming, the reprogramming factors may comprise one or more reprogramming proteins comprising a Sox protein and an Oct protein. The reprogramming proteins may further comprise a Nanog protein, a Lin28 protein, a Klf protein, a Myc protein, or an SV40 large T antigen protein. To assist the intracellular delivery, the reprogramming proteins may be operably linked to a protein transduction domain.

For enhancement of reprogramming, reprogramming may further comprise contacting the cells with one or more cell signaling regulators, such as a glycogen synthase kinase 3 (GSK-3) inhibitor, a mitogen-activated protein kinase kinase (MEK) inhibitor, a transforming growth factor beta (TGF-$\beta$) receptor inhibitor, leukemia inhibitory factor (LIF), a p53 inhibitor, an NF-kappa B inhibitor, or a combination thereof. Those regulators may include small molecules, inhibitory nucleotides, expression cassettes or protein factors. In particular aspects, reprogramming of immortalized mature B cells may comprise reprogramming in the presence of a combination of signaling inhibitors, while obviating the use of a Pax-5 inhibitory nucleotide molecule and exogenous expression of C/EBP$\alpha$.

For reprogramming immortalized cells derived from B cells, especially mature B cells, B cell development regulators such as a C/EBP$\alpha$ enhancer and/or a Pax-5 inhibitor may or may not be used in reprogramming. An important finding is that preemptive inhibition of Pax-5 is not required to reprogram LCLs. It automatically is inhibited/down-regulated during the reprogramming process but it is not necessary to preemptively down regulate it for reprogramming to occur. Therefore, externally added Pax-5 inhibitors or C/EBP$\alpha$ enhancer (C/EBP$\alpha$ down-regulates Pax-5) may not be used prior to or during reprogramming of immortalized B cells.

For example, the Pax-5 inhibitor may be any inhibitory nucleotide, such as antisense RNA, small interfering RNA, ribozymes, or an expression cassette expressing Pax-5 inhibiting nucleotide molecules. The Pax-5 inhibitor may also be a glucocorticoid like Prednisolone sodium succinate, SN38, or SU11274 to down-regulate Pax-5 expression. Glucocorticoids have also been described in the literature to induce the expression of C/EBP$\alpha$. Similarly, B cell development regulators may also include inhibitors of Blimp1, Oct2 and Bob-1, which may or may not be used in reprogramming of B cells.

Overexpression of C/EBP$\alpha$ may be achieved through an expression cassette for expressing C/EBP$\alpha$ or induced by small molecule treatment. It has also been reported that C/EBP$\alpha$ may directly or indirectly (through EBF) downregulate Pax-5, although the exact mechanism is not currently known.

Nucleotides of these B cell development regulators such as C/EBP$\alpha$ enhancer and/or a Pax-5 inhibitor may be comprised in the episomal vector elements and may be removed after pluripotency has been established.

In alternative embodiments, reprogramming of lymphoblastoid cells or immortalized B cells may be performed without the use of Pax-5-specific inhibitory nucleotides and/or exogenous expression of C/EBP$\alpha$.

In accordance with any of the above methods, certain aspects of the invention may provide an iPS cell or a differentiated cell, tissue, or organ derived therefrom. For clinical application or research of the iPS cells, the methods may further comprise differentiating the iPS cells to a differentiated cell, for example, a cardiomyocyte, a hematopoietic cell, a myocyte, a neuron, a fibroblast, a pancreatic cell, a hepatocyte, or an epidermal cell. In a further aspect, a differentiated cell, tissue or organ, which has been differentiated from the iPS cell population as described above, may be disclosed. The tissue may comprise nerve, bone, gut, epithelium, muscle, cartilage or cardiac tissue; the organ may comprise brain, spinal cord, heart, liver, kidney, stomach, intestine or pancreas. In certain aspects, the iPS cells and differentiated cell, tissue or organ may be used in tissue transplantation, drug screening or developmental research to replace embryonic stem cells.

There may also be provided an iPS cell comprising a genome comprising an incomplete set of V, D, and J segments of immunoglobulin variable region genes compared with an embryonic stem cell, which may be a human cell. In a particular aspect, the iPS cell may be essentially free of integrated, exogenous viral elements. In a further aspect, the iPS cell may be essentially free of episomal vector elements. In a yet further aspect, the iPS cell may be essentially free of any exogenous genetic elements. In a particular aspect, there may be provided a human iPS cell having a genome that comprises an incomplete set of B cell immunoglobin variable region genes compared with an embryonic stem cell. The iPS cell may be essentially free of exogenous genetic elements or EBV elements. The genome of the iPS cell may comprise a selected genetic marker, such as a genetic marker of a selected disease, like a particular cancer, acquired immunodeficiency syndrome (AIDS) or Human immunodeficiency virus (HIV) infection or a neurological disease. In a particular aspect, the genome of the IPS cell may be derived from an immortalized B cell. In certain aspects, the iPS cell may or may not have a normal karyotype. There may also be provided a differentiated cell, tissue, or organ derived from the iPS cell.

In a still further aspect, an iPS cell that comprises a genome derived from a somatic cell that has been immortalized by virtue of one or more episomal vector elements may also be disclosed. Such immortalized cell may be a lymphoblastoid cell. In particular, the iPS cell may be essentially free of episomal vector elements.

There may also be provided an iPS cell that comprises a genome comprising an incomplete set of B cell immunoglobin variable region genes compared with an embryonic stem cell, wherein the iPS cells is essentially free of exogenous genetic elements. The genome may comprise a selected genetic marker, such as a genetic marker of a selected disease. Such iPS cells may be immortal, have a normal karyotype, no exogenously introduced oncogenes or telomerase, and a B cell rearrangement, and/or carry a specific genetic marker for one or more diseases. Any differentiated derivatives from such iPS cells may also be provided.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A: Pax-5 isotype control. Representatitve flow cytometic staining of LCL-2 cells with PE conjugated Pax-5 antibody isotype control. The background staining is approximately 0.4%. FIG. 6B: Pax-5 of LCL-1 untransfected cells. Representatitve flow cytometic staining of LCL-2 post transfection control (with no DNA) with PE conjugated Pax-5. The Pax-5 expression staining is approximately 56.2%. FIG. 6C: Pax-5 staining of LCL-2 cells transfected with reprogramming factors. Representative flow cytometic staining of LCL-2 cells transfected with reprogramming plasmids p36-p34-p31 with PE conjugated Pax-5 antibody. The Pax-5 expression staining is approximately 8.2%. FIG. 6D: Pax-5 inhibition by reprogramming factors. Levels of Pax-5 inhibition of LCL-1 and LCL-2 cell lines transfected with various combinations of reprogramming plasmids.

FIG. 7A: The scheme for reprogramming human lymphoblastoid cell lines (LCLs). Morphology of a LCL culture, cells during reprogramming and LCL-iPSC colonies are shown. Images were captured using 40×, 20× and 10× magnification, respectively. FIG. 7B: The average number of Tra-1-60 positive colonies form after nucleofection of LCL-1 (i) and LCL-2 (ii) with various combinations of reprogramming factors. The abbreviations used for the reprogramming factors are as follows: O=OCT4, S=SOX2, N=NANOG, K=KLF4, c-m=c-MYC, L-m=L-MYC, T=SV40 Large T antigen and L=LIN28. FIG. 7C: Characterization of LCL-iPS lines. i. Brightfield (left panel) and Tra-1-60 staining (right panel) of a representative LCL-derived iPS line (LCL-iPS2a), confirms uniform expression of the pluripotent surface marker, Tra-1-60. Images were taken using 10× magnification. ii. Flow cytometric analysis of hESC pluripotency markers OCT4 (left panel, OCT4: black line and isotype control: red line), SSEA-4 (middle panel, SSEA4: red line and isotype control: black line) and Tra-1-81 (right panel, Tra-1-81: red line and isotype control: black line) of a representative LCL derived iPS line,LCL-iPS1b. iii. Karyotype analysis of each LCL-iPS line was performed after 11 passages (WiCell Research Institute) and found to be normal; a representative image of LCL-iPS2b is shown. iv. RT-PCR analysis of H1 (hESC line), LCL-1, LCL-2 and two representative LCL-iPS clones from each donor lines for expression of hES cell-marker genes DNMT3B, LEFTB, NODAL, REX1, ESG1, GDF3, and UTF1. GAPDH was used as positive loading control for each sample and cDNA made in the absence of reverse transcriptase (no RT) was used to verify genomic DNA did not contaminate the RNA samples. FIG. 7D: Hematoxylin and eosin (H&E) staining of teratomas derived from immunodeficient mice injected with LCL-iPS2a show tissues representing all three embryonic germ layers, endoderm (goblet cells, left panel), ectoderm (neural rosettes, middle panel) and mesoderm (cartilage, right panel). All H&E images were captured using 40× magnification. FIG. 7E: RT-PCR analysis of RNA from LCL-iPSCs for the expression of reprogramming vector genes. Forward primers for three reprogramming genes of interest (OCT4, NANOG and c-Myc) and reverse primers for IRES2 were utilized. GAPDH was used as a positive loading control for each sample and cDNA made in the absence of Reverse Transcriptase (no RT) was used to verify genomic DNA did not contaminate the RNA samples. A reprogramming vector was included as a positive control for each PCR reaction (+ control). FIG. 7F: PCR analysis of genomic DNA confirms no integration of the transgenes. Forward primers for three reprogramming genes of interest (OCT4, NANOG and c-Myc) and reverse primers for the IRES were utilized. GAPDH was used as a positive loading control for each sample and a reprogramming vector was included as a positive control for each PCR reaction (+ control).

FIG. 8A: RT-PCR analysis of H1 (hESC line), LCL-1, LCL-2 and two representative LCL-iPS clones from each donor line for expression of EBV genes: EBNA-1, EBNA-2, LMP-2A and BZLF-1. GAPDH was used as positive loading control for each sample and cDNA made in the absence of Reverse Transcriptase (no RT) was used to verify genomic DNA did not contaminate the RNA samples. FIG. 8B: PCR analysis of genomic DNA (gDNA) reveals an absence of EBV DNA in LCL-iPSCs. gDNA PCR analysis of H1 (hESC line), LCL-1, LCL-2 and two representative LCL-iPSCs from each donor line was performed to detect EBV sequences encoding: EBNA-1, oriP, EBNA-2 and BZLF-1. GAPDH was used as a positive loading control for each sample. FIG. 8C: Immunohistochemistry was performed on LCL-1, LCL-2 and two representative LCL-iPS clones from each donor line using an anti-EBNA-1 antibody to detect EBNA-1 protein expression (brown). Images were captured using 40× magnification. FIG. 8D: Trilineage in vitro differentiation. i. Quantification of alphal-antitrypsin expressing hepatocyte precursors derived from LCL-iPSCs by flow cytometry. ii. Cardiac induction of LCL-iPSCs was performed and quantification of cardiac troponin T (cTNT)-positive cardiomyocytes at day 14 by flow cytometry. iii. Neural cultures from LCL-iPS2b immunostained for the presence of β3-tubulin. Image captured using 20× magnification. iv. Quantification of β3-tubulin and nestin co-expressing neural precursors from neural induced LCL-iPSCs by flow cytometry. v. Megacult cultures of HPCs derived from LCL-iPS2a cells stained for the presence of megakaryocytes and proplatelets, image captured at 40× magnification (left panel). HPCs derived LCL-iPS2b expanded in the presence of GM-CSF and stained for the presence of monocytes, neutrophils and macrophages, image captured at 20× magnification (right panel). vi. Quantification of Colony Forming Units (CFU) to demonstrate the presence of erythroid (CFU-E/BFU-E), myeloid comprising macrophage (CFU-M), granulocyte (CFU-G), and granulocyte-macrophage (CFU-GM), and multipotent comprising granulocyte-erythroid-macrophage-megakaryocyte (CFU-GEMM) colonies from all four LCL-iPSCs. vii. In vitro differentiation into LCL-iPSCs to cells to hematopoietic progenitor cells (HPCs) via a defined serum-free embryoid body (EB) differentiation protocol for 12 days. The percentage of single positive CD34, CD45, CD43, CD41, CD235a and double positive CD34/CD43, CD45/CD43, CD34/45 cells was quantified by flow cytometry. FIG. 8E: Each B-cell has a single productive immunoglobulin gene rearrangement respectively that is unique in both length and sequence. Polymerase chain reaction (PCR) assays with specific primers for the joining region and all three of the conserved framework regions (FR1, FR2 and FR3) were used to amplify immunoglobulin heavy chain (IgGH) gene rearrangements according to the BIOMED-2 Concerted Action protocol. DNA from a normal or polyclonal B cell population produces a bell-shaped curve of amplicon products (Gaussian distribution), whereas clonal rearrangements are identified as prominent, single-sized products by capillary electrophoresis and GeneScanning.

DESCRIPTION OF ILLUSTRATIVE EMBODIMENTS

I. Introduction

Figure 1A:
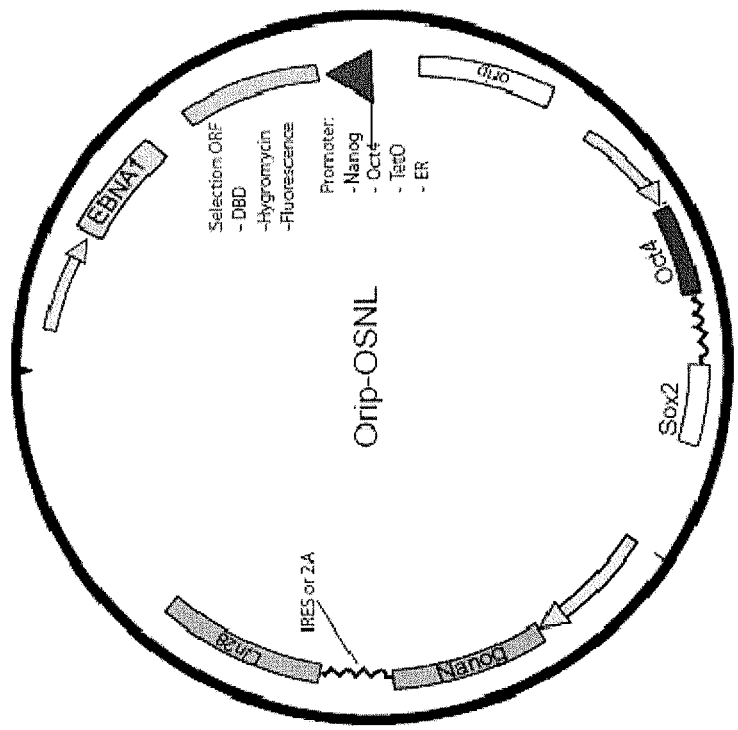
FIGS. 1A-1B: Exemplary EBV-based episomal vectors having reprogramming expression cassettes.

Patient-specific induced pluripotent stem cells (iPSCs) can serve as a useful model to understand the etiology of disease and facilitate the development of novel therapeutic interventions (Yamanaka, 2007). Recently, iPSCs free of exogenous DNA have been generated by delivering reprogramming factors via multiple methods including oriP/EBNA-1 (Epstein-Barr nuclear antigen-1) based episomal plasmids (Yu et al., 2009) in the presence or absence of small molecules (Lin et al., 2009; Okita and Yamanaka, 2010; Okita et al., 2010), via piggyBAC transposons (Woltjen et al., 2009), minicircles (Jia et al., 2010), proteins (Zhou et al., 2009) or by a cocktail of RNAs (Warren et al., 2010) predominantly using fibroblasts. However, these methods still have relatively low reprogramming efficiency and are thus limited in applications.

Peripheral blood is a more tractable source for reprogramming compared with fibroblasts derived from invasive skin biopsies. Human B cells from as little as 0.5 mL blood can be transformed in vitro by EBV to generate lymphoblastoid cell lines (LCLs) (Amoli et al., 2008). A number of major facilities currently manage collections of LCLs for the international research community (Amoli et al., 2008). B lymphocytes can transdifferentiate to macrophages (Cobaleda, 2010; Cobaleda and Busslinger, 2008) or hematopoietic precursor cells (HPCs) by down-regulation of Pax-5 expression (Cobaleda and Busslinger, 2008). Murine B cells have been reprogrammed to generate iPSCs via viral transduction of OCT3/4, SOX2, KLF4, and c-MYC in the presence (Hanna et al., 2008) or absence of Pax-5 inhibition (Wada et al., 2011).

Certain aspects of the present invention provide a method for preparing iPS cells by reprogramming of somatic cells, particularly somatic cells immortalized by virtue of episomal vector elements. For example, reprogramming of lymphoblastoid cells (e.g., EBV-transformed B cells) and iPS cells derived therefrom are included. Immortalized somatic cells, such as lymphoblastoid cells, may depend on episomal vector elements for long-term proliferation; however, after reprogramming to an established pluripotent state, the reprogrammed cells have a normal karyotype and are no longer dependent on the episomal vector elements, particularly EBV expressed genes, for their proliferation. Such immortalized cells may include any lymphoblastoid cell lines already available or in storage, or immortalized cells derived from a specific living subject.

Generating pluripotent or multipotent cells by somatic cell reprogramming using the methods of the present invention has at least the following advantages. First, the methods of the present invention allow one to generate autologous pluripotent cells, which are cells specific to a patient. The use of autologous cells in cell therapy offers a major advantage over the use of non-autologous cells, which are likely to be subject to immunological rejection. In contrast, autologous cells are unlikely to elicit significant immunological responses (See Munsie et al., 2000). Second, the methods of the present invention allow one to generate pluripotent cells from a novel sustainable and easy source of immortalized somatic cells without using embryos, oocytes and/or nuclear transfer technology. Not intended to limit the scope, the present invention involves reprogramming of immortalized cells such as EBV-transformed B cells, but not B cells directly from a subject, therefore reducing the volume of a sample such as a blood sample needed for reprogramming.

The inherent plasticity of B cells, their receptivity to oriP/EBNA-1 plasmids, ease of generating LCLs, and availability of banked collections of LCLs may be additional advantages for reprogramming immortalized B cells or LCLs using oriP/EBNA-1 based episomal vectors. As shown in Examples, LCL-derived iPSCs demonstrated the characteristics of pluripotent stem cells with a normal karyotype, retained the genetic identity of the parental LCLs, maintained the clonal signature of the rearranged IgG locus and lost expression of the episomal reprogramming genes as well as viral EBNA-1, EBNA-2, LMP-2A and BZLF-1 genes, leading to self-sustained LCL-iPSCs essentially free of exogenous reprogramming and viral elements.

In additional aspects, the resulting iPS cells provided may have the episomal vector elements removed or lost during cell division to minimize the effect of such exogenous elements. Therefore, an immortal cell with a normal karyotype, no exogenously introduced oncogenes or telomerase, and optionally carrying a specific genetic marker for a disease may be provided. Until this invention, it is highly unlikely that the existing EBV transformed B-cell lines would be utilized to study a genetic predisposition for a particular disease with the EBV viral genes still present, as that would likely interfere with or confound the results when specific tissues are generated and studied. However, by removing those episomal elements, the resulting iPS cells generated from the B cell lines would be useful for the purpose of studying a particular disease in specific cells or tissues derived from the iPS cells.

In further aspects, somatic cells from a living subject may be obtained for immortalization by episomal vector elements followed by reprogramming into iPS cells. For example, a cell population comprising B cells from a small volume of blood may be transformed with EBV and then the transformed B cells may undergo reprogramming. In particular aspects, the episomal vector elements, like the EBV vectors, may comprise inducible reprogramming expression cassettes. Therefore, as an alternative to introducing reprogramming factors into immortalized cells, the reprogramming cassettes in the episomal vector in the immortalized cells may be induced for reprogramming.

Some aspects of the invention provide methods of reprogramming transformed B cells and provide iPS cells derived from such B cells. In a further aspect, these iPS cells may be essentially free of exogenously integrated genetic elements. A particular advantage of these aspects lies in rearranged and reduced V, D, J gene segments of immunoglobulin genes from B cells which may be retained in reprogrammed progeny cells and the absence of integration of foreign genes. This could serve as a specific characteristic or "bar code" of different clonal populations of B cell-derived iPS cells, and also help to differentiate those iPS cells from pluripotent stem cells which have not undergone V(D)J recombination. The absence of genetic integration is important for the future use of iPS cells without the risks of oncogenic transformation and of developing dysfunction, etc. Further embodiments and advantages of the invention are described below.

"Reprogramming" is a process that confers on a cell a measurably increased capacity to form progeny of at least one new cell type, either in culture or in vivo, than it would have under the same conditions without reprogramming. More specifically, reprogramming is a process that confers on a somatic cell a pluripotent potential. This means that after sufficient proliferation, a measurable proportion of progeny have the phenotypic characteristics of the new cell type if essentially no such progeny could form before reprogramming; otherwise, the proportion having characteristics of the new cell type is measurably more than before reprogramming. Under certain conditions, the proportion of progeny with characteristics of the new cell type may be at least about 1%, 5%, 25% or more in order of increasing preference.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from viral, prokaryotic or eukaryotic mRNA, genomic DNA sequences from viral, prokaryotic or eukaryotic DNA, and synthetic DNA sequences. A transcription termination sequence will usually be located 3' to the gene sequence.

The term "cell" is herein used in its broadest sense in the art and refers to a living body which is a structural unit of tissue of a multicellular organism, is surrounded by a membrane structure which isolates it from the outside, has the capability of self replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell that is capable of self-renewal through mitotic cell division and differentiation into a diverse range of specialized cell types (i.e., pluripotent). Typically, stem cells can regenerate an injured tissue. Stem cells herein may be, but are not limited to, embryonic stem (ES) cells, induced pluripotent stem (iPS) cells, or tissue stem cells (also called tissue-specific stem cell, or somatic stem cell). Any artificially produced cell which can have the above-described abilities (e.g., fusion cells, reprogrammed cells, or the like used herein) may be a stem cell.

"Embryonic stem (ES) cells" are pluripotent stem cells derived from early embryos. An ES cell was first established in 1981, which has also been applied to production of knock-out mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

"Induced pluripotent stem cells," commonly abbreviated as iPS cells or iPSCs, refer to a stem cell having properties similar to those of an ES cell, and specifically a cell having pluripotency and proliferative capacity. An iPS cell is artificially prepared from a non-pluripotent cell, typically an adult somatic cell or terminally differentiated cell, such as a fibroblast, a hematopoietic cell, a myocyte, a neuron, an epidermal cell, or the like, by effecting exogenous expression of certain genes referred to as reprogramming factors.

"Pluripotency" refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). "Pluripotent stem cells" used herein refer to cells that can differentiate into cells derived from any of the three germ layers, for example, direct descendants of totipotent cells or induced pluripotent cells.

The term "somatic cell" refers to any cell except an ES cell, an iPS cell, or other cells which retain their undifferentiated, pluripotent state. Specific examples of somatic cells include, for example, (i) tissue stem cells (somatic stem cells), such as neural stem cells, hematopoietic stem cells, mesenchymal stem cells and the like, (ii) tissue progenitor cells, and (iii) differentiated cells, such as lymphocytes, epithelial cells, muscle cells, fibroblasts and the like. The kind of the somatic cell used for the preparation method of the present invention is not particularly limited and any somatic cell can be suitably used.

A "vector" or "construct" (sometimes referred to as gene delivery or gene transfer "vehicle" or "cassette") refers to a macromolecule or complex of molecules comprising a polynucleotide to be delivered to a host cell, either in vitro or in vivo. A vector can be a linear or a circular molecule.

The term "episomal vector" refers to an extra-chromosomal DNA molecule which autonomously replicates and maintains itself. In certain cases, it is circular and double-stranded. Any episomal vector that has such properties can be used for the preparation method of the present invention, without particular limitation.

By "expression construct" or "expression cassette" is meant a nucleic acid molecule that is capable of directing transcription. An expression construct includes, at the least, a promoter or a structure functionally equivalent to a promoter. Additional elements, such as an enhancer, and/or a transcription termination signal, may also be included.

The term "exogenous," when used in relation to a protein, gene, nucleic acid, or polynucleotide in a cell or organism refers to a protein, gene, nucleic acid, or polynucleotide which has been introduced into the cell or organism by artificial or natural means, or in relation to a cell refers to a cell which was isolated and subsequently introduced to other cells or to an organism by artificial or natural means. An exogenous nucleic acid may be from a different organism or cell, or it may be one or more additional copies of a nucleic acid which occurs naturally within the organism or cell. An exogenous cell may be from a different organism, or it may be from the same organism. By way of a non-limiting example, an exogenous nucleic acid is in a chromosomal location different from that of natural cells, or is otherwise flanked by a different nucleic acid sequence than that found in nature.

By "operably linked" with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. "Operably linked" with reference to peptide and/or polypeptide molecules is meant that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

The term "regulatory elements" refers collectively to promoter regions, polyadenylation signals, transcription termination sequences, upstream regulatory domains, origins of replication, internal ribosome entry sites ("IRES"), enhancers, splice junctions, and the like, which collectively provide for the replication, transcription, post-transcriptional processing and translation of a coding sequence in a recipient cell. Not all of these control elements need always be present so long as the selected coding sequence is capable of being replicated, transcribed and translated in an appropriate host cell.

The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3' direction) coding sequence.

By "enhancer" is meant a nucleic acid sequence that, when positioned proximate to a promoter, confers increased transcription activity relative to the transcription activity resulting from the promoter in the absence of the enhancer domain.

II. Sources of Cells for Reprogramming

The medical potential of cellular reprogramming for regenerative medicine is enormous, and hence efforts are ongoing to identify the ideal cell type that exhibits plasticity with a minimal amount of manipulation. Certain aspects of the invention provide methods and cells used for reprogramming somatic cells (e.g., blood cells, more particularly, B cells) immortalized by the virtue of episomal vector elements, particularly EBV elements. The cells to be reprogrammed may be lymphoblastoid cells, for example, EBV-transformed B cells, either established or derived from a blood sample. The source of B cells may be a small blood sample from a living or diseased subject, for example, a human.

Blood is a convenient and accessible source of human material amenable to reprogramming to generate induced, pluripotent stem (iPS) cells. Multiple labs have successfully derived iPS cells from cord blood, for example. More specifically, iPS cells have been generated from T cells, monocytes, and pools of myeloid progenitors including CD34+ cells that comprise blood. Unfortunately, reprogramming human blood cells by methods that do not rely on retro- or lenti-viral based systems are currently inefficient. One such method involves a plasmid-based approach that relies on the oriP replicon from Epstein-Barr virus (EBV) to facilitate retention and replication of plasmids within transfected host cells. For examle, cells may be transfected with oriP-based plasmids encoding combinations of reprogramming factors whereby the oriP replicon allows sufficient time for expression of the key reprogramming elements. The plasmids are then lost naturally from host cells at a rate of roughly 5-8% per cell division to generate iPS cells free of exogenous DNA (Nanbo et al., 2007).

Debate exists with regard to the maturation state of the blood cell and its correlation with reprogramming. For example, hematopoietic stem cell progenitors expressing CD34 have been perceived as desirable candidates based on the efficiency of iPS clone generation. This hypothesis has not been carefully tested to include differences among CD34+ cells derived from cord blood, mobilized/non-mobilized peripheral blood, and bone marrow collectively. Furthermore, CD34+ cells represent only a small fraction (0.01%) of the total population of peripheral blood mononuclear cells (PBMCs). Therefore, acquiring enough starting material from 1 mL of blood to generate multiple clones poses a challenge since the efficiency of reprogramming without the integration of DNA in blood cells is also low (<0.01%). B cells, on the other hand, represent a larger fraction of the PBMC population (roughly 20%) and it is contemplated that they could be more receptive to reprogramming.

In certain aspects of the invention, methods may be provided to immortalize a B cell-containing cell population by episomal vector elements and to reprogram resulting immortalized B cells subsequently. To save the need to introduce reprogramming expression cassettes separately, the episomal vector elements may comprise inducible reprogramming expression cassettes. In certain aspects, the methods may be provided to reprogram established transformed B cells, like lymphoblastoid cells.

A. Reprogramming of Transformed B Cells

Reprogramming of transformed B cells may be provided in certain aspects, for example, by using reprogramming expression cassettes or reprogramming proteins. Additional reprogramming factors for B cells such as Pax-5 inhibitors and C/EBPα enhancers may be used to enhance reprogramming based on the lineage specification status of the original B cells. In certain embodiments, Pax-5 inhibitors and C/EBPα enhancers may not be needed even for reprogramming mature B cells.

The generation of B-lymphocytes from hematopoietic stem cells is controlled by multiple transcription factors regulating distinct developmental aspects. Ikaros and PU.1 act in parallel pathways to control the development of lymphoid progenitors in part by regulating the expression of essential signaling receptors (Flt3, c-Kit, and IL-7Rα). The generation of the earliest B cell progenitors depends on the activation of E2A and EBF transcription factors, which coordinately activate the B cell gene expression program and immunoglobulin heavy-chain gene rearrangements to prime the onset of B-lymphopoiesis.

Pax-5 restricts the developmental options of lymphoid progenitors to the B cell lineage by repressing the transcription of lineage-inappropriate genes and simultaneously activating the expression of B-lymphoid signaling molecules. B cells exhibit plasticity during the earliest stages of B cell development. IL7, in combination with the three transcription factors E2A, EBF1, and Pax-5 (Kirchmaier and Sugden, 1997; Kennedy et al., 2003) play a key role in B cell differentiation. E2A and EBF1 activate the expression of B lymphoid genes at the onset of B cell development but the commitment to the lineage is controlled by Pax-5, which possesses the dual capacity of repressing the transcription of B-lineage-inappropriate genes and activating the expression of B-cell-specific genes (Mack and Sugden, 2008; Wendtner et al., 2003).

As the cells express Pax-5, pro-B cells can only differentiate along their unidirectional path to mature B cells. Pax-5−/− knock-out pro-B cells behave as multipotent progenitors because they express multi-lineage genes that allow them to be programmed into most of the hematopoietic lineages under the appropriate conditions.

The recent conversion of mature B cells into induced pluripotent stem cells (iPSCs) by forced expression of transcription factors Oct3/4, Sox2, Klf4, and c-Myc in combination with Pax-5 downregulation can be considered as a transdifferentiation process, that involves the generation of early progenitors from mature cells (Delecluse et al., 1999). This conversion involves the transition to a cellular state that reveals re-activation of genes related to stem cell renewal and maintenance and an incomplete repression of lineage-specific transcription factors and incomplete epigenetic remodeling.

Committed CD19+ B cells can also be transdifferentiated into macrophages by retroviral expression of the myeloid transcription factor C/EBPα (Delecluse et al., 1998; Hettich et al., 2006) in the presence of myeloid cytokines. The C/EBPα-induced conversion of committed B cells into macrophages happens via non-physiological cellular intermediates expressing markers belonging to both B cells and macrophages in a classical transdifferentiation manner.

Several other transcription factors have been identified to play important roles in regulating gene expression during B cell development, similar to the role of Pax-5, including Blimp1, Oct2 and Bob-1. Blimp1 is a critical transcriptional regulator of plasma cell differentiation. It is a repressor that is required for terminal differentiation of B cells and monocyte/macrophages. Oct2 is a B cell specific transcription factor which plays an important role in late B cell development. Bob-1 is a coactivator of Oct2 and Pax-5 (BSAP).

B. Lymphoblastoid Cells

Lymphoblastoid cell lines (LCLs) may be established by in vitro transformation of lymphocytes (such as any types of T cells or B cells) by episomal vector elements such as Epstein-Barr virus (EBV) or EBV-derived episomal vector elements. Transformation of peripheral B lymphocytes by Epstein-Barr virus (EBV) is a method of choice for generating LCLs. This method has been in use for the last two decades with a high success rate. With a somatic mutation rate of 0.3% and ease of cell maintenance, lymphoblastoid cells are still the preferred choice of storage for patients' genetic material.

Lymphoblastoid cell lines (LCLs) may also be obtained by immortalization of lymphocytes by virtue of non-EBV episomal vector. For example, lymphoblastoid cells may be established from Marek's Disease Virus (MDV) infection of T cells, primarily CD4+ cells (Parcells et al., 1999).

C. Additional Source of Immortalized Cells

Biologists have chosen the word immortal to designate cells that are not limited by the Hayflick limit (where cells no longer divide because of DNA damage or shortened telomeres). The Hayflick limit is the number of times a normal cell population will divide before it stops, presumably because the telomeres reach a critical length. The term immortalization was applied to cells that expressed the telomere-lengthening enzyme telomerase, and thereby avoided apoptosis (programmed cell death). Normal stem cells and germ cells can also be said to be immortal.

Immortal cells can be created by induction of oncogenes or loss of tumor suppressor genes. One way to induce immortality is through viral-mediated induction of the large T-antigen, commonly introduced through Simian Vacuolating virus 40 (SV40). SV40 large T antigen (SV40 TAg) is a hexamer protein that is an oncogene derived from the polyomavirus SV40 which is capable of transforming a variety of cell types.

In certain aspects of the invention, there may be provided somatic cells immortalized by virtue of episomal vector elements. Such episomal vector elements may express EBV genes for transformation of lymphocytes as described above, or express transgenes such as telomerase, or oncogenes for immortalization of any somatic cells.

The somatic cells may be terminally differentiated cells, or tissue stem cells, including, but not limited to, fibroblasts, hematopoietic cells, mesenchymal cells, keratinocytes, hematopoietic cells, liver cells, stomach cells, or neural stem cells. The somatic cells may be from a tissue cell bank or from a selected human subject, specifically, a live human. Genomes from progeny of these somatic cells will be considered to be derived from these somatic cells of a certain source, such as a selected human individual.

III. Episomal Vector Elements and Removal

The success in the establishment of iPS cells allows us to avoid bioethical problems attributed to ES cells, and this success is a major step towards realization of regenerative medicine free from immunological rejection. However, conventional methods for preparing iPS cells involve gene transduction via a retrovirus vector or another similar vector, a lentivirus vector. Such a viral vector may cause mutation of an endogenous gene, or may cause activation of an endogenous oncogene since the viral vector mediates the integration of a gene into a random position of the host cell's chromosomes. In view of future use of iPS cells in regenerative medicine, use of such a viral vector has the risks of oncogenic transformation and of developing dysfunction, etc. For that reason, an extremely important development toward future application of iPS cells are methods for preparing iPS cells without genome integrating reprogramming factors.

Episomal vector elements, including EBV or variants thereof, may be provided for immortalization of somatic cells, such as lymphocytes. In further aspects, episomal vector elements in the iPS cells may be removed after reprogramming.

Any episomal vector that has such properties can be used for the preparation method of the present invention, without particular limitation. Specifically, examples of the episomal vector include episomal vectors based on viruses, for example, an episomal vector based on a mouse polyomavirus (Gassmann et al., 1995); an episomal vector based on a BK virus, a kind of human polyomaviruses (De Benedetti and Rhoads, 1991); an episomal vector based on an Epstein-Barr virus (Margolskee et al., 1988); and an episomal vector based on a bovine papilloma virus (BPV) (Ohe et al., 1995). Inter alia, an episomal vector based on a BK virus and an episomal vector based on Epstein-Barr virus are suitably used for human cells.

Each of these vectors contains a replication origin (ori) derived from the corresponding virus. A "replication factor" binds to such a replication origin (ori), thereby triggering vector replication. The term "replication factor" as used herein refers to an indispensable factor for replication, which binds to the ori, thereby triggering nucleic acid replication. The "replication factors" corresponding to the respective virus-based episomal vectors illustrated above are the large T antigen of a mouse polyomavirus, the large T antigen of a BK virus, EBNA-1 of an EBV virus, and E1 and E2 of a BPV, respectively.

An episomal vector containing a base sequence called S/MAR (scaffold/matrix attachment region) can also be used suitably for the preparation method of the present invention. This episomal vector contains at least one S/MAR and at least one viral or eukaryotic replication origin (ori). Unlike other episomal vectors described above, this episomal vector does not require any replication factor corresponding to the ori for replication. Specifically, such an episomal vector is exemplified by the episomal vector containing, as an S/MAR, the upstream region (about 2 kbs) of the human interferon beta gene, which is described in Piechaczek et al. (1999).

In addition, there is known a system in which two kinds of adenovirus vectors introduced into cells produce a circular episomal vector within the cells (Leblois et al., 2000). The episomal vector obtained by using this system can also be used for the preparation method of the present invention. This system is based on the Cre-loxP system. More specifically, in the system, one adenovirus vector expresses Cre, and the other adenovirus vector contains a gene construct required for serving as an episomal vector, the gene construct being inserted into the region flanked by two loxP sites of the vector. The region flanked by the two loxP sites is excised by Cre, forming a circular DNA. When the region flanked by the two loxP sites is designed to carry a replication origin and a replication factor gene (for example, the oriP sequence and the gene encoding EBNA-1, which are a replication origin of and a replication factor gene of an Epstein-Barr virus, respectively) in addition to an expression unit, a formed circular DNA is maintained as an episome in cells.

B. Episomal Vector Backbone

These reprogramming methods may also make use of extra-chromosomally replicating vectors (i.e., episomal vectors), which are vectors capable of replicating episomally to make iPS cells essentially free of exogenous vector or viral elements (see U.S. Publication No. 20100003757, incorporated herein by reference; Yu et al., 2009). A number of DNA viruses, such as adenoviruses, Simian vacuolating virus 40 (SV40), EBV or bovine papilloma virus (BPV), or budding yeast ARS (Autonomously Replicating Sequences)-containing plasmids replicate extra-chromosomally or episomally in mammalian cells. These episomal plasmids are intrinsically free from all these disadvantages (Bode et al., 2001) associated with integrating vectors. For example, a lymphotrophic herpes virus-based vector comprising EBV elements as defined above may replicate extra-chromosomally and help deliver reprogramming factors to somatic cells.

For example, the plasmid-based approach used in the invention may extract robust elements necessary for the successful replication and maintenance of an EBV element-based system without compromising the system's tractability in a clinical setting as described in detail below. The essential EBV elements are oriP and EBNA-1 or their variants or functional equivalents. An additional advantage of this system is that these exogenous elements will be lost with time after being introduced into cells, leading to self-sustained iPS cells essentially free of exogenous elements.

The use of plasmid- or liposome-based extra-chromosomal vectors, e.g., oriP-based vectors, and/or vectors encoding a derivative of EBNA-1 permit large fragments of DNA to be introduced to a cell and maintained extra-chromosomally, replicated once per cell cycle, partitioned to daughter cells and elicit substantially no immune response. In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma-associated herpesvirus (KSHV), Herpes virus saimiri (HVS) and Marek's disease virus (MDV). Also other sources of episome-base vectors are contemplated, such as yeast ARS, adenovirus, SV40, or BPV.

To circumvent potential problems from viral gene delivery, two groups this year reported on a collaboration that has succeeded in transposon-based approaches for producing pluripotency in human cells without using viral vectors (Woltjen et al., 2009; Kaji et al., 2009). Stable iPS cells were produced in both human and mouse fibroblasts using virus-derived 2A peptide sequences to create a multicistronic vector incorporating the reprogramming factors, delivered to the cell by the piggyBac transposon vector. The 2A-linked reprogramming factors, not required in the established iPS cell lines, were then removed. These strategies could be similarly applied to immortalize and/or reprogram somatic cells in certain aspects of the present invention.

C. Epstein-Barr Virus-Based Vector Elements

The Epstein-Barr virus (EBV), also called Human herpesvirus 4 (HHV-4), is a gamma herpes virus of the human herpes family (which includes Herpes simplex virus, Vacricella-zoster virus and Cytomegalovirus), and is one of the most common viruses in humans.

EBV maintains its genome extra-chromosomally and works in collaboration with host cell machinery for efficient replication and maintenance (Lindner and Sugden, 2007), relying solely on two essential features for its replication and its retention within cells during cell division (Yates et al. 1985; Yates et al. 1984). One element, commonly referred to as oriP, exists in cis and serves as the origin of replication. The other factor, EBNA-1, functions in trans by binding to sequences within oriP to promote replication and maintenance of the plasmid DNA. Therefore, the EBNA-1 protein is essential for maintenance of the virus genome.

When EBV infects B-lymphocytes in vitro, lymphoblastoid cell lines eventually emerge that are capable of indefinite growth. The growth transformation of these cell lines is the consequence of viral protein expression. EBV genes such as EBNA-2, EBNA-3A, EBNA-3C, EBNA-LP and/or LMP-1 may be comprised in EBV vectors for transformation in certain aspects of the present invention.

1. OriP

OriP is the site at or near which DNA replication initiates and is composed of two cis-acting sequences approximately 1 kilobase pair apart known as the family of repeats (FR) and the dyad symmetry (DS).

FR is composed of 21 imperfect copies of a 30 by repeat and contains 20 high affinity EBNA-1-binding sites. When FR is bound by EBNA-1, it both serves as a transcriptional enhancer of promoters in cis up to 10 kb away (Reisman and Sugden, 1986; Yates, 1988; Sugden and Warren, 1989; Wysokenski and Yates, 1989; Gahn and Sugden, 1995; Kennedy and Sugden, 2003; Altmann et al., 2006), and contributes to the nuclear retention and faithful maintenance of FR containing plasmids (Langle-Rouault et al., 1998; Kirchmaier and Sugden, 1995; Wang et al., 2006; Nanbo et al., 2007). The efficient partitioning of oriP plasmids is also likely attributable to FR. While the virus has evolved to maintain 20 EBNA-1-binding sites in FR, efficient plasmid maintenance requires only seven of these sites, and can be reconstituted by a polymer of three copies of DS, having a total of 12 EBNA-1-binding sites (Wysokenski and Yates, 1989).

The dyad symmetry element (DS) is sufficient for initiation of DNA synthesis in the presence of EBNA-1 (Aiyar et al., 1998; Yates et al., 2000), and initiation occurs either at or near DS (Gahn and Schildkraut, 1989; Niller et al., 1995). Termination of viral DNA synthesis is thought to occur at FR, because when FR is bound by EBNA-1 it functions as a replication fork barrier as observed by 2D gel electrophoresis (Gahn and Schildkraut, 1989; Ermakova et al., 1996; Wang et al., 2006). Initiation of DNA synthesis from DS is limited to once-per-cell-cycle (Adams, 1987; Yates and Guan, 1991), and is regulated by the components of the cellular replication system (Chaudhuri et al., 2001; Ritzi et al., 2003; Dhar et al., 2001; Schepers et al., 2001; Zhou et al., 2005; Julien et al., 2004). DS contains four EBNA-1-binding sites, albeit with lower affinity than those found in FR (Reisman et al., 1985). The topology of DS is such that the four binding sites are arranged as two pairs of sites, with 21 by center-to-center spacing between each pair and 33 by center-to-center spacing between the two non-paired internal binding sites (Baer et al., 1984; Rawlins et al., 1985).

The functional roles of the elements within DS have been confirmed by studies of another region of the EBV genome, termed Rep*, which was identified as an element that can substitute for DS inefficiently (Kirchmaier and Sugden, 1998). Polymerizing Rep* eight times yielded an element as efficient as DS in its support of replication (Wang et al., 2006). Biochemical dissection of Rep* identified a pair of EBNA-1-binding sites with a 21 by center-to-center spacing critical for its replicative function (ibid). The minimal replicator of Rep* was found to be the pair of EBNA-1-binding sites, as replicative function was retained even after all flanking sequences in the polymer were replaced with sequences derived from lambda phage. Comparisons of DS and Rep* have revealed a common mechanism: these replicators support the initiation of DNA synthesis by recruiting the cellular replicative machinery via a pair of appropriately spaced sites, bent and bound by EBNA-1.

There are other extra-chromosomal plasmids that replicate in mammalian cells that are unrelated to EBV and in some ways appear similar to the zone of initiation within the Raji strain of EBV. Hans Lipps and his colleagues have developed and studied plasmids that contain "nuclear scaffold/matrix attachment regions" (S/MARs) and a robust transcriptional unit (Piechaczek et al., 1999; Jenke et al., 2004). Their S/MAR is derived from the human interferon-beta gene, is A/T rich, and operationally defined by its association with the nuclear matrix and its preferential unwinding at low ionic strength or when embedded in supercoiled DNA (Bode et al., 1992). These plasmids replicate semiconservatively, bind origin recognition complex (ORC) proteins, and support the initiation of DNA synthesis effectively and randomly throughout their DNA (Schaarschmidt et al., 2004). They are efficiently maintained in proliferating hamster and human cells without drug selection and when introduced into swine embryos can support expression of GFP in most tissues of fetal animals (Manzini et al., 2006).

2. EBNA-1

As a replication factor, Epstein Barr nuclear antigen 1 (EBNA-1) is a DNA-binding protein that binds to FR and DS of oriP or Rep* to facilitate replication and faithful partitioning of the EBV plasmid to daughter cells independent of, but in concert with, cell chromosomes during each cell division.

The 641 amino acids (AA) of EBNA-1 have been categorized into domains associated with its varied functions by mutational and deletional analyses. Two regions, between AA40-89 and AA329-378 are capable of linking two DNA elements in cis or in trans when bound by EBNA-1, and have thus been termed Linking Region 1 and 2 (LR1, LR2) (Middleton and Sugden, 1992; Frappier and O'Donnell, 1991; Su et al., 1991; Mackey et al., 1995). Fusing these domains of EBNA-1 to GFP homes the GFP to mitotic chromosomes (Marechal et al., 1999; Kanda et al., 2001). LR1 and LR2 are functionally redundant for replication; a deletion of either one yields a derivative of EBNA-1 capable of supporting DNA replication (Mackey and Sugden, 1999; Sears et al., 2004). LR1 and LR2 are rich in arginine and glycine residues, and resemble the AT-hook motifs that bind A/T rich DNA (Aravind and Landsman, 1998), (Sears et al., 2004). An in vitro analysis of LR1 and LR2 of EBNA-1 has demonstrated their ability to bind to A/T rich DNA (Sears et al., 2004). When LR1, containing one such AT-hook, was fused to the DNA-binding and dimerization domain of EBNA-1, it was found to be sufficient for DNA replication of oriP plasmids, albeit less efficiently than the wild-type EBNA-1 (ibid).

In specific embodiments of the invention, an episomal vector may contain both oriP and a version of EBNA-1 competent to support plasmid replication and its proper maintenance during cell division. The highly repetitive sequence within the amino-terminal one-third of wild-type EBNA-1 and a 25 amino-acid region that has demonstrated toxicity in various cells are dispensable for the trans-acting function of EBNA-1 associated with oriP (Yates et al. 1985; Kennedy et al. 2003). Therefore, an exemplary derivative, the abbreviated form of EBNA-1, known as deltaUR1, could be used alongside oriP within this plasmid-based system. More examples of EBNA-1 derivatives that can activate transcription from an extra-chromosomal template are known (see, for example, Kirchmaier and Sugden, 1997, and Kennedy and Sugden, 2003, both incorporated herein by reference).

A derivative of EBNA-1 used in the invention is a polypeptide which, relative to a corresponding wild-type polypeptide, has a modified amino acid sequence. The modifications include the deletion, insertion or substitution of at least one amino acid residue in a region corresponding to the unique region (residues about 65 to about 89) of LR1 (residues about 40 to about 89) in EBNA-1, and may include a deletion, insertion and/or substitution of one or more amino acid residues in regions corresponding to other residues of EBNA-1, e.g., about residue 1 to about residue 40, residues about 90 to about 328 ("Gly-Gly-Ala" repeat region), residues about 329 to about 377 (LR2), residues about 379 to about 386 (NLS), residues about 451 to about 608 (DNA binding and dimerization), or residues about 609 to about 641, so long as the resulting derivative has the desired properties, e.g., dimerizes and binds DNA containing an ori corresponding to oriP, localizes to the nucleus, is not cytotoxic, and activates transcription from an extrachromosomal vector but does not substantially activate transcription from an integrated template. Substitutions include substitutions which utilize the D rather than L form, as well as other well known amino acid analogs, e.g., unnatural amino acids such as α-disubstituted amino acids, N-alkyl amino acids, lactic acid, and the like.

3. Other EBV Genes

In certain aspects of the invention, the episomal vector elements may comprise one or more transforming genes, such as those derived from EBV, for example, EBNA-1, EBNA-2, EBNA-3A, EBNA-3C, EBNA-LP or LMP-1.

EBV infection in vitro converts primary human B cells into continuously proliferating lymphoblastoid cell lines (LCLs). In EBV-transformed LCLs, EBV expresses six nuclear proteins [EBV nuclear antigens (EBNAs) EBNA-1, EBNA-2, EBNA-3A, EBNA-3B, EBNA-3C, and EBNA-LP], three integral membrane proteins (LMP-1, LMP-2A, and LMP-2B), two small nonpolyadenylated RNAs (EBER1 and EBER2), and BamA rightward transcripts. Six of these viral latency proteins, EBNA-1, EBNA-2, EBNA-3A, EBNA-3C, EBNA-LP, and LMP-1, have been shown to be required for the transformation phenotype through reverse genetic experiments. EBV vectors for transformation may include one or more of these EBV transforming genes in certain aspects of the present invention.

EBV nuclear antigen 2 (EBNA-2) is a viral protein associated with Epstein-Barr virus. EBNA-2 is the main viral transactivator, switching transcription from the Wp promoters used initially after infection to the Cp promoter. The LMP-1 and LMP-2A/2B promoters are activated by EBNA-2 in B cells (Zimber-Strobl et al., 1991). It is known to bind the host RBP-Jκ protein that is a key player in the Notch pathway. c-Myc gene expression is induced by EBNA-2 mediated enhanced transcriptional initiation and EBNA-2 is essential for EBV-mediated growth transformation.

EBNA-3A, EBNA-3B, and EBNA-3C, which are arranged in tandem in the EBV genome, are encoded by genes that are similar in structure, leading to the proposal that the EBNA-3 genes may have arisen from a tandem triplication of an ancestral gene. The N-terminal amino acids of EBNA-3A, EBNA-3B, and EBNA-3C mediate interaction with a sequence-specific DNA-binding protein, RBP-Jκ. Reverse genetic experiments with recombinant EBVs indicate that EBNA-3A and EBNA-3C are essential for the EBV-mediated conversion of primary B cells into LCLs, whereas EBNA-3B is dispensable. EBNA-3C binds to and regulates cell cycle proteins, including Rb (Parker et al., 1996) and cyclin A (Knight and Robertson, 2004).

Latent membrane protein 1 (LMP-1) is one of the viral gene products that are essential for B cell transformation, and is essential for LCL proliferation (Kilger et al, 1998) and exhibits antiapoptotic properties namely through activating the NF-κB pathway (Cahir-McFarland et al. 2000 and 2004). LMP-1 is an integral membrane protein composed of a short cytoplasmic amino-terminal domain, six hydrophobic transmembrane domains, and a cytoplasmic carboxy-terminal domain. It has been demonstrated that LMP-1 acts as a constitutively active receptor that mimics activated CD40, a member of the tumor necrosis factor receptor family. The cytoplasmic carboxy terminus of LMP-1 plays a critical role in EBV-induced B-cell transformation through its binding to a tumor necrosis factor receptor-associated factor (TRAF) and a tumor necrosis factor receptor-associated death domain (TRADD) protein.

The LMP-1 (BNLF1) gene contains three exons that are located within the BamHI-N region of the EBV genome. Two open reading frames (ORFs) have been identified based on nucleotide sequences and mRNA mapping of B95-8 strain EBV. A transcript starting from the ED-L1 promoter, which is located upstream of the first exon, encodes the first ORF. This ORF encodes full-length LMP-1 (386 amino acids) that is abundantly expressed in lymphoblastoid cell lines. Another transcript starting from the ED-L1A promoter, which is located within the first intron of the LMP-1 gene, encodes the second ORF. The translation initiation site of this second ORF is methionine-129 of full-length LMP-1, and the ORF thus encodes an amino-terminally truncated form of the LMP-1 protein. The truncated LMP-1 (258 amino acids) consists of the fifth and sixth transmembrane domains and the cytoplasmic carboxy terminus of full-length LMP-1, and is expressed during lytic infection and reactivation of B cells (Hudson et al., 1985).

EBV nuclear antigen leader protein (EBNA-LP, or EBNA-4) plays a critical role in EBV induced B cell transformation. It is one of the first EBV latency proteins expressed after infection of primary B cells with EBV, suggesting it is required for cell activation and important for cell cycle progression during this time. Further evidence to support this claim is that EBNA-LP cooperates with EBNA-2 to activate transcription of cyclinD2 (Sinclair et al, 1994), as well as coactivating viral proteins including LMP-1 (Harada and Kieff, 1997).

D. Additional Episomal Vector Elements

In certain aspects, the episomal vector of the present invention contains an expression cassette for the gene encoding a nuclear reprogramming factor and/or for the gene encoding a replication factor. The promoter used for the expression unit may be any promoter used for mammalian cells, and includes, for example, a CAG promoter, a CMV promoter, a beta-actin promoter, an SV40 promoter, a PGK promoter and a MuLV LTR promoter. By inserting the gene (DNA) to be expressed downstream of such a promoter, expression of the gene product is achieved in cells. A plurality of genes can be expressed under the control of one promoter by using IRES (Internal Ribosome Entry Site). The IRES to be used is not particularly limited, and includes human HCV-derived IRES and picornavirus-derived IRES, for example.

In further aspects, the expression cassettes in the episomal vectors may be under the control of one or more externally controllable promoters. In certain aspects, the reprogramming expression cassettes may be induced to express reprogramming factors after immortalization. For example, the replication factor expression cassette may be induced for replication of episomal vector elements comprising immortalization genes or reprogramming factors for immortalization or reprogramming and may be turned off for later removal of episomal vector elements, thus inhibiting replication. The episomal vector may also comprise dominant negative mutants of replication factors, which interfere with the replication of episomal vectors and lead to their eventual loss from the host cells. The episomal vector may also comprise suicidal factors, which may be induced to kill the cells which retain the episomal vectors.

The episomal vector can carry a marker gene for isolating or enriching cells having the episomal vector introduced therein or for later vector removal. The marker gene is not particularly limited as long as it can be used for selecting cells having the episomal vector introduced therein, but a drug resistance gene is suitably used. Examples of drugs used for cell selection include, for example, neomycin (geneticin (G418)), hygromycin, puromycin, zeocin and blasticidin.

E. Vector Loss or Removal

In certain embodiments, the method may further comprising a step to select or enrich for cells with loss of episomal vector elements. For examples, in the absence of selection for cells comprising vectors, vector elements would be lost gradually from progeny cells. The selection may also comprise selection or enrichment based on marker gene expression.

In further embodiments, the method may comprise a vector removal step. The vector removal step is to remove episomal vectors from iPS cells. The vector removal step may be unnecessary because the number of copies of the introduced episomal vector may spontaneously diminish from the iPS cells during cell growth, thus resulting in its removal from the population of iPS cells. If episomal vectors remain in iPS cells, however, the undifferentiated state of the cells could become unstable or conversely the cells could lose the ability to differentiate. Therefore, it is preferred to conduct the vector removal step. Moreover, if episomal vectors remain for a long period of time, a foreign gene could become chromosomally integrated spontaneously thus resulting in a similar problem as is present for retroviral mediated gene integration. Therefore, it is preferred to conduct the vector removal step also in order to reduce the possibility of spontaneous chromosomal integration of a foreign gene, thereby reducing the risk of cellular oncogenic transformation and subsequent cellular dysfunction. The method for eliminating episomal vectors is not particularly limited, and non-limiting methods are provided below.

1. Cloning by Limiting Dilution

As described above, the presence of episomal vectors spontaneously decrease over time in conjunction with cell division. A population consisting only of iPS cells without episomal vectors can be obtained by continued culturing so as to enable cell division and by selecting for single clones utilizing the process of limiting dilution.

2. Use of Retroviral Promoter

While it is often the case that retroviral promoters do not drive gene expression in undifferentiated cells (Gorman et al., 1985), residual gene expression from such promoters has been reported (Yu et al. 2009). Many reports show that a retroviral vector becomes inactivated in undifferentiated cells (for example, Pannell et al., 2000). Therefore, when an episomal vector carrying the gene encoding a replication factor downstream of a retroviral promoter is employed, for example, the expression of the replication factor stops or is greatly limited after reprogramming of somatic cells into iPS cells. As a result, such an episomal vector loses the ability to replicate, and a population consisting only of iPS cells without the vectors is gradually formed. The gene ligated downstream of a retroviral promoter is not limited to the gene encoding a replication factor, and may be a gene encoding a nuclear reprogramming factor, but the gene encoding a replication factor is preferred from the viewpoint of suppressing vector replication.

3. Use of Drug-Regulated Gene Expression System

Expression of a target gene product can be regulated by switching medium conditions between the presence and absence of a specific drug. When this system is employed so that the expression of a replication factor is suspended by addition of a specific drug to the medium, the expression of the replication factor is inhibited, the episomal vector loses the ability to replicate, and then a population consisting only of iPS cells without the episomal vectors is gradually formed. The drug used for the drug-regulated gene expression system is not particularly limited, and any drug can be suitably used as long as it can help to realize such a system.

As a non-limiting example, the Tet-Off system is such a known system. In the Tet-Off system, the episomal vector carrying the gene encoding a replication factor can be designed so that the expression of the replication factor is suspended by addition of tetracycline (or any suitable analog thereof) to the medium. Specifically, for example, the primary vector used by in the examples can be modified to express tTA (tet-regulated transcriptional activator) under CMV promoter control, and to carry the gene encoding a replication factor (large T antigen) downstream of the tTA-regulated tetO (Tet operator sequence) promoter. The replication origin (ori) and the neomycin resistance gene in this vector remain unchanged. When such an episomal vector is employed, addition of tetracycline to medium after iPS cell selection inhibits the expression of the replication factor, the episomal vector loses the ability to replicate, and then a population consisting only of iPS cells without episomal vectors is gradually formed.

It is also possible to employ the Tet-On system, which is regulated in an opposite manner to the Tet-Off system, that is, in which the expression of the replication factor is suspended by removal of tetracycline from medium. In the case of employing the Tet-On system, medium with tetracycline should be used until iPS cells are formed, at which time this medium should be replaced with medium without tetracycline. The Tet-Off system and the Tet-On system are commercially available from Clontech.

A similar drug-regulated strategy may also apply to the conditional expression of suicidal genes, dominant negative mutants or other episomal removal agents from the episomal vectors.

4. Use of Herpesvirus-Derived Thymidine Kinase

The episomal vector is prepared so as to carry the herpesvirus-derived thymidine kinase gene in addition to the gene encoding a replication factor and/or the gene encoding a nuclear reprogramming factor. In this case, iPS cells which stop expressing the thymidine kinase due to loss of episomal vectors are allowed to selectively survive by addition of ganciclovir or aciclovir to medium after iPS cell selection. Thus, a population consisting only of iPS cells without episomal vectors can be obtained.

IV. Cell Reprogramming

In certain aspects of the invention, immortalized somatic cells may be reprogrammed to prepare iPS cells. Reprogramming may comprise increasing expression of one or more endogenous reprogramming factors or introducing one or more reprogramming factors in nucleic acid or protein form. In further aspects, signaling regulators such as small molecules may also be used to enhance reprogramming efficiency. Culturing conditions such as feeder-free conditions may also be used to facilitate reprogramming.

A. Reprogramming Factors

The generation of iPS cells is dependent upon the use of reprogramming factors. The following factors or combinations thereof could be used in the methods disclosed in the present invention. In certain aspects, nucleic acids encoding Sox and Oct (preferably Oct3/4) will be included into the reprogramming vector. For example, one or more reprogramming vectors may comprise expression cassettes encoding Sox2, Oct4, Nanog and optionally Lin28, or expression cassettes encoding Sox2, Oct4, Klf4 and optionally c-Myc, or expression cassettes encoding Sox2, Oct4, and optionally Esrrb, or expression cassettes encoding Sox2, Oct4, Nanog, Lin28, Klf4, c-Myc, and optionally SV40 Large T antigen. Nucleic acids encoding these reprogramming factors may be comprised in the same expression cassette, different expression cassettes, the same reprogramming vector, or different reprogramming vectors.

Oct4 and certain members of the Sox gene family (Sox1, Sox2, Sox3, and Sox15) have been identified as crucial transcriptional regulators involved in the induction process whose absence makes induction impossible. Additional genes, however, including certain members of the Klf family (Klf1, Klf2, Klf4, and Klf5), the Myc family (c-Myc, L-Myc, and N-Myc), Nanog, and Lin28, have been identified to increase the induction efficiency.

Oct4 (Pou5f1) is one of the family of octamer ("Oct") transcription factors, and plays a crucial role in maintaining pluripotency. The absence of Oct4 in Oct4$^+$ cells, such as blastomeres and embryonic stem cells, leads to spontaneous trophoblast differentiation, and presence of Oct4 thus gives rise to the pluripotency and differentiation potential of embryonic stem cells. Various other genes in the "Oct" family, including Oct4's close relatives, Oct1 and Oct6, fail to elicit induction, thus demonstrating the exclusiveness of Oct4 to the induction process.

The Sox family of genes is associated with maintaining pluripotency similar to Oct4, although it is associated with multipotent and unipotent stem cells in contrast with Oct4, which is exclusively expressed in pluripotent stem cells.

While Sox2 was the initial gene used for induction by Yamanaka et al., Jaenisch et al., and Thompson et al., other genes in the Sox family have been found to work as well in the induction process. Sox1 yields iPS cells with a similar efficiency as Sox2, and genes Sox3, Sox15, and Sox18 also generate iPS cells, although with decreased efficiency.

In embryonic stem cells, Nanog, along with Oct4 and Sox2, is necessary in promoting pluripotency. Therefore, it was surprising when Yamanaka et al. reported that Nanog was unnecessary for iPS cell generation although Thomson et al. has reported it is possible to generate iPS cells with Nanog as one of the factors.

Lin28 is an mRNA binding protein expressed in embryonic stem cells and embryonic carcinoma cells associated with differentiation and proliferation. Thomson et al. demonstrated it is a factor in iPS generation, although it is unnecessary.

Klf4 of the Klf family of genes was initially identified by Yamanaka et al. and confirmed by Jaenisch et al. as a factor for the generation of mouse iPS cells and was demonstrated by Yamanaka et al. as a factor for generation of human iPS cells. However, Thompson et al. reported that Klf4 was unnecessary for generation of human iPS cells and in fact failed to generate human iPS cells. Klf2 and Klf4 were found to be factors capable of generating iPS cells, and related genes Klf1 and Klf5 did as well, although with reduced efficiency.

The Myc family of genes are proto-oncogenes implicated in cancer. Yamanaka et al. and Jaenisch et al. demonstrated that c-Myc is a factor implicated in the generation of mouse iPS cells and Yamanaka et al. demonstrated it was a factor implicated in the generation of human iPS cells. However, Thomson et al. and Yamanaka et al. reported that c-Myc was unnecessary for generation of human iPS cells. Usage of the "Myc" family of genes in induction of iPS cells is troubling for the eventuality of iPS cells as clinical therapies, as 25% of mice transplanted with c-Myc-induced iPS cells developed lethal teratomas. N-Myc and L-Myc can also contribute toward iPS cell generation, exhibiting similar efficiency to c-Myc. SV40 large T antigen may be used to reduce or prevent the cytotoxcity that may occur when c-Myc is expressed.

The reprogramming proteins used in the present invention can be substituted by protein homologs with about the same reprogramming functions. Nucleic acids encoding those homologs could also be used for reprogramming. Conservative amino acid substitutions are preferred-that is, for example, aspartic-glutamic as polar acidic amino acids; leucine/isoleucine/methionine/valine/alanine/glycine/proline as non-polar or hydrophobic amino acids; lysine/arginine/histidine as polar basic amino acids; acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide.

B. Reprogramming Signaling Inhibitors

In certain aspects of the invention, during at least part of the reprogramming process, the cell may be maintained in the presence of one or more signaling inhibitors which inhibit a signal transducer involved in a signaling cascade, e.g., in the presence of a MEK inhibitor, a GSK-3 inhibitor, a TGF-β receptor inhibitor, both a MEK inhibitor and a GSK-3 inhibitor, both a GSK-3 inhibitor and a TGF-β receptor inhibitor, both a MEK inhibitor and a TGF-β receptor inhibitor, a combination of all three inhibitors, or inhibitor of other signal transducers within these same pathways. In certain aspects, ROCK inhibitors, such as HA-100 or H-1152, or myosin II ATPase inhibitors, such as blebbistatin, may be used to facilitate clonal expansion of reprogrammed cells and resulting iPS cells.

High concentration of FGF, in combination with specific reprogramming medium such as conditioned human ES cell culture medium or serum-free defined N2B27 medium, may also be used to increase reprogramming efficiency. Externally added FGF, signaling inhibitors or any other chemicals (e.g., β-mercaptoethanol) used herein may be at an amount of at least, about or at most 0.1, 1, 5, 10, 15, 20, 25, 30, 35, 40, 45, 50, 55, 60, 65, 70, 75, 80, 90, 100, 150, 200, 250, 300, 350, 400, 450, 500, 600, 700, 800, 900 ng/mL, at least, about, or at most 0.05, 0.1, 0.2, 0.2, 0.3, 0.4, 0.5, 0.6, 0.7, 0.8, 0.9, 1, 1.5, 2, 2.5, 3, 4, 5, 6, 7, 8, 9, 10, 20, 30, 40, 50, 60, 70, 80, 90, 100, 200, 300, 400, 500, 600, 700, 800, 900 μM, 1, 2, 3, 4, 5, 6, 7, 8, 9, 10 mM, or any range derivable therein, or any concentration effective for improving episomal reprogramming. In specific embodiments, high concentration of FGF may be used, for example, about 40 to 200 ng/mL, or more particularly, about 100 ng/mL. More details of the methods for reprogramming cells with signaling inhibitors have been disclosed in U.S. Application No. 61/258,120 incorporated herein by reference.

In certain embodiments, in addition to introducing the cells with one or more reprogramming factors (e.g. two, three or more, as described herein) by episomal vector elements, the cells are treated with a reprogramming medium comprising: a MEK inhibitor, a TGF-β receptor inhibitor, a GSK-3 inhibitor, and optionally Leukemia inhibitory factor (LIF). The use of such molecules may result in improved reprogramming efficiency and kinetics, thereby facilitating iPS cell identification in the primary reprogramming culture, thus preserving iPS cell clonality.

It will be understood that in these aspects and embodiments, other signaling inhibitors which inhibit a signaling component of the same signaling pathway (e.g. ERK1 or ERK2 cascade) may be substituted where desired for the MEK inhibitor. This may include inhibition of an upstream stimulus of the MAPK pathway, in particular through the FGF receptor (Ying, 2008). Likewise, the GSK-3 inhibitor may be substituted where desired for other inhibitors of GSK-3-related signaling pathways, such as insulin synthesis and Wnt/β-catenin signaling; LIF may be substituted where desired for other activators of Stat3 or gp130 signaling.

Such a signaling inhibitor, e.g., a MEK inhibitor, a GSK-3 inhibitor, a TGF-β receptor inhibitor, may be used at an effective concentration of at least or about 0.02, 0.05, 0.1, 0.2, 0.5, 1, 2, 3, 4, 5, 10, 15, 20, 25, 30, 35, 40, 45, 50, 100, 150, 200, 500 to about 1000 μM, or any range derivable therein.

Inhibitors may be provided or obtained by those skilled in the art by conventional means or from conventional sources (see also WO2007113505).

1. Glycogen Synthase Kinase 3 Inhibitor

Glycogen synthase kinase 3 (GSK-3) is a serine/threonine protein kinase that mediates the addition of phosphate molecules on certain serine and threonine amino acids in particular cellular substrates. The phosphorylation of these other proteins by GSK-3 usually inhibits the target protein (also called the "substrate"). As mentioned, GSK-3 is known for phosphorylating and thus inactivating glycogen synthase. It has also been implicated in the control of cellular response to damaged DNA and Wnt signaling. GSK-3 also phosphorylates Ci in the Hedgehog (Hh) pathway, targeting it for proteolysis to an inactive form. In addition to glycogen synthase, GSK-3 has many other substrates. However, GSK-3 is unusual among the kinases in that it usually requires a "priming kinase" to first phosphorylate a substrate.

The consequence of GSK-3 phosphorylation is usually inhibition of the substrate. For example, when GSK-3 phosphorylates another of its substrates, the NFAT family of transcription factors, these transcription factors cannot translocate to the nucleus and are therefore inhibited. In addition to its important role in the Wnt signaling pathway, which is required for establishing tissue patterning during development, GSK-3 is also critical for the protein synthesis that is induced in settings such as skeletal muscle hypertrophy. Its roles as an NFAT kinase also places it as a key regulator of both differentiation and cellular proliferation.

GSK-3 inhibition may refer to inhibition of one or more GSK-3 enzymes. The family of GSK-3 enzymes is well-known and a number of variants have been described (see e.g. Schaffer et al., 2003). In specific embodiments GSK3-β is inhibited. GSK3-α inhibitors are also suitable, and in certain aspects inhibitors for use in the invention inhibit both GSK3-α and GSK3-β.

Inhibitors of GSK-3 can include antibodies that bind, dominant negative variants of, and siRNA and antisense nucleic acids that target GSK3. Examples of GSK-3 inhibitors are described in Bennett et al. (2002) and in Ring et al. (2003).

Specific examples of GSK-3 inhibitors include, but are not limited to, Kenpaullone, 1-Azakenpaullone, CHIR99021, CHIR98014, AR-A014418 (see, e.g., Gould et al., 2004), CT 99021 (see, e.g., Wagman, 2004), CT 20026 (see, Wagman, supra), SB415286, SB216763 (see, e.g., Martin et al., 2005), AR-A014418 (see, e.g., Noble et al., 2005), lithium (see, e.g., Gould et al., 2003), SB 415286 (see, e.g., Frame et al., 2001) and TDZD-8 (see, e.g., Chin et al., 2005). Further exemplary GSK-3 inhibitors available from Calbiochem (see, e.g., Dalton et al., WO2008/094597, herein incorporated by reference), include but are not limited to BIO (2'Z,3'£)-6-Bromomdirubm-3'-oxime (GSK-3 Inhibitor IX); BIO-Acetoxime (2'Z,3'E)-6-Bromoindirubin-3'-acetoxime (GSK-3 Inhibitor X); (5-Methyl-1H-pyrazol-3-yl)-(2-phenylquinazolin-4-yDamine (GSK-3 Inhibitor XIII); Pyridocarbazole-cyclopenadienylruthenium complex (GSK-3 Inhibitor XV); TDZD-8 4-Benzyl-2-methyl-1,2,4-thiadiazolidine-3,5-dione (GSK-3beta Inhibitor I); 2-Thio(3-iodobenzyl)-5-(1-pyridyl)-[1,3,4]-oxadiazole (GSK-3beta Inhibitor II); OTDZT 2,4-Dibenzyl-5-oxothiadiazolidine-3-thione (GSK-3beta Inhibitor III); alpha-4-Dibromoacetophenone (GSK-3beta Inhibitor VII); AR-AO 14418 N-(4-Methoxybenzyl)-N'-(5-nitro-1,3-thiazol-2-yl)urea (GSK-3beta Inhibitor VIII); 3-(1-(3-Hydroxypropyl)-1H-pyrrolo[2,3-b]pyridin-3-yl]-4-pyrazin-2-yl-pyrrole-2,5-dione (GSK-3beta Inhibitor XI); TWS1 19 pyrrolopyrimidine compound (GSK-3beta Inhibitor XII); L803 H-KEAPP APPQSpP-NH2 or its Myristoylated form (GSK-3beta Inhibitor XIII); 2-Chloro-1-(4,5-dibromo-thiophen-2-yl)-ethanone (GSK-3beta Inhibitor VI); AR-AO144-18; SB216763; and SB415286.

GSK-3 inhibitors can activate, for example, the Wnt/β-catenin pathway. Many of β-catenin downstream genes co-regulate pluripotency gene networks. For example, a GSK-3 inhibitor activates c-Myc expression as well as enhances its protein stability and transcriptional activity. Thus, in some embodiments, GSK-3 inhibitors can be used to stimulate endogenous Myc polypeptide expression in a cell, thereby eliminating the need for Myc expression to induce pluripotency.

In addition, the structure of the active site of GSK-3β has been characterized and key residues that interact with specific and non-specific inhibitors have been identified (Bertrand et al., 2003). This structural characterization allows additional GSK inhibitors to be readily identified.

The inhibitors used herein are preferably specific for the kinase to be targeted. The inhibitors of certain embodiments are specific for GSK-3β and GSK-3α, substantially do not inhibit erk2 and substantially do not inhibit cdc2. Preferably the inhibitors have at least 100 fold, more preferably at least 200 fold, very preferably at least 400 fold selectivity for human GSK-3 over mouse erk2 and/or human cdc2, measured as ratio of $IC_{50}$ values; here, reference to GSK-3 $IC_{50}$ values refers to the mean values for human GSK-3β and GSK-3α. Good results have been obtained with CHIR99021 which is specific for GSK-3. Suitable concentrations for use of CHIR99021 are in the range 0.01 to 100, preferably 0.1 to 20, more preferably 0.3 to 10 micromolar.

2. MEK Inhibitor

MEK inhibitors, which include inhibitors of mitogen-activated protein kinase kinase (MAPK/ERK kinase or MEK) or its related signaling pathways like MAPK cascade, may be used in certain aspects of the invention. Mitogen-activated protein kinase kinase (sic) is a kinase enzyme which phosphorylates mitogen-activated protein kinase. It is also known as MAP2K. Extracellular stimuli lead to activation of a MAP kinase via a signaling cascade ("MAPK cascade") composed of MAP kinase, MAP kinase kinase (MEK, MKK, MEKK, or MAP2K), and MAP kinase kinase kinase (MKKK or MAP3K).

A MEK inhibitor herein refers to MEK inhibitors in general. Thus, a MEK inhibitor refers to any inhibitor of a member of the MEK family of protein kinases, including MEK1, MEK2 and MEK5. Reference is also made to MEK1, MEK2 and MEK5 inhibitors. Examples of suitable MEK inhibitors, already known in the art, include the MEK1 inhibitors PD184352 and PD98059, inhibitors of MEK1 and MEK2 U0126 and SL327, and those discussed in Davies et al. (2000).

In particular, PD184352 and PD0325901 have been found to have a high degree of specificity and potency when compared to other known MEK inhibitors (Bain et al., 2007). Other MEK inhibitors and classes of MEK inhibitors are described in Zhang et al. (2000).

Inhibitors of MEK can include antibodies to, dominant negative variants of, and siRNA and antisense nucleic acids that suppress expression of MEK. Specific examples of MEK inhibitors include, but are not limited to, PD0325901 (see, e.g., Rinehart et al., 2004), PD98059 (available, e.g., from Cell Signaling Technology), U0126 (available, for example, from Cell Signaling Technology), SL327 (available, e.g., from Sigma-Aldrich), ARRY-162 (available, e.g., from Array Biopharma), PD184161 (see, e.g., Klein et al., 2006), PD184352 (CI-1040) (see, e.g., Mattingly et al., 2006), sunitinib (see, e.g., Voss, et al., US2008004287 incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluated in Phase I and II clinical trials for cancer (see, e.g., Rinehart et al., 2004). Other MEK inhibitors being evaluated in clinical trials include PD 184352 (see, e.g., English et al., 2002), BAY 43-9006 (see, e.g., Chow et al., 2001), PD-325901 (also PD0325901), GSK1 120212, ARRY-438162, RDEA1 19, AZD6244 (also ARRY-142886 or ARRY-886), RO5126766, XL518 and AZD8330 (also ARRY-704).

Inhibition of MEKs can also be conveniently achieved using RNA-mediated interference (RNAi). Typically, a double-stranded RNA molecule complementary to all or part of a MEK gene is introduced into pluripotent cells, thus promoting specific degradation of MEK-encoding mRNA molecules. This post-transcriptional mechanism results in reduced or abolished expression of the targeted MEK gene. Suitable techniques and protocols for achieving MEK inhibition using RNAi are known.

A number of assays for identifying kinase inhibitors, including GSK-3 inhibitors and MEK inhibitors, are known. For example, Davies et al. (2000) describes kinase assays in which a kinase is incubated in the presence of a peptide substrate and radiolabeled ATP. Phosphorylation of the substrate by the kinase results in incorporation of the label into the substrate. Aliquots of each reaction are immobilized on phosphocellulose paper and washed in phosphoric acid to remove free ATP. The activity of the substrate following incubation is then measured and provides an indication of kinase activity. The relative kinase activity in the presence and absence of candidate kinase inhibitors can be readily determined using such an assay. Downey et al. (1996) also describes assays for kinase activity which can be used to identify kinase inhibitors.

3. TGF-β Receptor Inhibitor

TGF-β receptor inhibitors may include any inhibitors of TGF signaling in general or inhibitors specific for TGF-β receptor (e.g., ALK5) inhibitors, which can include antibodies to, dominant negative variants of, and siRNA and antisense nucleic acids that suppress expression of, TGF beta receptors (e.g., ALK5). Exemplary TGF-β receptor/ALK5 inhibitors include, but are not limited to, SB431542 (see, e.g., Inman et al., 2002), A-83-01, also known as 3-(6-Methyl-2-pyridinyl)-N-phenyl-4-(4-quinolinyl)-1H-p yrazole-1-carbothioamide (see, e.g., Tojo et al., 2005, and commercially available from, e.g., Toicris Bioscience); 2-(3-(6-Methylpyridin-2-yl)-1H-pyrazol-4-yl)-1,5-naphthyridine, Wnt3a/BIO (see, e.g., Dalton, et al., WO2008/094597, herein incorporated by reference), BMP4 (see, Dalton, supra), GW788388 (-(4-[3-(pyridin-2-yl)-1H-pyrazol-4-yl]pyridin-2-yl}-N-(tetrahydro-2H-pyran-4-yl)benzamide) (see, e.g., Gellibert et al., 2006), SM16 (see, e.g., Suzuki et al., 2007), IN-1130 (3-((5-(6-methylpyridin-2-yl)-4-(quinoxalin-6-yl)-1H-imidazol-2-yl)methyl)benzamide) (see, e.g., Kim et al., 2008), GW6604 (2-phenyl-4-(3-pyridin-2-yl-lH-pyrazol-4-yl)pyridine) (.see, e.g., de Gouville et al., 2006), SB-505124 (2-(5-benzo[1,3] dioxol-5-yl-2-tert-butyl-3H-imidazol-4-yl)-6-methylpyridine hydrochloride) (see, e.g., DaCosta et al., 2004) and pyrimidine derivatives (see, e.g., those listed in Stiefl et al., WO2008/006583, herein incorporated by reference).

Further, while an "ALK5 inhibitor" is not intended to encompass non-specific kinase inhibitors, an "ALK5 inhibitor" should be understood to encompass inhibitors that inhibit ALK4 and/or ALK7 in addition to ALK5, such as, for example, SB-431542 (see, e.g., Inman et al., 2002). Without intending to limit the scope of the invention, it is believed that ALK5 inhibitors affect the mesenchymal to epithelial conversion/transition (MET) process. TGF-β/activin pathway is a driver for epithelial to mesenchymal transition (EMT). It is contemplated that inhibiting the TGF-β/activin pathway can facilitate MET (i.e., reprogramming) process.

It is believed that inhibition of the TGF-β/activin pathway will have similar effects. Thus, any inhibitor (e.g., upstream or downstream) of the TGF-β/activin pathway can be used in combination with, or instead of, TGF-β/ALK5 inhibitors as described herein. Exemplary TGF-β/activin pathway inhibitors include but are not limited to: TGF beta receptor inhibitors, inhibitors of SMAD 2/3 phosphorylation, inhibitors of the interaction of SMAD 2/3 and SMAD 4, and activators/agonists of SMAD 6 and SMAD 7. Furthermore, the categorizations described herein are merely for organizational purposes and one of skill in the art would know that compounds can affect one or more points within a pathway, and thus compounds may function in more than one of the defined categories.

TGF beta receptor inhibitors can include antibodies to, dominant negative variants of, and siRNA or antisense nucleic acids that target TGF beta receptors. Specific examples of inhibitors include but are not limited to SU5416; 2-(5-benzo[1,3]dioxol-5-yl-2-tert-butyl-3H-imidazol-4-yl)-6-methylpyridine hydrochloride (SB-505124); lerdelimumb (CAT-152); metelimumab (CAT-192); GC-1008; ID1 1; AP-12009; AP-11014; LY550410; LY580276; LY364947; LY2109761; SB-505124; SB-431542; SD-208; SM16; NPC-30345; Ki26894; SB-203580; SD-093; Gleevec; 3,5,7,2',4'-pentahydroxyfiavone (Morin); activin-M108A; P144; soluble TBR2-Fc; and antisense transfected tumor cells that target TGF beta receptors (See, e.g., Wrzesinski et al., 2007; Kaminska et al., 2005; and Chang et al., 2007.)

C. Culturing of Reprogrammed Cells

After immortalized somatic cells are introduced with reprogramming factors using the disclosed methods, these cells may be cultured in a medium sufficient to maintain the pluripotency. Culturing of induced pluripotent stem (iPS) cells generated in this invention can use various media and techniques developed to culture primate pluripotent stem cells, more specially, embryonic stem cells, as described in U.S. Pat. App. 20070238170 and U.S. Pat. App. 20030211603. It is appreciated that additional methods for the culture and maintenance of human pluripotent stem cells, as would be known to one of skill, may be used with the present invention.

In certain embodiments, undefined conditions may be used; for example, pluripotent cells may be cultured on fibroblast feeder cells or a medium which has been exposed to fibroblast feeder cells in order to maintain the stem cells in an undifferentiated state. Alternately, pluripotent cells may be cultured and maintained in an essentially undifferentiated state using defined, feeder-independent culture system, such as a TeSR medium (Ludwig et al., 2006a; Ludwig et al., 2006b). Feeder-independent culture systems and media may be used to culture and maintain pluripotent cells. These approaches allow iPS cells to remain in an essentially undifferentiated state without the need for mouse fibroblast "feeder layers." As described herein, various modifications may be made to these methods in order to reduce costs as desired.

For example, like human embryonic stem (hES) cells, iPS cells can be maintained in 80% DMEM (Gibco #10829-018 or #11965-092), 20% defined fetal bovine serum (FBS) not heat inactivated (or human AB serum), 1% non-essential amino acids, 1 mM L-glutamine, and 0.1 mM β-mercaptoethanol. Alternatively, iPS cells can be maintained in serum-free medium, made with 80% Knock-Out DMEM (Gibco

10829-018), 20% serum replacement (Gibco #10828-028), 1% non-essential amino acids, 1 mM L-glutamine, and 0.1 mM β-mercaptoethanol. Just before use, human bFGF may be added to a final concentration of about 4 ng/mL (WO 99/20741) or zebrafish bFGF may be used instead as in the Examples.

Various matrix components may be used in culturing and maintaining human pluripotent stem cells, preferably in the place of feeder cells. For example, Matrigel™, collagen IV, fibronectin, laminin, and vitronectin in combination may be used to coat a culturing surface as a means of providing a solid support for pluripotent cell growth, as described in Ludwig et al. (2006a; 2006b), which are incorporated by reference in their entirety. Particularly, Matrigel™ may be used to provide a substrate for cell culture and maintenance of human pluripotent stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture.

iPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10 \times 10^6$ cells into the rear leg muscles of 8-12 week old male SCID mice. Teratomas develop that demonstrate at least one cell type of each of the three germ layers.

V. Reprogramming Factors Expression and Transduction

In certain aspects of the present invention, reprogramming factors are expressed from expression cassettes comprised in one or more vectors. The vectors may be an integrating vector or an episomal vector. In a further aspect, reprogramming proteins could be introduced directly into somatic cells by protein transduction (see U.S. Application No. 61/172,079, incorporated herein by reference).

A. Integrating and Episomal Vectors iPS cells may be generated by integration of certain nucleic acids or genes encoding reprogramming proteins into non-pluripotent cells, such as transformed B cells, in the present invention. DNA delivery is typically achieved through integrating viral vectors in the current practice, such as retroviruses. Transduced genes may include the master transcriptional regulators Oct4 (Pouf51) and Sox2, although it is suggested that other genes enhance the efficiency of induction. After a critical period, small numbers of transduced cells may begin to become morphologically and biochemically similar to pluripotent stem cells, and could be isolated through morphological selection, doubling time, or through a reporter gene and antibiotic selection.

In November 2007, a milestone was achieved by creating iPS from adult human fibroblasts from two independent research teams' studies (Yu et al., 2007; Yamanaka et al., 2007). With the same principle used earlier in mouse models, Yamanaka had successfully transformed human fibroblasts into pluripotent stem cells using the same four pivotal genes: Oct4, Sox2, Klf4, and c-Myc with a retroviral system but c-Myc is oncogenic. Thomson and colleagues used Oct4, Sox2, Nanog, and a different gene Lin28 using a lentiviral system avoiding the use of c-Myc.

As described above, induction of pluripotent stem cells from human dermal fibroblasts has been achieved using retroviruses or lentiviral vectors for ectopic expression of reprogramming genes. Recombinant retroviruses such as the Moloney murine leukemia virus (MMLV) have the ability to integrate into the host genome in a stable fashion. They contain a reverse transcriptase that allows integration into the host genome. Lentiviruses are a subclass of Retroviruses. They are widely adapted as vectors thanks to their ability to integrate into the genome of non-dividing as well as dividing cells. The viral genome in the form of RNA is reverse-transcribed when the virus enters the cell to produce DNA, which is then inserted into the genome at a random position by the viral integrase enzyme.

Introduction of reprogramming factor genes may also be accomplished by using a transposon—transposase system. Such transposon—transposase systems that could be used are the Sleeping Beauty system, the Frog Prince system (for the description of the latter see e.g. EP1507865), or the TTAA-specific piggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

These reprogramming methods may also make use of extra-chromosomally replicating vectors (i.e., episomal vectors) which are vectors capable of replicating episomally to make iPS cells essentially free of exogenous vector or viral elements (see U.S. Publication No. 2010/0003757, incorporated herein by reference; Yu et al., 2009), as has been previously described herein.

B. Protein Transduction

One possible way to avoid introducing exogenous genetic modifications to target cells would be to deliver the reprogramming proteins directly into cells, rather than relying on the transcription from delivered genes. Previous studies have demonstrated that various proteins can be delivered into cells in vitro and in vivo by conjugating them with a short peptide that mediates protein transduction, such as HIV Tat and poly-arginine. A recent study demonstrated that murine fibroblasts can be fully reprogrammed into pluripotent stem cells by direct delivery of recombinant reprogramming proteins (Zhou et al., 2009). More details of the methods for reprogramming cells with protein transduction have been disclosed in U.S. Application No. 61/172,079 incorporated herein by reference.

In certain aspects of the present invention, protein transduction domains could be used to introduce reprogramming proteins directly into immortalized somatic cells. Protein transduction could be a method for enhancing the delivery of reprogramming proteins into cells. For example, a region of the Tat protein, which is derived from the HIV Tat protein, can be fused to a target protein allowing the entry of the target protein into the cell. The advantages of using fusions of these transduction domains are that protein entry is rapid, concentration-dependent and appear to work with different cell types.

In a further aspect of the present invention, nuclear localization sequence may also be used to facilitate nuclear entry of reprogramming proteins. Nuclear localization signals (NLS) have been described for various proteins. The mechanism of protein transport to the nucleus is through the binding of a target protein containing a nuclear localization signal to alpha subunit of karyopherin. This is followed by transport of the target protein:karyopherin complex through the nuclear pore and into the nucleus. However, reprogramming proteins are often transcription factors that may have endogenous nuclear localization sequences. Therefore, nuclear localization sequences may not be necessary.

The direct introduction of reprogramming proteins into somatic cells may be used in the present invention, with reprogramming proteins operatively linked to a protein transduction domain (PTD), either by creating a fusion protein comprising such a domain or by chemically cross-linking the reprogramming protein and PTD via functional groups on each molecule.

Standard recombinant nucleic acid methods can be used to express one or more transducible reprogramming proteins used herein. In one embodiment, a nucleic acid sequence encoding the transducible protein is cloned into a nucleic acid expression vector, e.g., with appropriate signal and processing sequences and regulatory sequences for transcription and translation. In another embodiment, the protein can be synthesized using automated organic synthetic methods.

In addition, there have been several methods that may also help the transport of proteins into cells, one or more of which can be used alone or in combination with the methods using the protein transduction domains, including, but not limited to, microinjection, electroporation, and the use of liposomes. Most of these methods may need a purified preparation of protein. Purification of recombinant proteins is often facilitated by the incorporation of an affinity tag into the expression construct, making the purification step fast and efficient.

VI. Vector Construction and Delivery

In certain embodiments, vectors for immortalizing and/or reprogramming could be constructed to comprise additional elements in addition to nucleic acid sequences encoding various components such as immortalizing genes or reprogramming factors as described above in cells. Details of components of these vectors and delivery methods are disclosed below.

A. Vector

One of skill in the art would be well equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also might include markers, such as detectable and/or selection markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell nucleus or cytoplasm.

B. Regulatory Elements

Eukaryotic expression cassettes included in the vectors preferably contain (in a 5'-to-3' direction) a eukaryotic transcriptional promoter operably linked to a protein-coding sequence, splice signals including intervening sequences, and a transcriptional termination/polyadenylation sequence.

1. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

Promoters suitable for use in EBNA-1-encoding vectors of the invention are those that direct the expression of the expression cassettes encoding the EBNA-1 protein to result in sufficient steady-state levels of EBNA-1 protein to stably maintain EBV oriP-containing vectors. Promoters are also used for efficient expression of expression cassettes encoding reprogramming factors.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. For example, in the HSV-tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively direct the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

In certain embodiments of the invention, the use of a sequence coding for at least one protease cleavage site and/or self-cleaving peptide for polycistronic transcription can be used. For example, there are several self-cleaving peptides such as a viral 2A peptide.

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference).

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that the terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in certain aspects of the invention include a known terminator of transcription described herein or a terminator known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in differentiation programming, which is a specific nucleic acid sequence at which replication is initiated. Alternatively a replication origin of other extra-chromosomally replicating virus as described above or an autonomously replicating sequence (ARS) can be employed.

8. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select vector-free cells after the differentiation programming factors have effected a desired altered differentiation status in those cells.

C. Vector Delivery

Introduction of a vector into cells with the current invention may use any suitable methods for nucleic acid delivery into cells, as described herein (e.g., viral transduction) or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine2000 (Gibco BRL) or Superfect (Qiagen). The amount of liposomes used may vary upon the nature of the liposome as well as the, cell used, for example, about 5 to about 20 µg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus of Japan (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into a cell via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 µg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

5. Sonication Loading

Additional embodiments of the present invention include the introduction of a nucleic acid by direct sonic loading. LTK$^-$ fibroblasts have been transfected with the thymidine kinase gene by sonication loading (Fechheimer et al., 1987).

6. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

7. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

VII. Differentiation of iPS Cells

Various approaches may be used with the present invention to differentiate iPS cells into cell lineages including, but not limited to, hematopoietic cells, myocytes (e.g., cardiomyocytes), neurons, fibroblasts and epidermal cells, and tissues or organs derived therefrom. Exemplary methods of hematopoietic differentiation of iPS cells may include, for example, methods disclosed by U.S. Application No. 61/088,054 and No. 61/156,304, both incorporated herein by reference in their entirety, or embryoid body (EB) based methods (Chadwick et al., 2003; Ng et al., 2005). Fibronectin differentiation methods may also be used for blood lineage differentiation, as exemplified in Wang et al., 2007. Exemplary methods of cardiac differentiation of iPS cells may include embryoid body (EB) methods (Zhang, et al., 2009), OP9 stroma cell methods (Narazaki et al., 2008), or growth factor/chemical methods (see U.S. Patent Publn. 20080038820, 20080226558, 20080254003 and 20090047739, all incorporated herein by reference in their entirety).

A. Liver Cells

Hepatocytes can be differentiated from pluripotent stem cells such as hES cells using an inhibitor of histone deacetylase, as described in U.S. Pat. No. 6,458,589 and PCT publication WO 01/81549 (Geron Corporation). Undifferentiated pluripotent stem cells may be cultured in the presence of an inhibitor of histone deacetylase. In an exemplary method, differentiation is initiated with 1% DMSO, then with 2.5 mM of the histone deacetylase inhibitor n-butyrate. The cells obtained can be matured by culturing 4 days in a hepatocyte culture medium containing n-butyrate, DMSO, plus growth factors such as EGF, hepatocyte growth factor, and TGF-α.

Staged protocols for differentiating pluripotent stem cells such as hES cells into hepatocytes are described in US 2005/0037493 A1 (Geron Corp.). Cells are cultured with several combinations of differentiation and maturation agents in sequence, causing the pluripotent stem cells such as hES cells to differentiate first into early endoderm or hepatocyte precursors, and then to mature hepatocyte-like cells.

Differentiation into endoderm-like cells can be initiated using either butyrate, DMSO or fetal bovine serum, optionally in combination with fibroblast growth factors. Differentiation can then continue using a commercially available hepatocyte culture medium, including factors such as hepatocyte growth factor (HGF), epidermal growth factor (EGF), and/or bone morphogenic protein (e.g., BMP-2, 4, or 7) in various combinations. Final maturation may be enhanced by the presence of agents such as dexamethazone or Oncostatin M. An illustration of the "DMSO Protocol" from US 2005/0037493 A1, as applied to the reporter hepatocytes of this invention, is provided below in Example 3. In a refined hepatocyte differentiation protocol, differentiation is initiated using a protein with Activin activity, typically in the presence of or sequentially with other factors like butyrate and/or DMSO (Example 6). The cells can then be matured in stages, using HGF, EGF, and/or BMP, enhanced by the presence of agents such as dexamethazone followed by Oncostatin M.

Hepatocytes in certain aspects of this invention can be made by culturing pluripotent stem cells or other non-hepatocytes in a medium under conditions that increase the intracellular level of hepatocyte programming factors to be sufficient to promote programming of the cells into hepatocytes (see U.S. Application No. 61/323,689, incorporated herein by reference). The medium may also contain one or more hepatocyte differentiation and maturation agents, like various kinds of growth factors. However, by increasing the intracellular level of hepatocyte programming transcription factors, aspects of the present invention bypass most stages toward mature hepatocytes without the need to change the medium for each of the stages. Therefore, in view of the advantages provided by the present invention, in particular aspects, the medium for culturing cells under hepatocyte programming may be essentially free of one or more of the hepatocyte differentiation and maturation agents, or may not undergo serial change with media containing different combination of such agents.

These agents may either help induce cells to commit to a more mature phenotype or preferentially promote survival of the mature cells—or have a combination of both these effects. Hepatocyte differentiation and maturation agents illustrated in this disclosure may include soluble growth factors (peptide hormones, cytokines, ligand-receptor complexes, and other compounds) that are capable of promoting the growth of cells of the hepatocyte lineage. Non-limiting examples of such agents include but are not limited to epidermal growth factor (EGF), insulin, TGF-α, TGF-β, fibroblast growth factor (FGF), heparin, hepatocyte growth factor (HGF), Oncostatin M (OSM), IL-1, IL-6, insulin-like growth factors I and II (IGF-I, IGF-2), heparin binding growth factor 1 (HBGF-1), and glucagon. The skilled reader will already appreciate that Oncostatin M is structurally related to Leukemia inhibitory factor (LIF), Interleukin-6 (IL-6), and ciliary neurotrophic factor (CNTF).

An additional example is n-butyrate, as described in previous patent disclosures (U.S. Pat. No. 6,458,589, U.S. Pat. No. 6,506,574; WO 01/81549). Homologs of n-butyrate can readily be identified that have a similar effect, and can be used as substitutes in the practice of this invention. Some homologs have similar structural and physicochemical properties to those of n-butyrate: acidic hydrocarbons comprising 3-10 carbon atoms, and a conjugate base selected from the group consisting of a carboxylate, a sulfonate, a phosphonate, and other proton donors. Examples include isobutyric acid, butenoic acid, propanoic acid, other short-chain fatty acids, and dimethylbutyrate. Also included are isoteric hydrocarbon sulfonates or phosphonates, such as propanesulfonic acid and propanephosphonic acid, and conjugates such as amides, saccharides, piperazine and cyclic derivatives. A further class of butyrate homologs is inhibitors of histone deacetylase. Non-limiting examples include trichostatin A, 5-azacytidine, trapoxin A, oxamflatin, FR901228, cisplatin, and MS-27-275. Another class of agents is organic solvents like DMSO. Alternatives with similar properties include but are not limited to dimethylacetamide (DMA), hexmethylene bisacetamide, and other polymethylene bisacetamides. Solvents in this class are related, in part, by the property of increasing membrane permeability of cells. Also of interest are solutes such as nicotinamide.

The term "hepatocyte" or "hepatocyte lineage cell" as used in this disclosure means a cell that has one or more, preferably at least three, and more preferably five or seven of the following characteristics: $\alpha_1$-antitrypsin; asialoglycoprotein, glycogen storage, cytochrome P450 enzyme expression; glucose-6-phosphatase activity, low to negligible α-fetoprotein, and morphological features of hepatocytes (cuboidal cells, possibly with canalicular spaces between them). Other features of mature hepatocytes isolated from human liver may be present, but are not required to qualify cells as hepatocytes within this definition. Assay methods for identifying cell markers are detailed in U.S. Pat. No. 6,458,589. A "hepatocyte" of this invention may be but is not necessarily obtained by differentiating human embryonic stem cells, unless this is explicitly required.

In the context of drug screening, the user may also wish to test the activity of particular drug metabolizing enzymes, such as cytochrome P450 enzymes. A convenient way of surveying the activity of cytochrome P450 is to combine the cells with a "cassette" of substrates: such as midazolam (metabolized by CYP3A4), tolbutamide (metabolized by CYP2C9), phenacetin (CYP1A2), and bufuralol (CYP2D6). Activity can be quantitated as being about 0.1, 1, or 10 times that of a reference cell line, such as HepG2 cells. A convenient way of monitoring metabolites of all the drugs in the cassette simultaneously is by GCMS. If desirable, the cells can be treated with compounds such as dexamethazone or Rifampicin before or during use in drug screening, so as to increase cytochrome P450 expression or activity in the cells.

B. Nerve Cells

Neural cells can be generated from pluripotent stem cells such as hES cells according to the method described in U.S. Pat. No. 6,833,269; Carpenter et al., 2001; and WO 03/000868 (Geron Corporation). Undifferentiated hES cells or embryoid body cells are cultured in a medium containing one or more neurotrophins and one or more mitogens, generating a cell population in which at least ~60% of the cells express A2B5, polysialylated NCAM, or Nestin and which is capable of at least 20 doublings in culture. Exemplary mitogens are EGF, basic FGF, PDGF, and IGF-1. Exemplary neurotrophins are NT-3 and BDNF. The use of TGF-β Superfamily Antagonists, or a combination of cAMP and ascorbic acid, can be used to increase the proportion of neuronal cells that are positive for tyrosine hydroxylase, a characteristic of dopaminergic neurons. The proliferating cells can then be caused to undergo terminal differentiation by culturing with neurotrophins in the absence of mitogen.

Oligodendrocytes can be generated from pluripotent stem cells such as hES cells by culturing them as cell aggregates, suspended in a medium containing a mitogen such as FGF, and oligodendrocyte differentiation factors such as triiodothyronine, selenium, and retinoic acid. The cells are then plated onto a solid surface, the retinoic acid is withdrawn, and the population is expanded. Terminal differentiation can be effected by plating on poly-L-lysine, and removing all growth factors. Populations can be obtained in which over 80% of the cells are positive for oligodendrocyte markers NG2 proteoglycan, A2B5, and PDGFRα, and negative for the neuronal marker NeuN. See PCT publication WO 04/007696 and Keirstead et al., 2005. Derivation of retinal pigment epithelial cells has also been reported (Klimanskaya et al., 2004).

C. Heart Cells

The iPS cells provided herein may be differentiated into cardiomyocytes according to methods described in US 2011/0097799 (incorporated herein by reference). Cardiomyocytes or cardiomyocyte precursors can be generated from pluripotent stem cells such as hES cells according to the method provided in WO 03/006950. In a similar fashion, the iPS cells may be cultured in suspension with fetal calf serum or serum replacement, and optionally a cardiotrophic factor that affects DNA-methylation, such as 5-azacytidine. Alternatively, cardiomyocyte clusters can be generated by culturing on a solid substrate with Activin A, followed by culturing with a bone morphogenic protein like BMP4, and optionally by further culturing with an insulin-like growth factor like IGF-1. If desired, spontaneously contracting cells can then be separated from other cells in the population, by density centrifugation.

Further process steps can include culturing the cells so as to form clusters known as Cardiac Bodies™, removing single cells, and then dispersing and reforming the Cardiac Bodies™ in successive iterations. Populations are obtained with a high proportion of cells staining positive for cTnI, cTnT, cardiac-specific myosin heavy chain (MHC), and the transcription factor Nkx2.5. See WO 03/006950, Xu et al., 2002; and US 2005/0214939 A1 (Geron Corporation).

D. Other Cell Types

Islet cells can be differentiated from pluripotent stem cells such as hES cells (WO 03/050249, Geron Corp.) by initiating differentiation by culturing in a medium containing a combination of several factors selected from Activin A, a histone deacetylase inhibitor (such as butyrate), a mitogen (such as bFGF); and a TGF-β Superfamily antagonist (such as noggin). The cells can then be matured by culturing with nicotinamide, yielding a cell population in which at least 5% of the cells express Pdx1, insulin, glucagon, somatostatin, and pancreatic polypeptide. Cell clusters may form buds enriched for insulin producing cells, which can be recovered by filtering. See WO 03/050249 (Geron Corp.).

Hematopoietic cells can be made by coculturing pluripotent stem cells such as hES cells with murine bone marrow cells or yolk sac endothelial cells was used to generate cells with hematopoietic markers (U.S. Pat. No. 6,280,718). Hematopoietic cells can also be made by culturing stem cells with hematogenic cytokines and a bone morphogenic protein, as described in US 2003/0153082 A1 and WO 03/050251 (Robarts Institute). Method for hematopoietic cell differentiation from iPS cells provided herein may be described in US 2010/0216181 and US 2010/0279403 (all incorporated herein by reference).

Mesenchymal progenitors and fibroblasts can be generated from pluripotent stem cells such as hES cells according to the method described in WO 03/004605. hES-derived mesenchymal cells can then be further differentiated into osteoblast lineage cells in a medium containing an osteogenic factor, such as bone morphogenic protein (particularly BMP4), a ligand for a human TGF-β receptor, or a ligand for a human vitamin D receptor (WO 03/004605 Sotile et al., 2003). US 2004/0009589 A1 (Iskovitz-Elder et al.) and US 2003/0166273 A1 (Kaufman et al., Wisconsin) report endothelial cells derived from human embryonic stem cells. Chondrocytes or their progenitors can be generated by culturing stem cells in microaggregates with effective combinations of differentiation factors listed in WO 03/050250 (Geron Corp.).

Other differentiation methods known in the art or subsequently developed can be used in conjunction with this invention to create engineered cells representative of other tissues.

VIII. Examples

The following examples are included to demonstrate preferred embodiments of the invention. It should be appreciated by those of skill in the art that the techniques disclosed in the examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Engineering Maxi EBV Particles for Reprogramming

If EBV-positive B cells prove more receptive to reprogramming, then B cells negative for EBV may be made more susceptible by infecting them with engineered EBV particles that may encode reprogramming factors. EBV is a member of the human herpesvirus family that is capable of packaging very large amounts of DNA (≤165 kb), a desirable feature from the standpoint of molecular engineering. We can take advantage of the features of EBV to generate recombinant EBV-based vectors that, in combination with a helper cell line, can be used to create Maxi-EBV particles that serve as vehicles for delivering proteins essential for reprogramming, transformation, etc. (Wendtner et al., 2003; Delecluse et al., 1999; Delecluse et al., 1998; Hettich et al., 2006). The following is an outline of the process that may be needed to derive such particles:

First, to generate an infection B cell line, a virus-defective helper cell line is created from 293 cells: complete EBV genome (165kb) is cloned onto a prokaryotic replicon that also carries marker genes driven by eukaryotic promoters (8-10 wks); extrachromosomal EBV genome devoid of TR sequence is introduced into 293 cells that provides all the packaging functions for the EBV vector; and a population of clones resulting from transfection is maintained. A "non-transforming" mini EBV plasmid is engineered to encode the following: Selection (Hygromycin, GFP, etc), Terminal repeats of EBV (TR), two origins of replication (oriLyt and oriP), EBNA-1. The mini EBV plasmid may optionally include reprogramming genes and/or dominant negative derivatives of EBNA-1 with/without conditional operators or promoters. Then packaged mini EBVs are created by: transiently transfecting engineered virus-defective cells (above) with mini EBV plasmid and a viral transactivator; harvesting, purifying, and concentrating supernatant; establishing a test cell line for infection and screening for Hyg-resistance and/or GFP-positive clones; and establishing larger scale production and determining viral titers. After that primary B cells are infected by incubating primary B cells with mini EBV virions followed by assessing efficiency of infection 48 hours post (if fluorescence is used as an indicator)

Example 2

Reprogramming Lymphoblastoid Cells Lines (LCLs) and Standard B Cells

1) Drive Mature B Cell Population Towards a Progenitor State or Isolate a Pax-5-Pro-B Cell Progenitor Cell Type for Reprogramming Trials.

Dedifferentiation of a mature B cell population to a progenitor cell type might need inhibition of Pax-5, Blimp1, Oct2 and Bob-1 or up-regulation of C/EBPα.

The following reagents/treatments are used to down regulate Pax-5 expression:

Cells are treated with Glucocorticoids (GCs) like Prednisolone sodium succinate or SN38 or SU11274 (Kanteti et al., 2009; Marie-Cardine et al., 2008) to down regulate Pax-5 expression (Rahman et al., 2001). The surviving cells are placed in IL-7 containing media to support the growth of pro-B cells.

B cells are treated with antisense RNA, small interfering RNA, ribozymes or transfected with expression cassettes encoding Pax-5-inhibiting oligonucleotide molecules. The same approach can be used for Blimp1, Oct2 and Bob-1. Down regulating one or more of these genes may enhance reprogramming.

As an alternative to or in addition to downregulation of Pax-5, Blimp1, Oct2 or Bob-1, mature adult B cells are infected with retrovirus encoding C/EBPα gene. C/EBPα up-regulation can steer the cells to a myeloid progenitor like state and more receptive to reprogramming factors. This strategy has been outlined by Jaenisch et al. Alternatively, an expression cassette for C/EBPα could be introduced by electroporation.

2) Identify and Isolate a Pax-5 Devoid Pro-B Cell Progenitor Cell Type for Reprogramming Trials.

This approach could involve the isolation and purification of a lymphoid progenitor cells co-expressing the antigens CD34, CD38 and CD10.

$CD34^+CD10^+CD19^-$ progenitor B cells are devoid of Pax-5 expression. Hence this population could be a target cell type for reprogramming.

The pro-B cells can be expanded in culture utilizing a combination of stem cell factor (SCF), interleukin-2 (IL-2), interleukin-7 (IL-7), interleukin-15 (IL-15), Flt3 ligand (FL) and thymic stromal lymphopoietin (TSLP).

A second strategy will involve the isolation of transitional B cells from peripheral blood. Transitional B cells mark the crucial link between bone-marrow (BM) immature and peripheral mature B cells that are identified as CD19(+) CD24 (high) CD38(high)expressing cells. These cells represent approximately 4% of B cells in healthy adult peripheral blood (Chung et al., 2003).

The frequency of transitional B cells is upregulated in immune disorders and in HIV patients. This cell type can be a target cell for generating iPS cells from disease specific donors.

Transfection of immature B cell (Pax-5⁻) cells, or a lymphoid progenitor cells or transitional B cells with plasmids containing the reprogramming factors (Oct4, Sox2, Nanog or Klf4, optionally Lin28 or c-Myc; see FIGS. 1A-1B) can be used for generating iPSCs.

3) Reprogramming Primary B Cells Transformed with EBV:

The efficient transformation capacity of EBV of primary B cells is routinely performed to establish and bank lymphoblastoid cell lines (LCLs) in vitro. The Epstein-Barr virus (EBV) latency III program imposed by viral proteins EBNA-2 and LMP-1 is directly responsible for transformation of B cells in vitro.

LCLs express increased levels of c-Myc, which is at least in part responsible for EBV-driven B-cell proliferation. LCLs also reveal induction of NF-KappaB which in turn is responsible for protection from apoptosis.

c-Myc is a reprogramming factor. Transfection of LCLs with reprogramming factors without c-Myc or SV40-T antigen can be used to generate iPSCs.

Inhibitors of NF-KappaB and p53 can be used as supplements for reprogramming trials with. LCLs.

4) Post Transfection Care of Recipient Cells

Recipient B cells can be placed in media supporting surviving B cells. Addition of BLyS, BAIT (members of the TNF family of cytokines, essential survival factor for B cells) or CD40 ligand could also augment the proliferation of B cells containing the reprogramming factors for the first few days post transfection (Fu et al., 2009).

Reprogramming trials using LCLs could be performed under Serum Free conditions. The cells can be placed on irradiated MEFs or on Matrigel and fed for 30 days using conditioned media from MEFs or under MEF-free conditions using enriched media containing small molecules.

Several conditions that can be used to facilitate chemical MEF-Free reprogramming methods can be included.

Example 3

Reprogramming Lymphoblastoid Cell Lines (LCLs) without Preemptive Inhibition of Pax-5 or Over-Expression of C/EBPα-R Gene Using Defined Feeder-Free Conditions The primary LCLs were obtained and expanded in RPMI medium containing 10-20% FBS. The cultured LCLs were transfected via electroporation with EBV-based episomal vectors containing reprogramming factors as described below.

The reprogramming was performed using three LCL cell lines transduced with three sets of reprogramming factors: 7 reprogramming factors (Oct4, Sox2; Nanog, Lin28, Klf4, c-Myc, SV40 Large T antigen), 5 reprogramming factors (Oct4, Sox2; Nanog, Lin28 and SV40 Large T antigen) or 4 reprogramming factors (Oct4, Sox2; Nanog and SV40 Large T antigen).

The optimal concentration of DNA for reprogramming was between 1-2 μg. The efficiency of transfection was estimated by using a relevant plasmid backbone containing a fluorescent marker like GFP.

The efficiency of transfection for GFP-containing plasmids was between 40-95%. The efficiency of transfection for plasmids containing GFP along with the reprogramming factors was between 2-20%. The LCLs are a very favorable cell type for oriP-containing plasmids.

Presence of MEFs resulted in uncontrolled proliferation of untransfected cells. Therefore, the entire process was performed under feeder-free conditions. After transfection, cells were placed on a feeder-free matrix to promote attachment. The matrix component may comprise Matrigel™, fibronectin, RetroNectin® (a fragment of fibronectin), combination of retronectin with Matrigel, CellStart™, collagen or any component that could replace a feeder layer. The viability of cells post-transfection was about 5-50%.

The transfected cells were placed in media containing DMEM/F12, N2 supplement, B27 supplement, 1% NEAA, 1% Glutamax, 0.1 mM β-mercaptoethanol, 100 ng/mL zebrafish basic fibroblast growth factor (zbFGF), 0.5 μM PD0325901, 3 μM CHIR99021, 0.5 μM A-83-01, 1000 U/mL human recombinant LIF, and 10 μM HA100 (CHALP medium). The cells were fed with fresh media every other day for the first week post transfection. During the second week, half of the spent media was gently removed from each well and the cells were fed with fresh media every other day. The media exchanges were performed very gently to prevent dislodging of cells that were attached to the culture vessel surface. Two to three weeks post transfection, the cultures were slowly transitioned to mTeSR1 or TeSR2. The cultures were fed with fresh TeSR media every other day for the next 2-3 weeks The levels of Pax-5 expression were determined in untransfected and transfected LCLs. Pax-5 levels were quantified by intracellular flow cytometry 4-6 days post transfection. Pax-5 expression in untransfected LCLs was between 60-85%. LCLs transfected with reprogramming plasmids revealed a decreased expression of Pax-5 (10-60%). Various combinations of plasmids displayed varying levels of Pax-5 downregualtion (FIGS. 6A-6D). The combinations displaying the highest inhibition of Pax-5 expression generated iPSCs. The exact mechanism by which the reprogramming factors downregulate Pax-5 is not known. Episomal feeder-free reprogramming in the presence of small molecules leads to downregulation of endogenous Pax-5 expression, which in turn may facilitate the generation of LCL derived iPSCs. A closer analysis revealed the threshold of Pax-5 expression that favors the reprogramming process is between 10-30%. Reprogramming conditions that led to a 65-90% Pax-5 inhibition resulted in iPSCs, while suboptimal inhibition between 20-50% did not favor reprogramming of LCLs to iPSCs.

LCL cultures were transfected with plasmids encoding the C/EBPα gene. The presence of the transfected gene was confirmed by PCR. C/EBPα over-expressing cells were selected by placing the cells in G418 containing media. Following selection, the cells were transfected with reprogramming factors. A second strategy was to transfect LCLs with plasmids encoding C/EBPα gene along with the reprogramming factors.

Adherent colonies appeared in the wells and the morphology of LCLs transitioned from a suspension cell type to an adherent cell type. The adherent colonies were picked and propagated on Matrigel coated plates. The colonies slowly began to acquire the classic morphology of iPS-like colonies. Live staining with Tra-1-60 was performed and confirmed the iPS status of the colony (FIGS. 2A-2B, 3A-3B, 4A-4B, and 4A-5B). LCLs transfected with the reprogramming factors alone revealed iPS colonies. Over-expression of the C/EBPα gene prior to or inhibition of Pax-5 expression prior to reprogramming was not essential to reprogram LCLs.

Placing transfected LCLs on irradiated MEFs in the presence of hESC media or MEF conditioned medium resulted in the proliferation of untransfected LCLs. The cultures expanded rapidly post transfection in the presence of feeders and KOSR-containing media. Feeder-free conditions favored the reprogramming of B cells.

Example 4

Strategies to Remove Residual EBV from the iPS Colonies

EBV preferentially infects B cells (e.g., producing lymphoblastoid lines) and must provide a selective advantage to the host cell because it is not lost from them. Therefore, one possibility is that plasmids bearing the oriP replicon of EBV may promote gene expression and plasmid retention more optimally within these cells than other cell types for reprogramming. For example, the EBNA-1 already present within these infected cells would complement the newly introduced oriP plasmid encoding the reprogramming factors by promoting its retention and ensure sufficient time for expression to ensure reprogramming. Once the transition to iPS cells occur, it is likely that the endogenous EBV and the transfected oriP-based plasmid would be lost from the cells naturally since they are not likely to provide a selective advantage to the cells. On the other hand, the rate of loss of those episomes may be too slow to be desirable.

There are three potential ways to address either of these possibilities and force the loss of EBV and its cognate oriP-based DNA from cells. First, the transfected oriP-based plasmid will likely not provide a selective advantage to resulting iPS clones and therefore will be naturally lost from cells over time during cell division. A molecular screen would be used to identify clones that are successfully free of the plasmid. Second, the plasmids can be fitted with a cassette to select against cells that still retain the transfected oriP-based plasmid by encoding a selection marker such as drug resistance, fluorescence, or cell surface marker (i.e. hygromycin, GFP, CD4, etc). This approach, however, will not remove the endogenous EBV that may still reside in the host cell.

Therefore, the third approach is to fit the transfected DNA with a cassette encoding a derivative of EBNA-1 that functions as a dominant negative to inhibit the function of wild-type EBNA-1. Alternatively, EBNA-1 dominant negative Tat-Fusion protein (Tat is a protein transduction domain) could be engineered and supplemented to the iPS cells.

A derivative of EBNA-1 that lacks its amino-terminal half but retains its ability to localize to the nucleus and bind DNA is a well-studied inhibitor of EBNA-1 that facilitates the loss of oriP-containing plasmids from cells (Kirchmaier and Sugden, 1997; Kennedy et al., 2003; Mack and Sugden, 2008). This EBNA-1 DNA binding domain (DBD) mutant competes with wild-type EBNA-1 by forming heterodimers, binds to sites within the oriP DNA, and inhibits wild-type EBNA-1's ability to support replication of the oriP-containing plasmids resulting in loss of the plasmid DNA. Because the oriP replicon is found within wild-type EBV plasmids, they too will be lost from cells in the presence of the DBD protein. Therefore, once reprogramming has successfully occurred, the residual oriP-based plasmid from the initial transfection can be induced to express the EBNA-1 DBD domain (FIGS. 1A-1B) or it can be introduced from an independent plasmid.

Figure 1B:
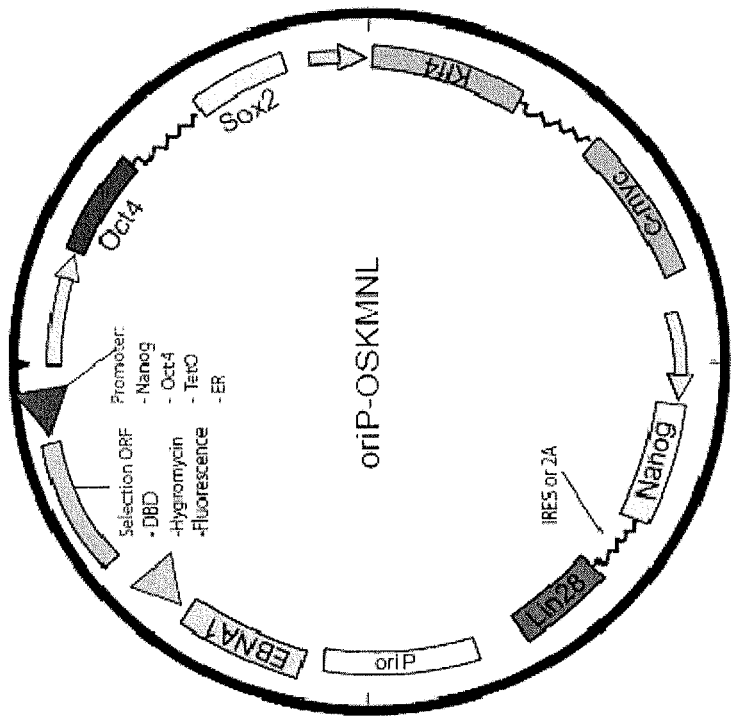
Figures 2A, 2B:
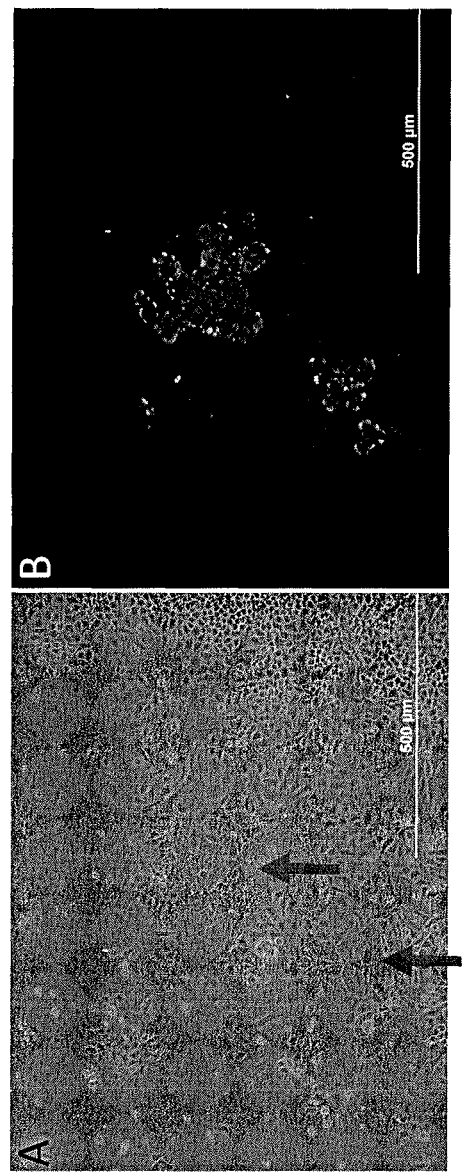
FIGS. 2A-2B: Tra-1-60 live staining to confirm iPS status at 40 days post transfection. A LCL was transfected with reprogramming factors and placed on a matrix (Matrigel and Retronectin) in the CHALP medium for 15 days, followed by mTeSR-1 medium for 25 days (FIG. 2A). Staining with Tra-1-60 in FIG. 2B confirmed the presence of iPS cells.
Figures 3A, 3B:
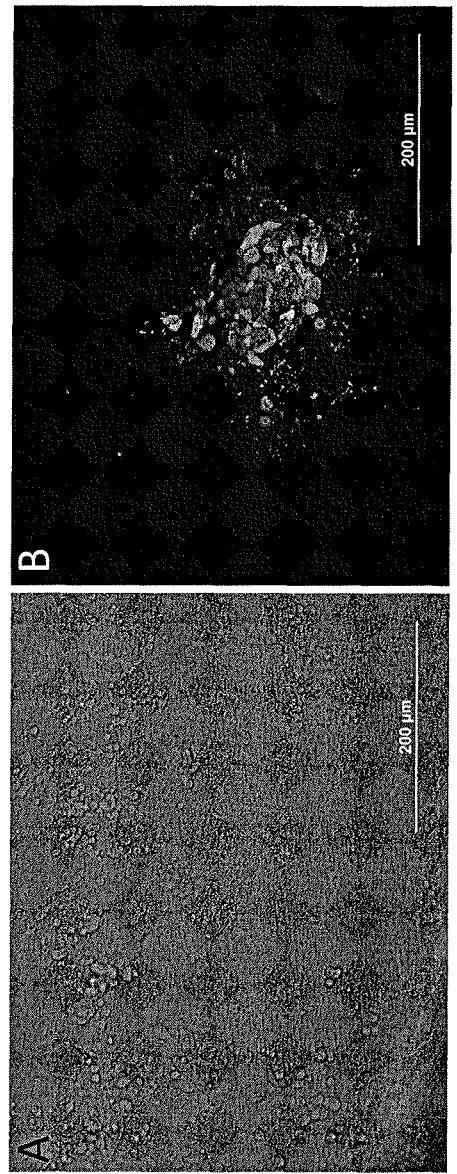
FIGS. 3A-3B: Tra-1-60 live staining to confirm iPS status at 46 days post transfection. A LCL was transfected with reprogramming factors and placed on a matrix (Matrigel) in the CHALP medium for 15 days, followed by mTeSR-1 medium for 31 days (FIG. 3A). Staining with Tra-1-60 in FIG. 3B confirmed the presence of iPS cells.
Figures 4A, 4B:
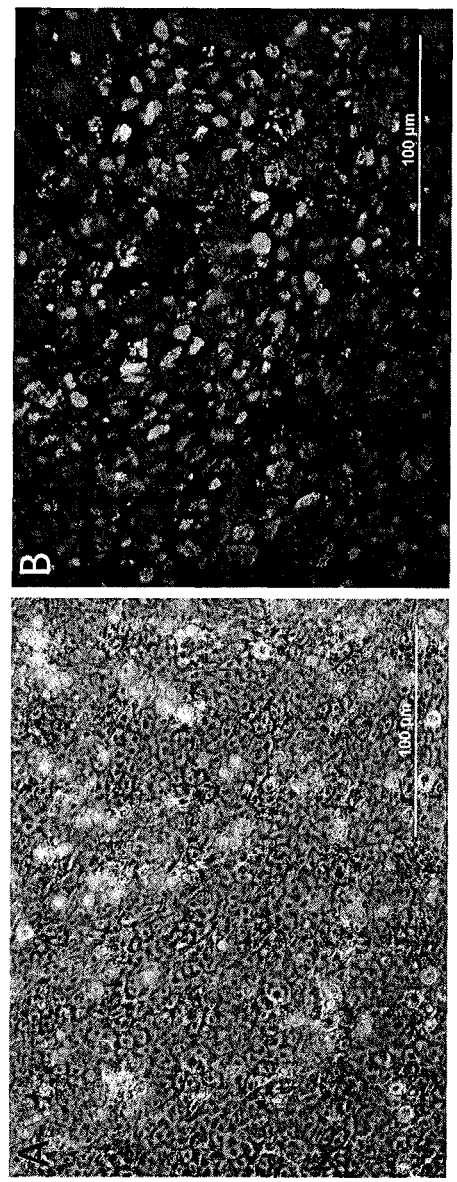
FIGS. 4A-4B: Tra-1-60 live staining to confirm iPS status at 29 days post transfection. A LCL was transfected with reprogramming factors and placed on a matrix (Matrigel) in the CHALP medium for 20 days, followed by mTeSR-1 medium for 9 days (FIG. 4A). Staining with Tra-1-60 in FIG. 4B confirmed the presence of iPS cells.
Figures 5A, 5B:
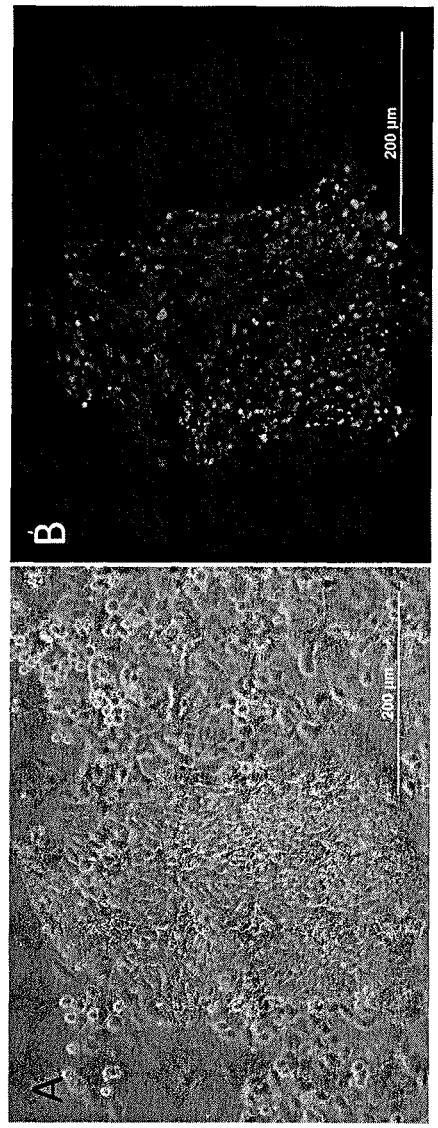
FIGS. 5A-5B: Tra-1-60 live staining to confirm iPS status at 48 days post transfection. A LCL was transfected with reprogramming factors and placed on a matrix (Matrigel) in the CHALP medium for 15 days, followed by mTeSR-1 medium for 33 days (FIG. 5A). Staining with Tra-1-60 in FIG. 5B confirmed the presence of iPS cells.
Figure 6A:
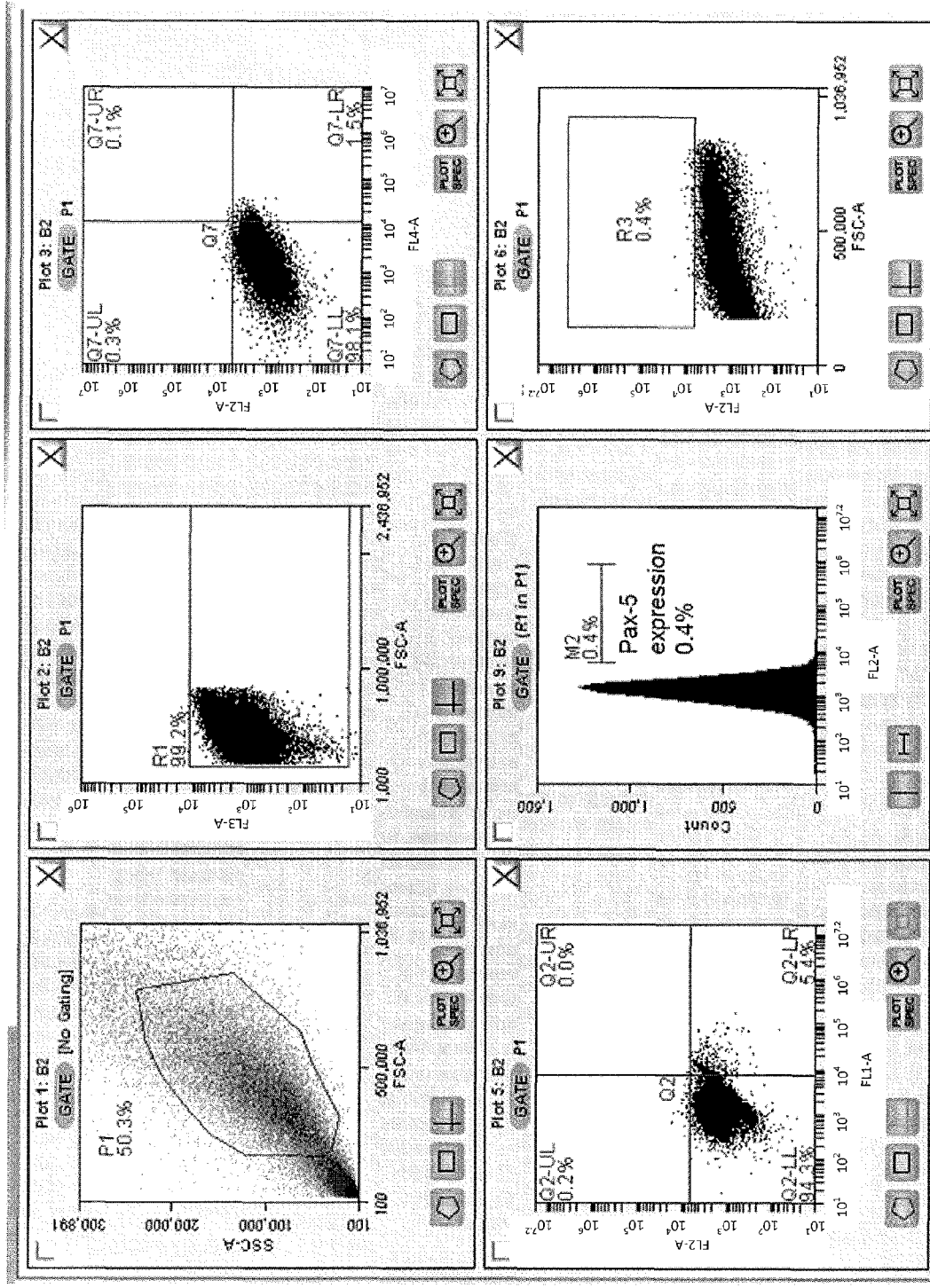
FIGS. 6A-6D: Transfection of reprogramming factors inhibits Pax-5 expression.
Figure 6B:
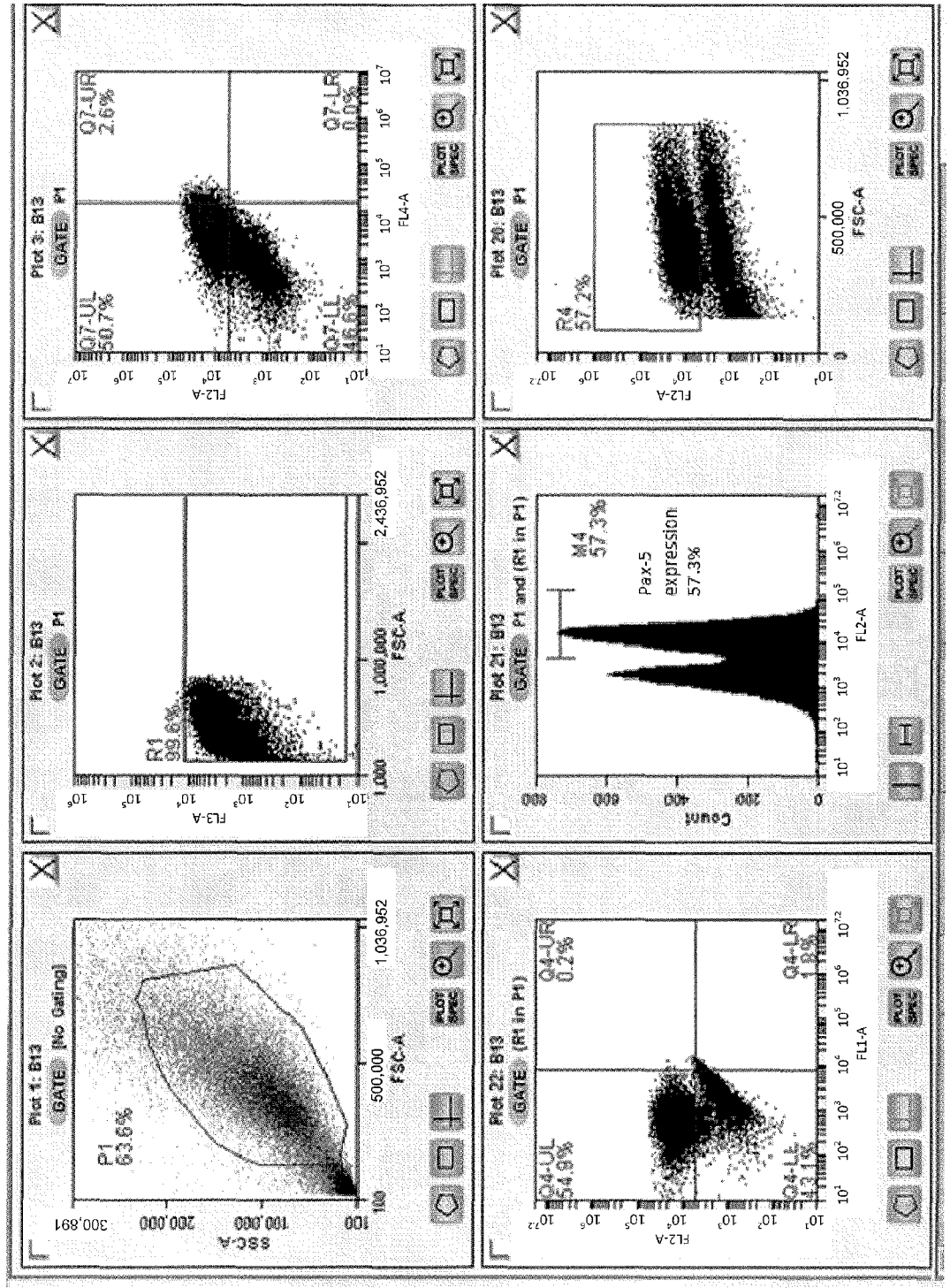
Figure 6C:
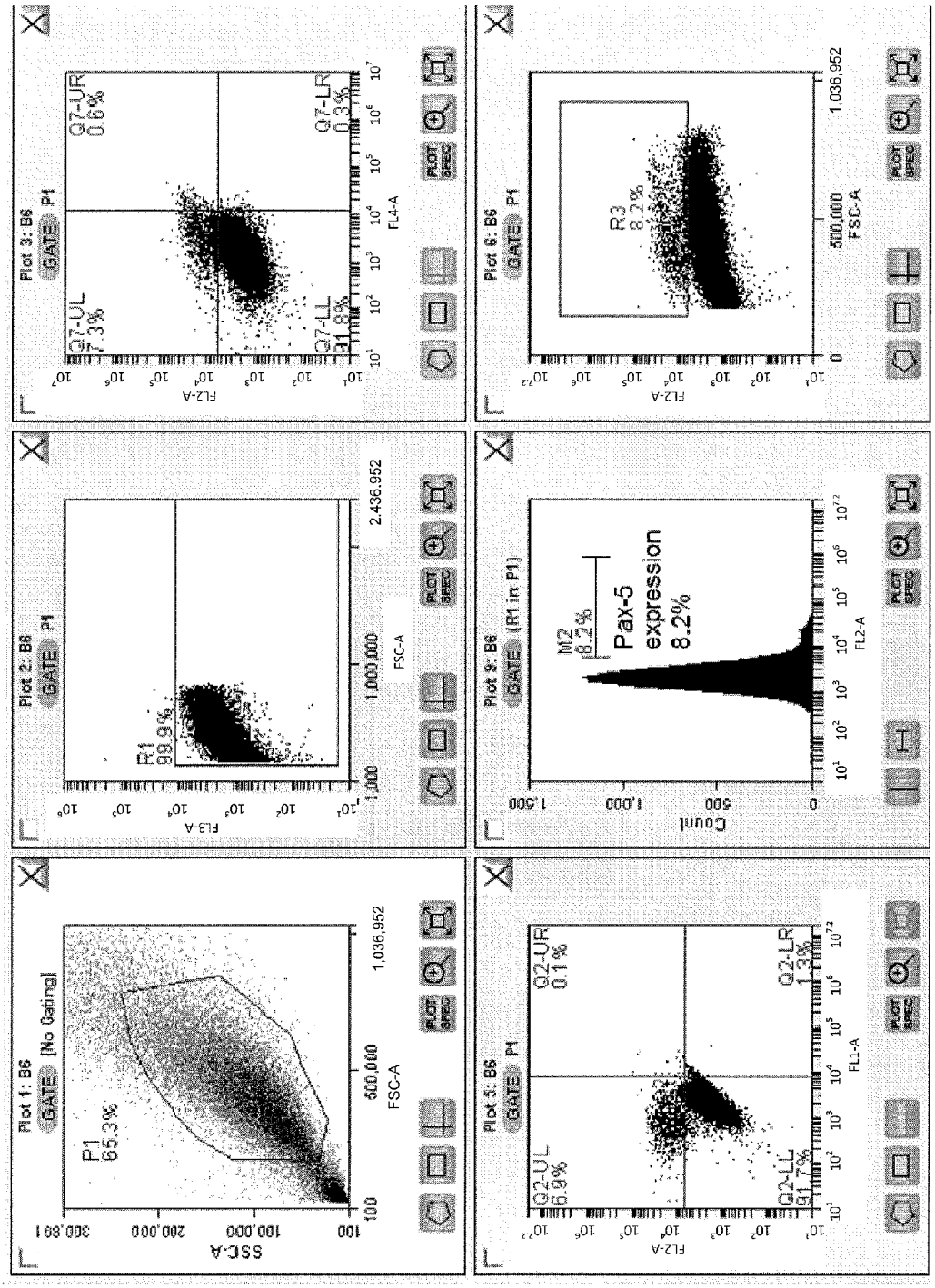
Figure 6D:
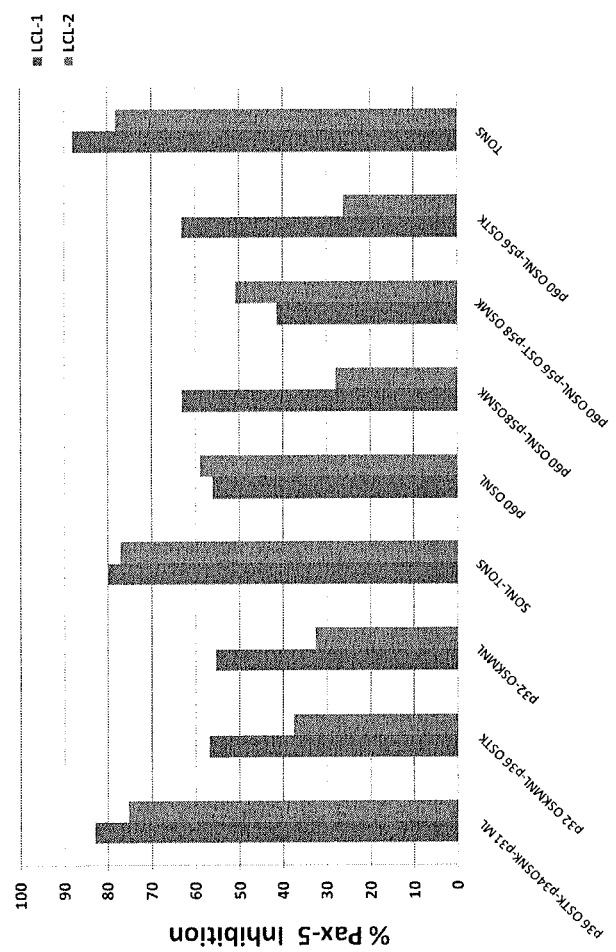

The expression of cassettes encoding selection or a dominant negative derivative of EBNA-1 will be driven by a conditional promoter (FIGS. 1A-1B). The promoter will be responsive to estrogen, tetracycline, or the presence of Nanog or Oct4 proteins. The estrogen receptor functions as a transcriptional regulator that translocates to the nucleus in response to estrogen where it binds to responsive elements within the DNA. It has the potential to be leaky but responds quickly in comparison to the tetracycline-based systems. The Tet-based system is advantageous due to its high degree of regulation and is less prone to leakiness. For example, the level of expression of our gene of interest would correlate with the level of doxycycline that is added to the system. An expression system that is conditionally based on the presence of Nanog or Oct4 ensures that the cell has acquired properties that are associated with pluripotency. Presumably, the higher the Oct4 or Nanog, then the higher the level of expression from the cassette encoding drug selection or the dominant negative derivative of EBNA-1.

Example 5

Additional Strategies to Remove Residual EBV from the iPS Colonies

Once the iPS colonies are formed, residual EBV can also be removed by a fourth approach by supplementing the media with the reagents and using the methods as detailed below. The surviving clones can be screened to demonstrate the absence of EBV.

The following strategies could be used to remove residual EBV from the iPS colonies:

Acyclovir [9-(2-hydroxyethoxymethyl) guanine], the first clinically useful drug effective against lytic replication of EBV.

Three nucleoside analogs, E-5-(2-bromovinyl)-2'-deoxyuridine, 1-(2-deoxy-2-fluoro-beta-D-arabinofuranosyl)-5-iodocytosine, and 1-(2-deoxy-2-fluoro-beta-D-arabinofuranosyl)-5-methyluracil are potent inhibitors of EBV replication in vitro (Lin et al., 1983).

beta-L-5-Iododioxolane uracil has potent anti-Epstein-Barr virus (EBV) activity (50% effective concentration=0.03 microM) with low cytotoxicity (50% cytotoxic concentration=1,000 microM). It exerts its antiviral activity by suppressing replicative EBV DNA and viral protein synthesis (Kira et al., 2000).

A combination of 3'-azido-3'-deoxythymidine, along with alpha and gamma interferon could be used to cure EBV from the recipient cells.

Supplementation of media with G-quadruplex-specific compounds TMPyP3, TMPyP4, and BRACO-19 can be used. These compounds block EBV proliferation and disrupt the ability of EBNA-1 to tether to metaphase chromosomes (Norseen et al., 2009).

Hsp90 inhibitors induce the death of established, EBV-transformed lymphoblastoid cell lines at doses nontoxic to normal cells, and this effect is substantially reversed when lymphoblastoid cell lines are stably infected with a retrovirus expressing a functional EBNA-1 mutant lacking the Gly-Ala repeats (Sun et al., 2010). iPS cells which retain EBV and wild-type EBNA-1 would be specifically targeted and selected against.

Since LCLs overexpress c-Myc, residual un-reprogrammed cells and partially reprogrammed iPS colonies can continue to express c-Myc. Inactivation of c-Myc by a chemical inhibitor (10058-F4) or conditional expression of dominant-negative c-Myc can be used to remove cells that have any expression of c-Myc.

Example 6

Lymphoblastoid B Cell Lines Reprogrammed to EBV-Free Induced Pluripotent Stem Cells Briefly, lymphoblastoid cell lines (LCLs) were obtained from Coriell Cell Repositories and maintained using RPMI1640 (Invitrogen) with 15% FBS (Hyclone). The cells were transfected using oriP/EBNA-1-based episomal vectors previously described (Yu et al., 2009; Yu et al., 2007). Post transfection the cells were placed in Matrigel-coated tissue culture plates (BD Biosciences) in reprogramming medium (RM) for 2-3 weeks Yu et al. (manuscript submitted December 2010) followed by maintenance in TeSR-2 Medium (Stem Cell Technologies) for additional 2 weeks. The iPSC-like colonies were initially handpicked and propagated using TeSR-2 medium on Matrigel coated plates. Characterization of four LCL-iPSCs was performed by flow cytometry, PCR and teratoma analysis (Yu et al., 2009). In vitro differentiations were performed to neural, hematopoietic, cardiac, and hepatocyte lineages, were performed according to protocols established during the development of iCell Cardiomyocytes™, iCell Hepatocytes™ and iCell Neurons™ (Cellular Dynamics International). The presence of EBV was assessed by RT-PCR, genomic DNA PCR and immunohistochemistry to detect the presence of EBNA-1 protein. The karyotype of LCL-iPSCs was analyzed by G banding (WiCell Research Institute). The genetic identity to the parental line confirmed by short tandem repeat (STR) analysis (Cell Line Genetics). IgGH receptor rearrangement analysis was performed on parental and LCL-iPSCs (Hematologics).

Figures 7A, 7B:
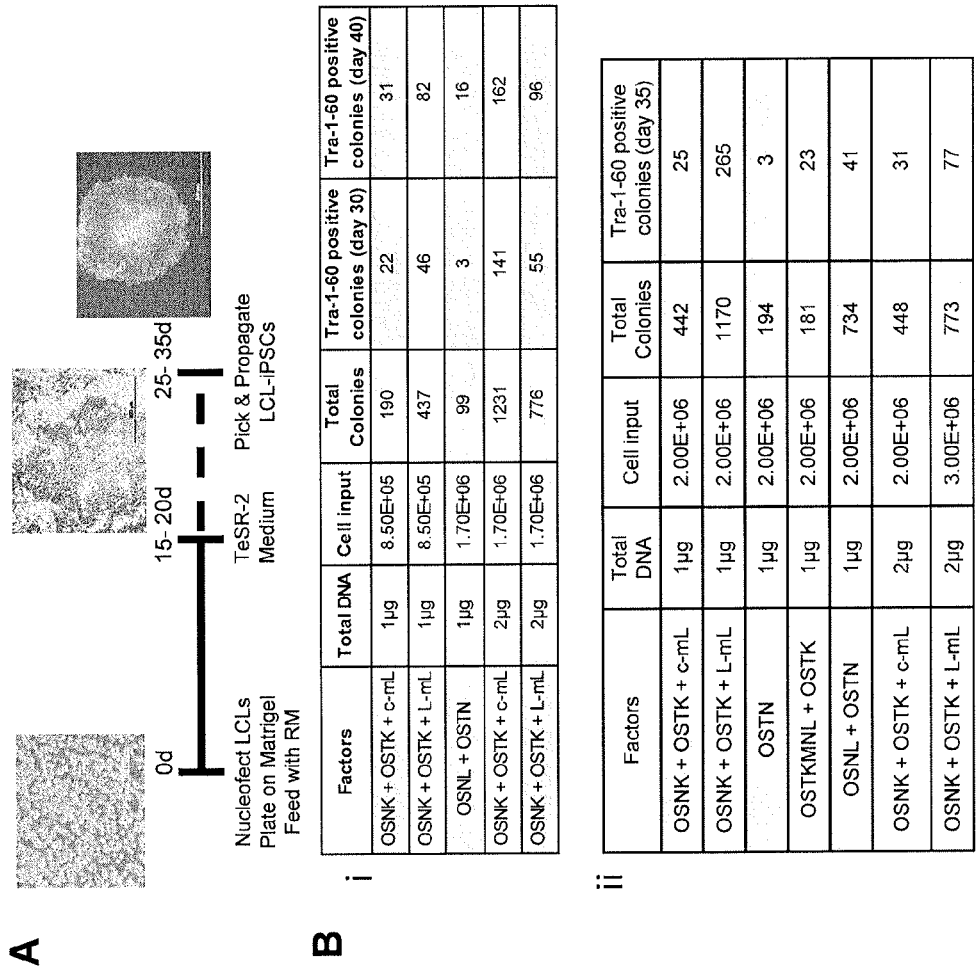
FIGS. 7A-7F: Derivation and characterization of LCL-iPSCs.
Figure 7C:
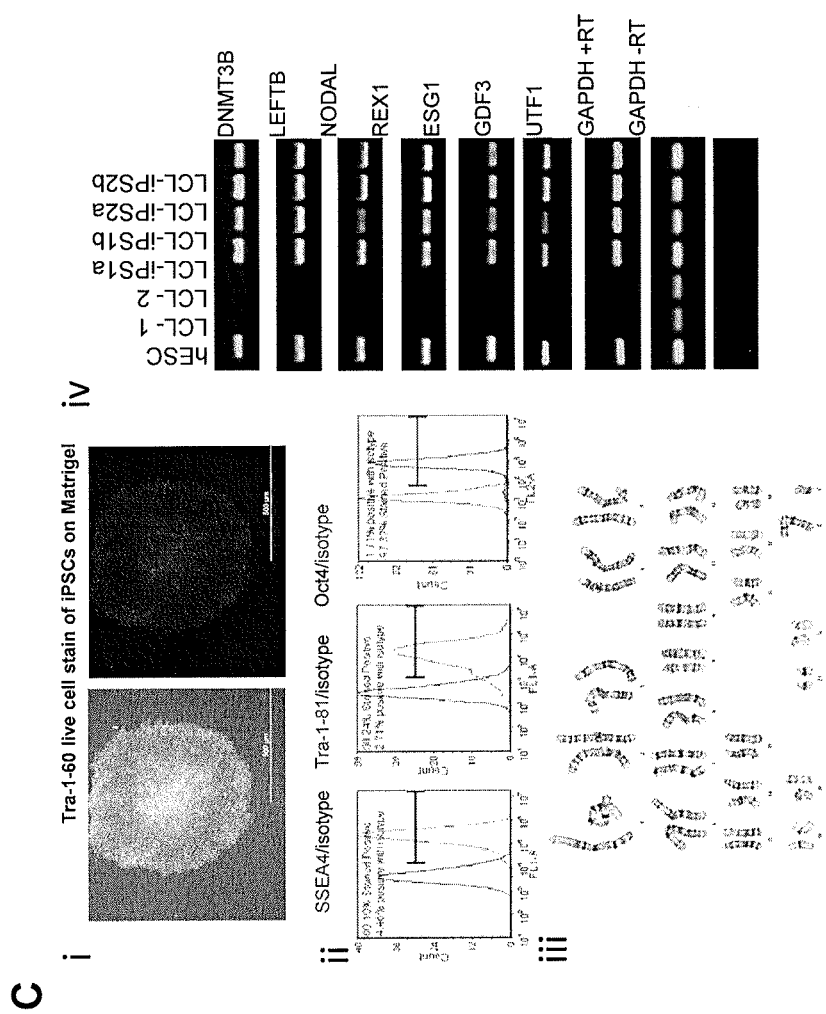

LCLs were reprogrammed via a single transfection of oriP/EBNA-1 plasmids encoding reprogramming genes under feeder-free conditions outlined by Yu et al. (manuscript submitted December 2010). Transfection efficiencies of 50-80% with a viability ranging from 50-70% were recorded with LCLs transfected with oriP/EBNA-1-GFP plasmids (data not shown). LCLs were placed on Matrigel-coated plates immediately after transfection, and cultured with reprogramming medium for 2-3 weeks. Adherent colonies were visible around 2 weeks post transfection (FIG. 7A) and the medium was then transitioned to TeSR-2. After culturing in TeSR-2 medium for about 2 weeks, the pluripotent status of the colonies was confirmed by live-cell staining of Tra-1-60 expression (FIG. 7Ci). Various doses and combinations of the reprogramming plasmids can reprogram LCLs (FIG. 7B). L-Myc and c-Myc demonstrated similar efficiencies of iPSC generation from LCLs. 3-11% of the total adherent colonies were confirmed to be iPSCs by Tra-1-60 staining. The number of Tra-1-60 positive colonies scored at 7 weeks was greater than the colonies scored at 5 weeks post transfection supporting the conversion of adherent colonies to authentic iPSCs. This was further confirmed by alkaline phosphatase staining (data not shown). Generation of LCL-iPSC by this method was more efficient than the average efficiency of iPSC generation from fibroblasts and keratinocytes by episomal reprogramming (Okita et al., 2010; Carey et al., 2009; Okita et a., 2008) as well as viral reprogrammed terminally differentiated murine B cells (Hanna et al., 2008), but not as efficient as episomal reprogramming of cord blood (Yu et al. manuscript submitted December 2010). Recent findings indicate that an 'open' chromatin state contributes to maintenance of pluripotency (Gaspar-Maia et al., 2011). EBNA-1 has been shown to orchestrate a broad rearrangement of the cellular transcriptional factors that maintain chromatin architecture and control viral replication. The pleotrophic effects of EBNA-1 induced during B-cell transformation and expression of other viral proteins may favor the reprogramming process in LCLs compared to primary cells (Sompallae et al., 2010).

Figure 7D:
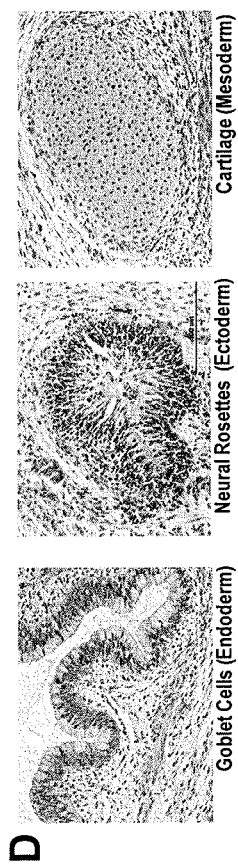
Figures 7E, 7F:
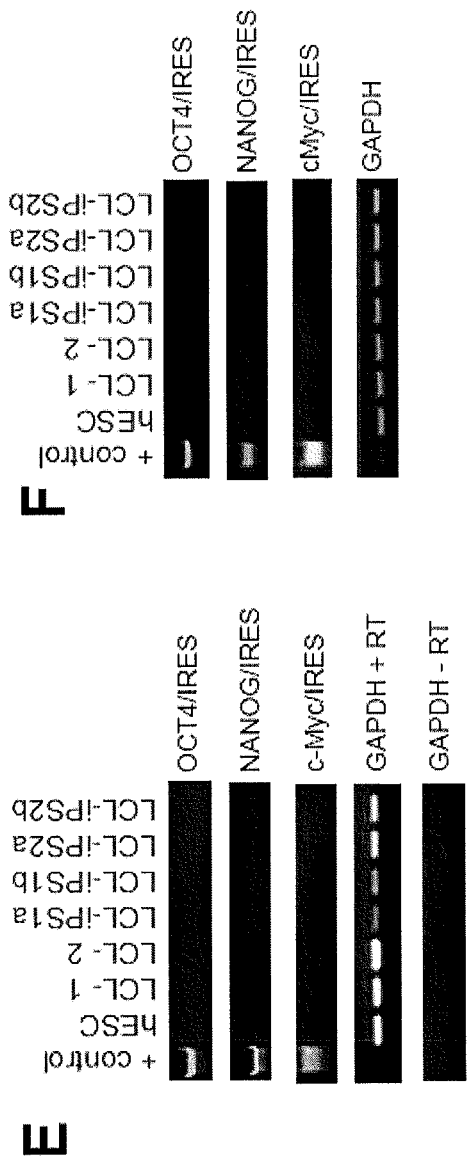
Figures 8A, 8B, 8C:
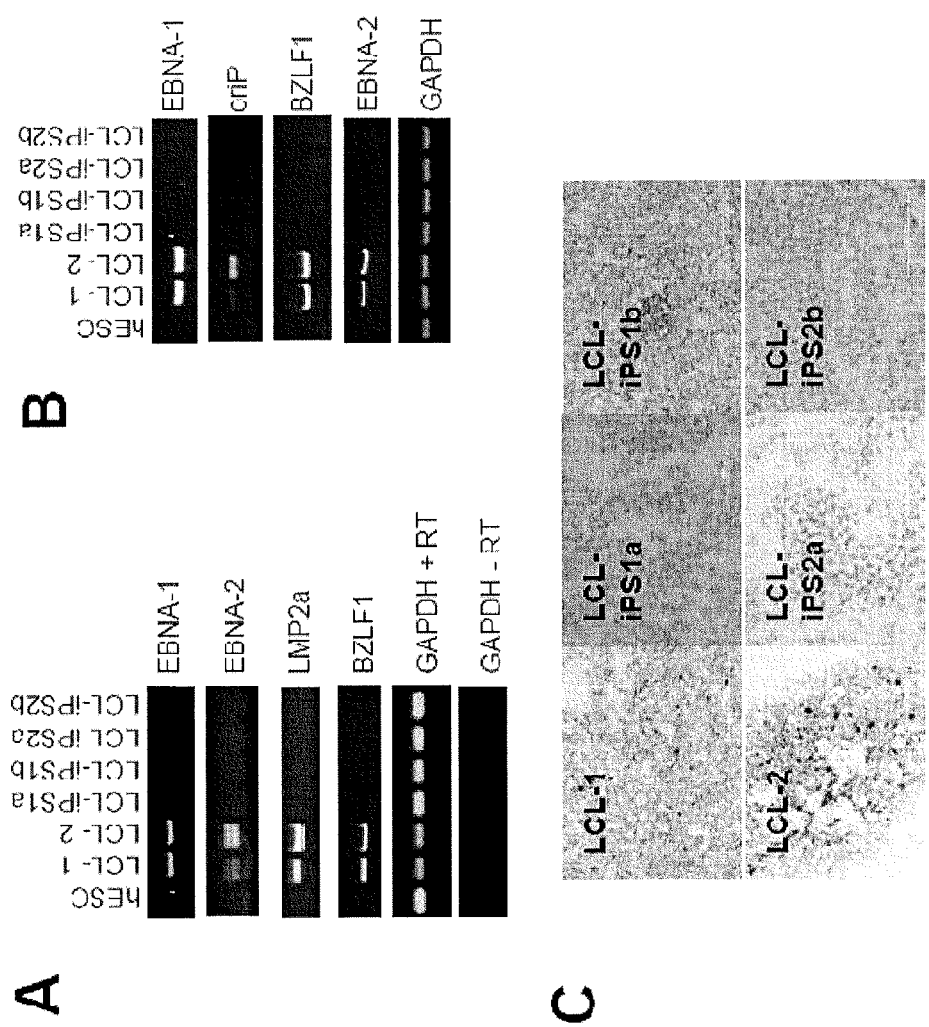
FIGS. 8A-8E: Analysis of LCL-iPSCs for reprogramming and viral elements and trilineage differentiation of LCL-iPSCs.
Figure 8D:
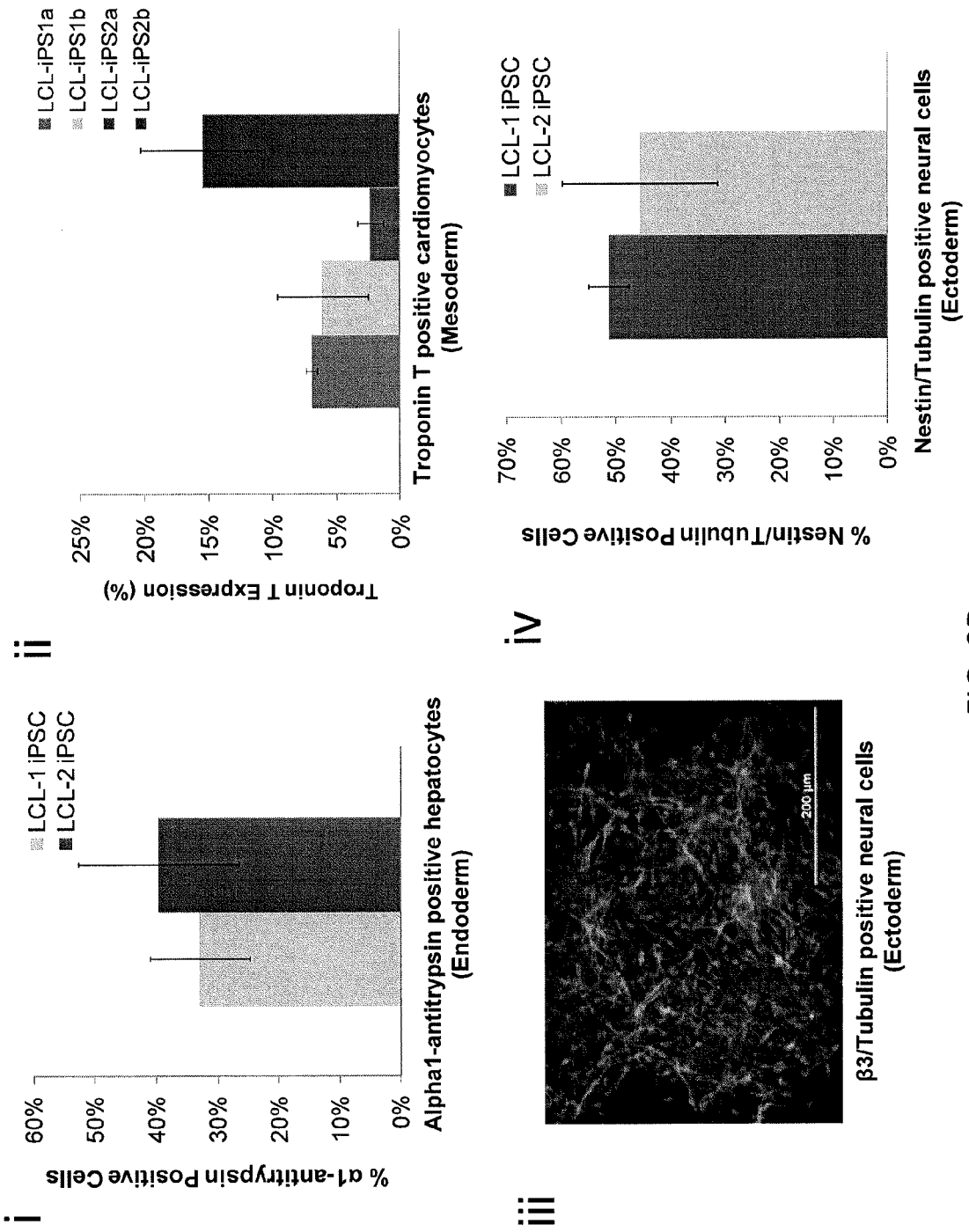
Figure 8D:
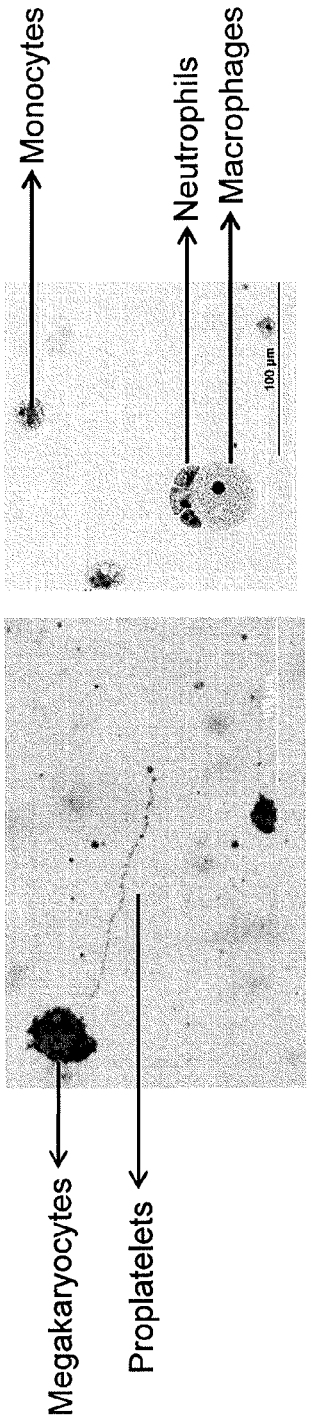
Figure 8D:
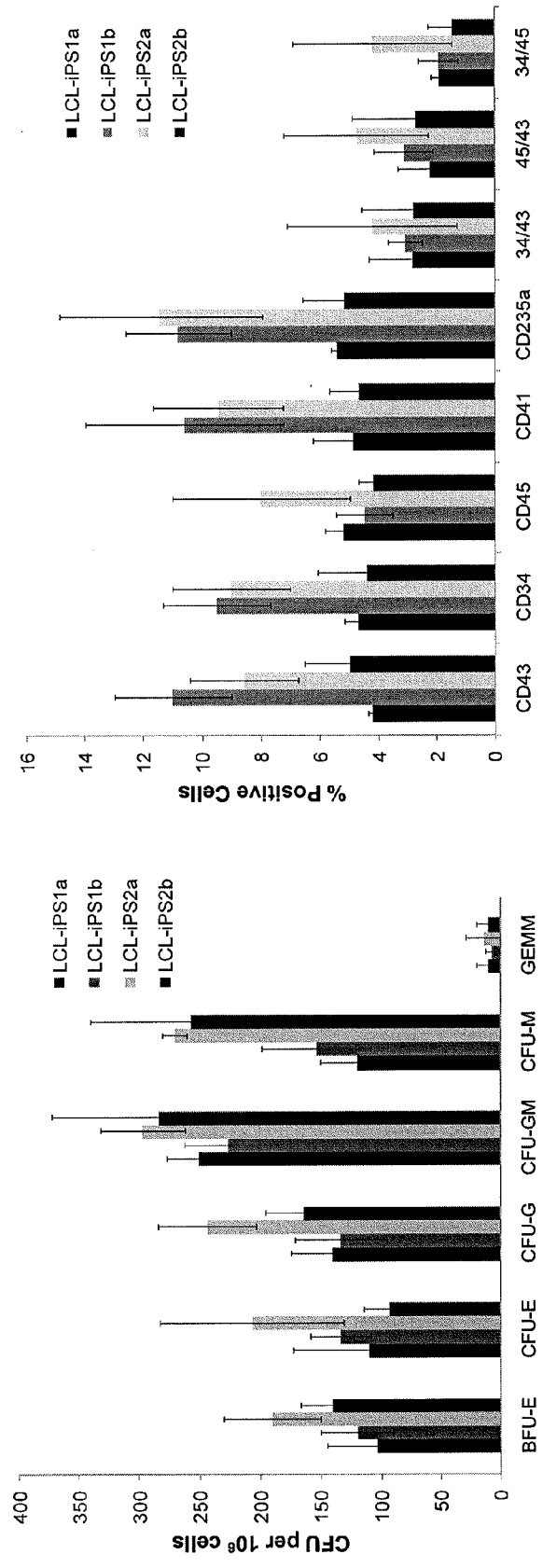
Figure 8E:
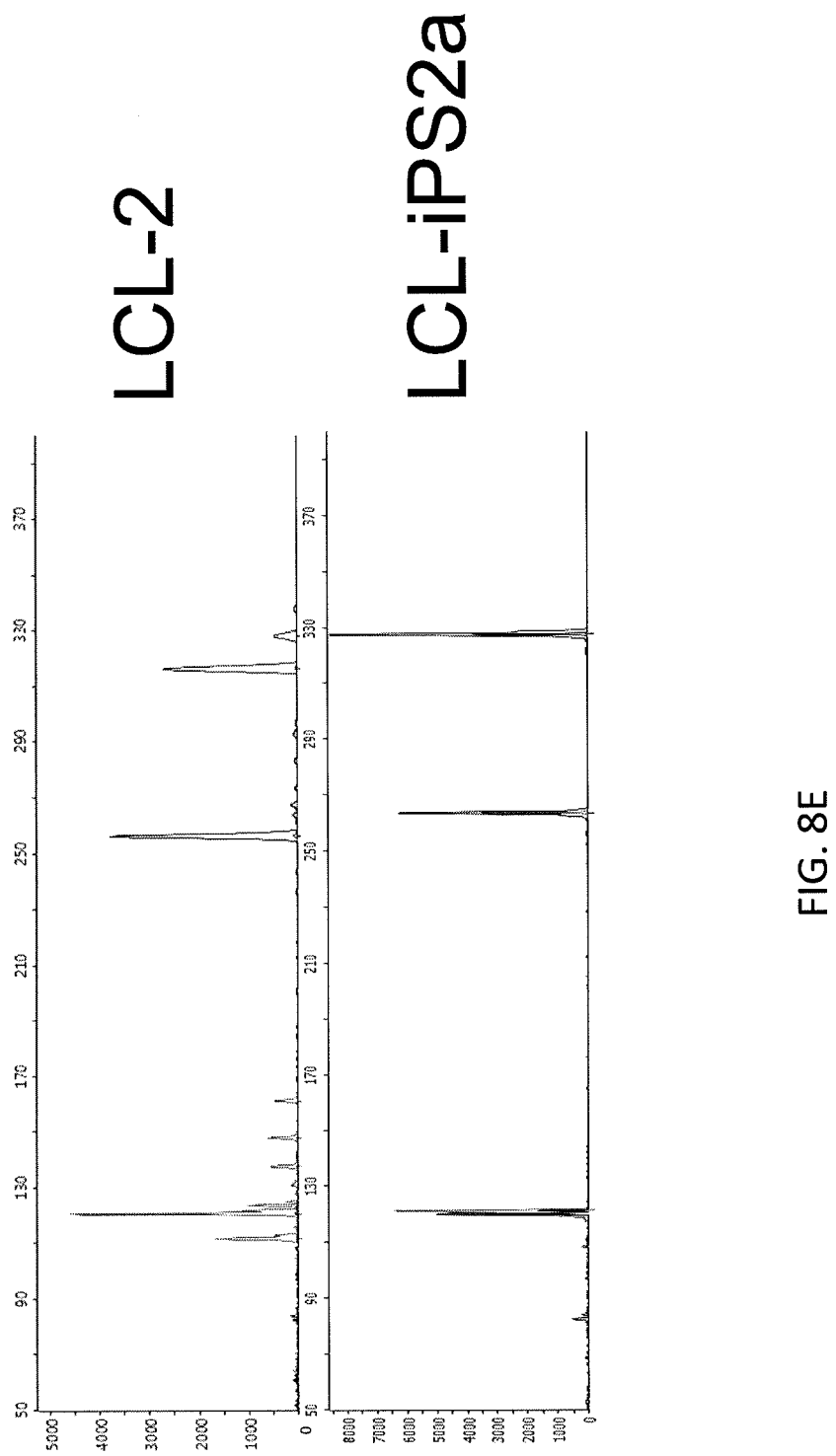

Extensive characterization was performed on two clones derived from each LCL. iPSCs derived from LCL-1 were termed, LCL-iPS 1a and 1b while those derived from LCL-2, LCL-iPS2a and iPS2b. All LCL-iPS clones had greater than 90% expression of SSEA-4, Tra-1-81 and OCT3/4 (FIG. 7Cii) and a normal karyotype (FIG. 7Ciii). RT-PCR analysis demonstrated robust expression of pluripotency-associated transcripts (FIG. 7Civ) and absence of reprogramming elements (FIGS. 7E-7F). All 4 LCL-iPSCs generated well-differentiated teratomas and revealed the presence of mesoderm (cartilage), goblet cells (endoderm) and neural rosettes (ectoderm) (FIG. 7D). In vitro differentiation of LCL-iPSCs was performed using 3D suspension cultures. Endodermal potential was confirmed by generating hepatocyte-like cells and quantifying Alpha1-Antitrypsin positive cells (FIG. 8Di). Ectodermal potential was confirmed by development of β3-tubulin/Nestin double-positive neural precursor cells and the presence of β3-tubulin positive neural cultures (FIG. 8Diii-iv). Mesodermal potential was confirmed by generating cardiomyocytes and multipotent HPCs. LCL-iPSCs generated beating aggregates expressing 2-15% cardiac troponin T positive cells on day 14 of differentiation (FIG. 8Dii). LCL-iPSCs generated CD34+, CD45+, CD43+, CD41+and CD235a expressing HPCs and formed colonies in methylcellulose based colony forming assays and subsequently generated defined cell types like megakaryocytes, macrophages and granulocytes (FIG. 8Dv-vii). Thus LCLs-iPSCs are capable of generating terminally differentiated lineages. LCL-iPSCs maintained identity to the parental LCLs and have been successfully propagated for at least 50 passages. LCL-iPSCs displayed a clonal IgGH rearrangement profile (FIG. 8E) similar to the parental LCLs. The IgGH spectrum can serve as a clone tracking tool for LCL-iPSCs (Kuppers, 2009; van Dongen et al., 2003).

Since EBNA-1 is required for establishment of episomal latent infection, long-term survival of LCLs (Leight and Sugden, 2000; Altmann et al., 2006) and is the only viral protein absolutely required for persistence of EBV infection in host cells. LCL-iPSCs were tested for the presence of EBNA-1 at early and late passages. No expression of EBNA-1 was detectable at the genomic/episomal, transcriptional (FIGS. 8A-8B) and protein levels (FIG. 8C) in the LCL-iPSCs after 25 passages. However, EBV can persist in quiescent cells in latency type 0 without any detectable EBNA-1 expression (Thorley-Lawson and Gross, 2004). Therefore absence of EBNA-1 expression (FIG. 8A) alone does not indisputably indicate a loss of EBV. The absence of detectable EBNA-1 and oriP sequence along with absence of additional viral latency genes, EBNA-2 and LMP-2A as well as lytic gene BZLF-1 (FIGS. 8A-8B) further confirmed the loss of viral elements as a result of the reprogramming process. Although a thorough analysis is needed to document the complete loss of EBV in LCL-iPSCs, the generation of EBV free LCL-iPSCs or defined cell types derived from EBV-free LCL-iPSCs leads us to speculate on the potential clinical application of these cells for future transplantation studies.

Cell Culture and Maintenance of iPSCs.

Lymphoblastoid cell lines (LCLs) were maintained with RPMI1640 containing 15% FBS at 37° C. and 5% $CO_2$ in a humidified incubator. The derivation of iPSCs from LCLs was performed on Matrigel-coated tissue culture plates. The cells were transitioned to reprogramming medium 12 hours post transfection. The reprogramming medium consisted of DMEM/F 12 supplemented with non-essential amino acids (NEAA), Glutamax, N2, B27 (all from Invitrogen), 0.1 mM β-mercaptoethanol, 100 ng/mL zebrafish basic fibroblast growth factor (zbFGF), 0.5 μM PD0325901, 3 μM CHIR99021, 0.5 μM A-83-01 (all from Stemgent), 1000 units/mL hLIF (Millipore) and 10 μM HA-100 (Santa Cruz). The cells were fed with fresh medium every other day for two weeks. Between days 14-20 the culture medium was transitioned to TesR-2 medium. Colonies with morphology similar to iPS colonies were readily visible between days 14-20 post-transfection. The presence of true-iPS colonies was confirmed by morphology and live-cell staining with Tra-1-60 antibody. All LCL derived iPS cells were maintained on Matrigel-coated tissue culture dishes in TeSR-2 Complete Medium (Stem cell Technologies).

Episomal Vectors.

Construction of the oriP/EBNA-1-based episomal vectors is described by Yu et al. (Yu et al., 2009). Six of the reprogramming plasmids were used for the generation of LCL-iPSCs. Briefly, OSNK is an oriP/EBNA-1 plasmid which uses the internal ribosome entry site 2 (IRES2) mediated expression of OCT4, SOX2, NANOG and KLF4. The following plasmids use the same backbone for expression: OSTK encodes OCT4, SOX2, SV40 Large T antigen and KLF4, OSNL encodes OCT4, SOX2, NANOG and Lin28 OSTN encodes OCT4, SOX2, SV40 Large T antigen and NANOG, c-mL encodes c-MYC and LIN28 and L-mL encodes L-MYC and LIN28.

Reprogramming LCLs.

Reprogramming LCLs with various combinations of episomal vectors described above and outlined in FIG. 8B was performed via nucleofection using the Human B Cell 96-well Nucleofector Kit (Lonza) and program E0-100 with 1-2 μg of DNA per reaction. Nucleofected cells (~1.0E+06 cells per condition) were allowed to recover a few hours and directly plated to Matrigel-coated 6-well plates in reprogramming medium.

Immunofluorescence, Immunoperoxidase and Alkaline Phosphatase Staining.

Tra-1-60 live-cell staining was performed by incubating cells with 10 µg of Tra-1-60 primary antibody (R&D Systems) for 1 hour, washing briefly three times with DMEM/F12 then incubating with 1:100 dilutions of IgM AlexaFluor488-conjugated secondary antibody (Invitrogen) for 30 minutes. Stained cells were washed and Tra-1-60 colonies were visualized by fluorescent microscopy. Alkaline Phosphatase (AP) staining was performed using the Vector Blue Alkaline Phosphatase Substrate Kit III (Vector Laboratories) according to the manufacturer's instructions.

Cytospin cell preps were made from cell suspensions of parental LCLs and LCL-iPSCs and fixed with acetone. Slides were next rehydrated in PBS, permeabilized with 0.5% triton in PBS and, blocked with 10% bovine serum albumin (BSA) for 1 hour at room temperature. The cytospins were stained using anti-EBNA-1 (Santa Cruz, clone 0211) overnight at 4° C. Sections were washed and stained with goat anti-mouse IgG HRP or the relevant isotype control antibody. The signal was visualized with diaminobenzidine and the slides were counterstained with hematoxylin for contrast.

Images were captured using an Olympus IX-71 with an Olympus DP-70 camera.

RT-PCR.

Total RNA and cDNA for each sample were prepared using the RNeasy Mini Plus kit (Qiagen) and the Improm II Reverse Transcription kit (Promega), respectively, following the manufacturer's instructions. RT-PCR to analyze transgene and endogenous mRNA expression was carried out using primers previous described by Yu et al (2007). Primers used to detect additional EBV genes are as follows: EBNA-2 F 5'-CAT AGA AGA AGA AGA GGA TGA AGA-3' (SEQ ID NO:1) and EBNA-2 R 5'-GTA GGG ATT CGA GGG AAT TAC TGA-3' (SEQ ID NO:2), LMP-2A F 5'-AGG AAC GTG AAT CTA ATG AAG A-3' (SEQ ID NO:3) and LMP-2A R 5'-AAG TGA CAA CCG CAG TAA GCA-3', BZLF-1 F 5' (SEQ ID NO:4)-CAC GGT AGT GCT GCA GTT GC-3' (SEQ ID NO:5) and BZLF-1 R 5'-CCC AGA ATC AAC AGA CTA ACC AAG CCG-3' (SEQ ID NO:6). PCR was run using 1 µL of diluted cDNA template (1:2) for 30 to 35 cycles at 95° C. for 30 s, 55° C. for 30 s, and 72° C. for 30 s.

Genomic/Episomal DNA PCR.

Total cellular and viral DNA was isolated using the DNeasy Blood and Tissue kit (Qiagen) according to the manufacturer's instructions. PCR to detect episomal reprogramming vector and viral DNA was performed using primers previous described (Yu et al., 2009; Yu et al., 2007) or the primer sets listed above. PCR was run using 150 ng of gDNA per reaction for 30 to 35 cycles at 95° C. for 30 s, 55° C. for 30 s, and 72° C. for 30 s.

In Vitro Differentiation.

LCL-iPSCs maintained for over 25 passages on Matrigel were used for all in vitro differentiation experiments.

Endodermal, neural, cardiac and hematopoietic cultures were dissociated into single-cell suspension using TrypLE (Invitrogen), and the first step included the formation of aggregates in ultra-low attachment flasks in the presence of a rock inhibitor, H1152 (EMD Biosciences), for 24 hours.

Hematopoietic differentiation was performed by placing the cells in IMDM medium supplemented with NEAA, Glutamine (Invitrogen) and 2% SR3 (Sigma) in the presence of 25 ng/mL zbFGF, 50 ng/mL rhBMP4 (R&D Systems), 50 ng/ml rhVEGF, 25 ng/mL, rhFlt-3 ligand, 25 ng/mL rhSCF, 25 ng/mL rhIL-3, and 25 ng/mL rhIL-6 (All from ProSpec-Tany TechnoGene Ltd.) for 12 days. The cells were harvested and the stained for the presence of CD31, CD34, CD43, CD45, CD41 and CD235a and assayed by flow cytometry. The individualized cells were placed in MethoCult (Stem Cell Technologies) media for quantifying colony-forming units per the manufacturer's instructions HPCs derived from LCL-iPSCs were placed in MegaCult®-C collagen-based medium (Stem Cell Technologies) to detect megakaryocyte progenitors. Megacult cultures were stained after 10 days to detect the presence of Mk-specific antigen GP11b/111a (CD41) on megakaryocytes according to the manufacturer's instructions.

HPCs derived from LCL-iPSCs were expanded for 10 days to enrich the myeloid cells. The cells were placed in SFEM media (Stem Cell Technologies) supplemented with 1% Excyte (Serologicals), monothioglycerol (450 µM, Sigma), NEAA (0.1 mM), L-glutamine (2 mM), GM-CSF (100 ng/mL, ProSpec-Tany TechnoGene Ltd.). Wright stain was performed on cytospins to detect the presence of different cell types. The cultures were also stained for the presence of macrophage (CD68), granulocytic (CD15) and monocytic (CD14) specific antigens by flow cytometry (data not shown).

Cardiac differentiation was performed by placing the aggregates in DMEM/F12 supplemented with 10% FBS and zbFGF-2 for 7 days and transitioning to DMEM/F12 supplemented with 10% FBS for the next 8 days. Beating aggregates were dissociated and stained for the presence of cardiac troponin T (cTnT) (Abeam) on day 14 of differentiation.

Neural differentiation was induced by placing the aggregates in DMEM/F12 supplemented with 1% N2 supplement, 0.5-1 µM dorsomorphin and 5 µM SB 431542 (both Sigma Aldrich) for one week, followed by transition to DMEM/F12 containing N2 and B27 supplements alone for additional two weeks. The neural aggregates were individualized around day 20 of differentiation and plated on Matrigel coated plates for additional 1-2 weeks. The expression of β3-tubulin and nestin was quantified by flow cytometry. The cells were also stained to detect the presence of β3-tubulin by immunofluorescence, and the nuclei were counterstained with Hoechst for DNA staining. Anti-tubulin and anti-nestin antibodies were purchased from BD Pharmingen.

Endodermal differentiation was induced by placing the aggregates in RPMI1640 media supplemented with 2% N2 supplement and 50-100 ng/mL of activin A (Invitrogen) for the first 3-4 days followed by the addition of 10-50 ng/mL of BMP4 (R&D Systems), zbFGF-2 and HGF2 (R&D Systems) for the next two weeks. The hepatocyte-like cells were matured in the presence of oncostatin M (R&D Systems) and dexamethasone (Sigma), and the cultures were harvested at day 33 of differentiation.

Teratoma Formation.

LCL-iPSCs maintained on Matrigel-coated plates in the presence of TeSR-2 were harvested using collagenase IV and injected intramuscularly into the hind limb of SCID/beige mice (Harlan Laboratories, Madison, Wis.). Three mice were injected per cell line, each with one 6-well plate of cells. Matrigel was added at ⅓ total volume to the cell suspension prior to injection. Tumors formed at 8-10 weeks and were processed for hematoxylin and eosin staining and histological analysis by the Immunohistochemical Core Service affiliated with the Department of Surgery located at the University of Wisconsin-Madison. All animal work was conducted according to relevant national and international guidelines under the approval of the Cellular Dynamics International Animal Care and Use Committee.

DNA Fingerprinting.

Genomic DNA was isolated from LCL-iPSCs and parental LCLs using the DNeasy Blood and Tissue kit (Qiagen). The samples were sent to WiCell Research Institute and Cell Line Genetics for short tandem repeat (STR) analysis. Genotypes for 8 STR loci were analyzed on the parental and LCL-iPSCs.

Karyotyping.

G-banding analysis was conducted by WiCell Research Institute.

IgGH Rearrangement Analysis.

Genomic DNA was isolated per manufacturer's protocol (using the DNeasy Blood and Tissue kit) from parental LCLs and the LCL-iPSCs. The IgG heavy chain gene rearrangement assays were performed by a multiplexed PCR reaction by Hematologics to detect distinct monoclonal amplicons for the three immunoglobulin heavy chain framework regions.

Flow Cytometry Analysis.

LCL-iPSCs maintained on Matrigel were harvested and stained for the presence of Tra-1-81 (AlexaFluor488-conjugated TRA-1-81, Millipore), and SSEA-4 (BD Pharmingen, clone MC813-70). Dead cells stained by propidium-iodide were excluded from the analysis. Intracellular OCT3/4 (BD, clone 40/OCT-3) staining was performed on cells fixed with 2% paraformaldehyde and permeablized with PBS +0.1% saponin. Cells were stained overnight and analyzed the next day on a flow cytometer (Accuri). Isotype antibodies (BD Pharmingen) were used as controls.

For in vitro differentiation studies, LCL-iPSCs were stained using polyclonal Alpha1-Antitrypsin antibody (Bethyl Laboratories) to quantify hepatocyte-like cells. Neural precursor cells derived from LCL-iPSCs were stained using anti-tubulin (TUJ1) and nestin (25/NESTIN), BD Pharmingen. For cardiac differentiation the cells were stained using anti-cardiac troponin T antibody (Abcam, clone 1C11). LCL derived HPCs were quantified by surface staining of hematopoietic precursors with: pan CD45 (clone HI30); CD43 (clone1G10); CD34 (clone 581); CD41 (clone HIP8); CD235a (clone HIR2) antibodies (all from BD Biosciences).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Appln. 61/258,120
U.S. Appln. 61/088,054
U.S. Appln. 61/156,304
U.S. Appln. 61/172,079
U.S. Appln. 61/323,689
U.S. Pat. No. 4,683,202
U.S. Pat. No. 4,684,611
U.S. Pat. No. 4,952,500
U.S. Pat. No. 5,302,523
U.S. Pat. No. 5,322,783
U.S. Pat. No. 5,384,253
U.S. Pat. No. 5,464,765
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,624
U.S. Pat. No. 6,280,718
U.S. Pat. No. 6,458,589
U.S. Pat. No. 6,506,574
U.S. Pat. No. 6,833,269
U.S. Publn. 2003/0166273 A1
U.S. Publn. 2003/0153082 A1
U.S. Publn. 2003/0211603
U.S. Publn. 2004/0009589 A1
U.S. Publn. 2005/0037493 A1
U.S. Publn. 2005/0214939 A1
U.S. Publn. 2007/0238170
U.S. Publn. 2008/0038820
U.S. Publn. 2008/004287
U.S. Publn. 2008/0226558
U.S. Publn. 2008/0254003
U.S. Publn. 2009/0047739
U.S. Publn. 2010/0003757
Adams, *J. Virol.*, 61(5):1743-1746, 1987.
Aiyar et al., *EMBO J.*, 17(21):6394-6403, 1998.
Alexander et al., *Proc. Nat. Acad. Sci. USA*, 85:5092-5096, 1988.
Altmann et al., *Proc. Natl. Acad. Sci. USA*, 103(38):14188-14193, 2006.
Amoli et al. *Int. J. Epidemiol.*, 37(Suppl 1):41-45, 2008.
Andrews et al., In: *Teratocarcinomas and Embryonic Stem Cells*, Robertson (Ed.), IRL Press, 207-246,1987.
Aravind and Landsman, *Nucleic Acids Res.*, 26(19):4413-4421, 1998.
Ausubel et al., In: *Current Protocols in Molecular Biology*, John, Wiley & Sons, Inc, New York, 1994.
Baer et al., *Nature*, 310(5974):207-211, 1984.
Bain et al., *Biochem. J*, 408(3):297-315, 2007.
Bennett et al, *J. Biol. Chem.*, 277:34, 2002.
Bertrand et al., *J. Mol. Biol.*, 333(2):393-407, 2003.
Bode et al., *Gene Ther. Mol. Biol.*, 6:33-46, 2001.
Bode et al., *Science*, 255(5041):195-197,1992.
Brown et al. *PLoS One*, 5:e11373, 2010.
Cahir-McFarland et al., *J. Virol.*, 78(8):4108-19, 2004.
Cahir-McFarland et al., *Proc. Natl. Acad. Sci. USA*, 97(11):6055-60, 2000.
Carbonelli et al., *FEMS Microbiol. Lett.*, 177(1):75-82, 1999.
Carey et al., *Proc. Natl. Acad. Sci. USA*, 106:157-162, 2009.
Carpenter et al., *Exp Neurol.*, 172(2):383-97, 2001.

Chadwick et al., *Blood*, 102(3):906-15, 2003.
Chandler et al., *Proc. Natl. Acad. Sci. USA*, 94(8):3596-601, 1997.
Chang, et al., *Frontiers in Bioscience*, 12:4393-4401, 2007.
Chaudhuri et al., *Proc. Natl. Acad. Sci. USA*, 98(18):10085-10089, 2001.
Chen and Okayama, *Mol. Cell Biol.*, 7(8):2745-2752, 1987.
Chin et al., *Molecular Brain Res.*, 137(1-2):193-201, 2005.
Chow et al., *Cytometry Commun. Clinical Cytometry*, 46:72-78, 2001.
Chung et al., *Trends Immunol.*, 24(6):343-9, 2003.
Cobaleda and Busslinger, *Curr. Opin. Immunol.*, 20:139-148. 2008.
Cobaleda, *Methods Mol. Biol.*, 636:233-250., 2010
Cocea, *Biotechniques*, 23(5):814-816, 1997.
DaCosta et al., *Molec. Pharmacol.*, 65(3):744-752, 2004.
Davies et al., *Biochem J.*, 351:95-105, 2000.
De Benedetti and Rhoads, *Nucleic Acids Res.*, 19:1925-1931, 1991.
de Gouville et al., *Drug News Perspective*, 19(2):85-90, 2006.
Delecluse et al., *Proc. Natl. Acad. Sci. USA*, 95(14):8245-50, 1998.
Delecluse et al., *Proc. Natl. Acad. Sci. USA*, 96(9):5188-93, 1999.
Dhar et al., *Cell*, 106(3):287-296, 2001.
Downey et al., *J. Biol. Chem.*, 271(35):21005-21011, 1996.
English et al., *Trends in Pharmac. Sci.*, 23(1):40-45, 2002.
Ercolani et al., *J. Biol. Chem.*, 263:15335-15341,1988.
Ermakova et al., *J. Biol. Chem.*, 271(51):33009-33017, 1996.
European Appln. EP1507865
European Appln. EPO 0273085
Evans et al., In: *Cancer Principles and Practice of Oncology*, Devita et al. (Eds.), Lippincot-Raven, NY, 1054-1087, 1997.
Fechheimer et al., *Proc Natl. Acad. Sci. USA*, 84:8463-8467, 1987.
Fraley et al., *Proc. Natl. Acad. Sci. USA*, 76:3348-3352, 1979.
Frame et al, *Biochemical J.*, 359:1-16, 2001.
Frappier and O'Donnell, *Proc. Natl. Acad. Sci. USA*, 88(23):10875-10879, 1991.
Fu et al., *Blood*, 113(19):4627-36, 2009.
Gahn and Schildkraut, *Cell*, 58(3):527-535, 1989.
Gahn and Sugden, *J. Virol.*, 69(4):2633-2636, 1995.
Gaspar-Maia et al., *Nat. Rev. Mol. Cell Biol.*, 12:36-47, 2011.
Gassmann et al., *Proc. Natl. Acad. Sci. USA*, 92:1292-1296, 1995.
Gellibert, et al., *J. Med. Chem.*, 49(7):2210-2221, 2006.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gopal, *Mol. Cell Biol.*, 5:1188-1190, 1985.
Gorman et al., *Cell*, 42(2):519-26, 1985.
Gould et al, *Intl. J. Neuropsychopharmacology*, 7:387-390, 2004.
Gould et al, *Pharmacological Res.*, 48:49-53, 2003.
Graham and Van Der Eb, *Virology*, 52:456-467, 1973.
Hanna et al., *Cell*, 133:250-264, 2008.
Harada and Kieff, *J. Virol.*, 71(9):6611-8, 1997.
Harland and Weintraub, *J. Cell Biol.*, 101(3):1094-1099, 1985.
Hettich et al., *Gene Ther.*, 13(10):844-56, 2006.
Hudson et al., *Virology*, 147(1):81-98, 1985.
Inman et al., *Molec. Pharmacol.*, 62(1):65-74, 2002.
Jenke et al., *Proc. Natl. Acad. Sci. USA*, 101 (31), 11322-11327, 2004.
Jia et al. *Nat. Methods*, 7:197-199, 2010.
Julien et al., *Virology*, 326(2):317-328, 2004.
Kaeppler et al., *Plant Cell Rep.*, 8:415-418, 1990.
Kaji et al., *Nature*, 458, 771-775, 2009.
Kaminska et al., *Acta Biochimica Polonica*, 52(2):329-337, 2005.
Kanda et al., *Mol. Cell. Biol.*, 21(10):3576-3588, 2001.
Kaneda et al., *Science*, 243:375-378, 1989.
Kanteti et al., *Lab Invest.*, 89(3):301-14, 2009.
Karin et al. *Cell*, 36: 371-379,1989.
Kato et al, *J. Biol. Chem.*, 266:3361-3364, 1991.
Keirstead et al., *J. Neurosci.*, 25(19):4694-705, 2005.
Kennedy and Sugden, *Mol. Cell. Biol.*, 23(19):6901-6908, 2003.
Kennedy et al., *Proc. Natl. Acad. Sci. USA*, 100:14269-14274, 2003.
Kilger et al, *EMBO J.*, 17(6):1700-9, 1998.
Kim et al., *Xenobiotica*, 38(3):325-339, 2008.
Kira et al., *Antimicrob. Agents Chemother.*, 44(12):3278-84, 2000.
Kirchmaier and Sugden, *J. Virol.*, 69(2):1280-1283, 1995.
Kirchmaier and Sugden, *J. Virol.*, 71(3):1766-75, 1997.
Kirchmaier and Sugden, *J. Virol.*, 72(6):4657-4666, 1998.
Klein et al, *Neoplasia*, 8:1-8, 2006.
Klein et al., *Nature*, 327:70-73, 1987.
Klimanskaya et al., *Cloning Stem Cells*, 6(3):217-45, 2004.
Knight and Robertson, *J. Virol.*, 78(4):1981-91, 2004.
Kuppers, *Blood*, 114:3970-3971, 2009.
Langle-Rouault et al., *J. Virol.*, 72(7):6181-6185, 1998.
Leblois et al., *Mol. Ther.*, 1(4):314-22, 2000.
Leight and Sugden, *Rev. Med. Virol.*, 10:83-100, 2000.
Levenson et al., *Hum. Gene Ther.*, 9(8):1233-1236, 1998.
Levitskaya et al., *Proc. Natl. Acad. Sci. USA*, 94(23):12616-12621, 1997.
Lin et al., *Nat. Methods*, 6:805-808, 2009.
Lin et al., *Science*, 221(4610):578-9, 1983.
Lindner and Sugden, *Plasmid*, 58:1-12, 2007.
Ludwig et al., *Nat. Biotechnol.*, 24(2):185-187, 2006b.
Ludwig et al., *Nat. Methods*, 3(8):637-46, 2006a.
Macejak and Sarnow, *Nature*, 353:90-94, 1991.
Mack and Sugden, *Cancer Res.*, 68(17):6963-8, 2008.
Mackey and Sugden, *Mol. Cell. Biol.*, 19(5):3349-3359, 1999.
Mackey et al., *J. Virol.*, 69(10):6199-6208, 1995.
Maniatis, et al., *Molecular Cloning, A Laboratory Manual*, Cold Spring Harbor Press, Cold Spring Harbor, N.Y., 1988.
Manzini et al., *Proc. Natl. Acad. Sci. USA*, 103(47):17672-17677, 2006.
Marechal et al., *J. Virol.*, 73(5):4385-4392, 1999.
Margolskee et al., *Mol. Cell. Biol.*, 8:2837-2847, 1988.
Marie-Cardine et al., *Clin. Immunol.*, 127(1):14-25, 2008.
Martin, et al., *Nature Immunology*, 6:111-184, 2005.
Mattingly et al, *J. Pharmacol. Experimen. Therap.*, 316:456-465, 2006.
Middleton and Sugden, *J. Virol.*, 66(1):489-495, 1992.
Munsie et al., *Curr. Biol.*, 10:989, 2000.
Nabel et al., *Science*, 244(4910):1342-1344, 1989.
Nanbo et al., *EMBO J.*, 26:4252-62, 2007.
Narazaki, et al., *Circulation*, 118(5):498-506, 2008.
Ng et al., *Development*, 132(5):873-84, 2005.
Ng, *Nuc. Acid Res.*, 17:601-615,1989.
Nicolau and Sene, *Biochim. Biophys. Acta*, 721:185-190, 1982.
Nicolau et al., *Methods Enzymol.*, 149:157-176, 1987.
Niller et al., *J. Biol. Chem.*, 270(21):12864-12868, 1995.
Noble et al, *Proc. Natl. Acad. Science, USA*, 102:6990-6995, 2005.
Norseen et al., *J. Virol.*, 83(20):10336-46, 2009.
Ohe et al., *Hum. Gene Ther.*, 6:325-333, 1995.

Okita and Yamanaka, *Exp. Cell Res.*, 316:2565-2570, 2010.
Okita et al., *Nat. Protoc.*, 5:418-428, 2010.
Okita et al., *Science*, 322:949-953, 2008.
Omirulleh et al., *Plant Mol. Biol.*, 21(3):415-428, 1993.
Pannell et al., *EMBO J.*, 19(21):5884-94, 2000.
Parcells et al., *J. Virol.*, 73(2):1362-1373, 1999.
Parker et al., *J. Virol.*, 70(8):5731-4, 1996.
PCT Appln. WO 01/81549
PCT Appln. WO 03/000868
PCT Appln. WO 03/004605
PCT Appln. WO 03/006950
PCT Appln. WO 03/050249
PCT Appln. WO 03/050250
PCT Appln. WO 03/050251
PCT Appln. WO 04/007696
PCT Appln. WO 07/113505
PCT Appln. WO 08/006583
PCT Appln. WO 08/094597
PCT Appln. WO 94/09699
PCT Appln. WO 95/06128
PCT Appln. WO 99/20741
Pelletier and Sonenberg, *Nature*, 334:320-325, 1988.
Perales et al., *Proc. Natl. Acad. Sci. USA*, 91:4086-4090, 1994.
Piechaczek et al., *Nucleic Acids Res.*, 27:426-428, 1999.
Potrykus et al., *Mol. Gen. Genet.*, 199(2):169-177, 1985.
Potter et al., *Proc. Natl. Acad. Sci. USA*, 81:7161-7165, 1984.
Quitsche et al., *J. Biol. Chem.*, 264:9539-9545,1989.
Rahman et al., *J. Exp. Med.*, 193(3):237-44, 2001.
Rawlins et al., *Cell*, 42((3):859-868, 1985.
Reisman and Sugden, *Mol. Cell. Biol.*, 6(11):3838-3846, 1986.
Reisman et al., *Mol. Cell. Biol.*, 5(8):1822-1832, 1985.
Richards et al., *Cell*, 37:263-272, 1984.
Rinehart et al., *J. Clinical Oncol.*, 22:4456-4462, 2004.
Ring et al., *Diabetes*, 52:588-595, 2003.
Rippe, et al., *Mol. Cell Biol.*, 10:689-695, 1990.
Ritzi et al., *J. Cell Sci.*, 116(Pt 19):3971-3984, 2003.
Sambrook et al., *Molecular Cloning: A Laboratory Manual*, Cold Spring Harbor, Cold Spring Harbor Press, 1989.
Schaarschmidt et al., *EMBO J*, 23(1):191-201, 2004.
Schaffer et al.; *Gene*, 302(1-2):73-81, 2003.
Schepers et al., *EMBO J.*, 20(16):4588-4602, 2001.
Sears et al., *J. Virol.*, 78(21):11487-11505, 2004.
Sinclair et al, *EMBO J.*, 13(14):3321-8, 1994,
Sompallae et al., *PLoS One*, 5:e12052, 2010.
Su et al., *Proc. Natl. Acad. Sci. USA*, 88(23):10870-19874, 1991.
Sugden and Warren, *J. Virol.*, 63(6):2644-2649, 1989.
Sun et al., *Proc. Natl. Acad. Sci. USA*, 107(7):3146-51, 2010.
Suzuki et al., *Cancer Res.*, 67(5):2351-2359, 2007.
Thorley-Lawson and Gross, *N. Engl. J. Med.*, 350:1328-1337, 2004.
Tojo et al., *Cancer Science*, 96(11):791-800, 2005,
Tur-Kaspa et al., *Mol. Cell Biol.*, 6:716-718, 1986.
van Dongen et al., *Leukemia*, 17:2257-2317, 2003.
Wada et al., *Int. Immunol.*, 23:65-74, 2011.
Wagman, *Current Pharmaceutical Design*, 10:1105-1137, 2004.
Wagner et al., *Proc. Natl. Acad. Sci. USA* 87(9):3410-3414, 1990.
Wang et al., *Mol. Cell. Biol.*, 26(3):1124-1134, 2006.
Wang et al., *Mol. Cell. Biol.*, 26(3):1124-1134, 2006.
Wang et al., *Proc. Natl. Acad. Sci. USA*, 104:7612-7616, 2007.
Warren et al., *Cell Stem Cell*, 7:618-630, 2010.
Wendtner et al., *Exp. Hematol.*, 31(2):99-108, 2003.
Wilson et al., *Science*, 244:1344-1346, 1989.
Woltjen et al., *Nature*, 458, 766-770, 2009.
Woltjen et al., *Nature*, 458:766-770, 2009.
Wong et al., *Gene*, 10:87-94, 1980.
Wrzesinski et al., *Clinical Cancer Res.*, 13(18):5262-5270, 2007.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Wysokenski and Yates, *J. Virol.*, 63(6):2657-2666, 1989.
Xu et al., *Dev. Cell*, 2:251-252, 2002.
Yamanaka et al., *Cell*, 131(5):861-72, 2007.
Yamanaka, *Cell Stem Cell*, 1:39-49, 2007.
Yang and Russell, *Proc. Natl. Acad. Sci. USA*, 87:4144-4148, 1990.
Yates and Guan, *J. Virol.*, 65(1):483-488, 1991.
Yates et al., *J. Virol.*, 74(10):4512-4522, 2000.
Yates et al., *Nature*, 313:812-815, 1985.
Yates et al., *Nature*, 313:812-815, 1985.
Yates et al., *Proc. Natl. Acad. Sci. USA*, 81:3806-3810, 1984.
Yates, *Cancer Cells*, (6)197-205, 1988.
Ying, *Nature*, 453:519-23, 2008.
Yu et al., *Antimicrob. Agents Chemo.*, 53(10):4311-4319, 2009.
Yu et al., *Science*, 318:1917-1920, 2007.
Yu et al., *Science*, 318:1917-1920, 2007.
Yu et al., *Science*, 324:797-801, 2009.
Zhang et al., *Angew. Chem., Int. Ed.*, 48:2542-2545, 2009.
Zhang et al., *Bioorganic Med. Chem. Letters;* 10:2825-2828, 2000.
Zhou et al., *Cell Stem Cell*, 4:381-384, 2009.
Zhou et al., *EMBO J.*, 24(7):1406-1417, 2005.
Zhou et al., *Nature*, 462(7276):1070-4, 2009.
Zimber-Strobl et al., *J. Virol.*, 65(1):415-23, 1991.

What is claimed is:

1. A method for producing human induced pluripotent stem cells (iPS cells) from immortalized B cells, wherein the method comprises:
   a) obtaining immortalized human B cells that have been immortalized by introducing one or more immortalizing Epstein-Barr virus (EBV) elements comprising EBNA into B cells;
   b) reprogramming the immortalized B cells by introducing an exogenous reprogramming episomal vector or vectors encoding exogenous reprogramming factors comprising at least Oct-4 and Sox-2; and
   c) culturing said cells under defined conditions in the absence of a feeder layer to effect expression of the exogenous reprogramming factors therein for sufficient time to produce iPS cells; and
   d) removing the EBV and episomal vector elements from the iPS cells to provide human iPS cells that are essentially free of exogenous EBV and episomal vector elements.

2. The method of claim 1, further comprising isolating or enriching iPS cells that are essentially free of the EBV elements.

3. The method of claim 1, wherein the B cells prior to immortalization have been obtained from a blood sample.

4. The method of claim 3, wherein the blood sample has a volume of from about 0.01 mL to about 5 mL.

5. The method of claim 4, wherein the blood sample has a volume of from about 0.1 mL to about 0.5 mL.

6. The method of claim 1, wherein the immortalized B cells are obtained by immortalizing B cells using Epstein-Barr virus (EBV) elements.

7. The method of claim 1, wherein expression of the immortalizing EBV elements or reprogramming factors is under the control of an inducible.

8. The method of claim 1, wherein the immortalized B cells are obtained from an established lymphoblastoid cell line.

9. The method of claim 1, wherein reprogramming further comprises contacting the immortalized B cells with one or more signaling inhibitors including a glycogen synthase kinase 3 (GSK-3) inhibitor, a mitogen-activated protein kinase kinase (MEK) inhibitor, a transforming growth factor beta (TGF-β) receptor inhibitor, a p53 inhibitor, an NF-kappa B inhibitor, or a combination thereof.

10. The method of claim 1, wherein reprogramming further comprises contacting the immortalized B cells with fibroblast growth factor (FGF) or leukemia inhibitory factor (LIF).

11. The method of claim 1, wherein reprogramming does not include the introduction of an inhibitory nucleotide specific for Pax-5 into the immortalized B cells.

12. The method of claim 1, wherein reprogramming does not include expression of exogenous C/EBPα in the immortalized B cells.

* * * * *

UNITED STATES PATENT AND TRADEMARK OFFICE
CERTIFICATE OF CORRECTION

PATENT NO.         : 8,765,470 B2
APPLICATION NO.    : 13/197529
DATED              : July 1, 2014
INVENTOR(S)        : James Thomson et al.

Page 1 of 1

It is certified that error appears in the above-identified patent and that said Letters Patent is hereby corrected as shown below:

In title page, item (56) References Cited - Other Publications, delete the 18th reference on page 2 column 1, line 44, "Paschos et al., "Epstein-barn virus latency in B cells leads to epigenetic repression and CpG methylation of the tumour suppressor gene Bim," *PLoS Pathogens*, 5(6):e 1000492, 2009." and replace with --Paschos et al., "Epstein-barr virus latency in B cells leads to epigenetic repression and CpG methylation of the tumour suppressor gene Bim," *PLoS Pathogens*, 5(6):e 1000492, 2009.-- therefor.

In title page, item (56) References Cited - Other Publications, delete the 30th reference on page 2 column 2, line 28, "Woltjen et aL, "PiggyBac transposition reprograms fibroblasts to induced pluripotent stem cell," *Nature,* 458, 766-770, 2009." and replace with --Woltjen et al., "PiggyBac transposition reprograms fibroblasts to induced pluripotent stem cell," *Nature,* 458, 766-770. 2009.-- therefor.

In the Claims:

In claim 7, column 65, line 3, after "inducible" insert --exogenous reprogramming expression cassette--.

Signed and Sealed this
Seventh Day of October, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
catagaagaa gaagaggatg aaga                                             24
```

-continued

```
<210> SEQ ID NO 2
<211> LENGTH: 24
<212> TYPE: DNA
<213> ORGANISM: Artificial Sequence
<220> FEATURE:
<223> OTHER INFORMATION: Synthetic primer

<400> SEQUENCE: 2
gtagggattc gagggaatta ctga                                                24

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
aggaacgtga atctaatgaa ga                                                  22

<210> SEQ ID NO 4
<211> LENGTH: 21
<212> TYPE: DNA
<213> ORGANISM: Artificial Sequence
<220> FEATURE:
<223> OTHER INFORMATION: Synthetic primer

<400> SEQUENCE: 4
aagtgacaac cgcagtaagc a                                                   21

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
cacggtagtg ctgcagttgc                                                     20

<210> SEQ ID NO 6
<211> LENGTH: 27
<212> TYPE: DNA
<213> ORGANISM: Artificial Sequence
<220> FEATURE:
<223> OTHER INFORMATION: Synthetic primer

<400> SEQUENCE: 6
cccagaatca acagactaac caagccg                                             27
```